(12) United States Patent
Boitano et al.

(10) Patent No.: US 12,251,448 B2
(45) Date of Patent: *Mar. 18, 2025

(54) COMPOSITIONS AND METHODS FOR THE DEPLETION OF CD5+ CELLS

(71) Applicant: Heidelberg Pharma Research Gmbh, Ladenburg (DE)

(72) Inventors: Anthony Boitano, Newton, MA (US); Michael Cooke, Boston, MA (US); Rahul Palchaudhuri, Somerville, MA (US); Sean McDonough, Littleton, MA (US)

(73) Assignee: Heidelberg Pharma Research GmbH, Ladenburg (DE)

( * ) Notice: Subject to any disclaimer, the term of this patent is extended or adjusted under 35 U.S.C. 154(b) by 340 days.

This patent is subject to a terminal disclaimer.

(21) Appl. No.: 17/244,721

(22) Filed: Apr. 29, 2021

(65) Prior Publication Data

US 2021/0369854 A1 Dec. 2, 2021

Related U.S. Application Data

(63) Continuation of application No. 16/851,082, filed on Apr. 16, 2020, now abandoned, which is a continuation of application No. PCT/US2018/063175, filed on Nov. 29, 2018.

(60) Provisional application No. 62/592,214, filed on Nov. 29, 2017.

(51) Int. Cl.
   *A61K 47/68* (2017.01)
   *A61K 38/12* (2006.01)
   *A61K 39/00* (2006.01)
   *C07K 16/28* (2006.01)

(52) U.S. Cl.
   CPC .......... *A61K 47/6803* (2017.08); *A61K 38/12* (2013.01); *A61K 47/6849* (2017.08); *C07K 16/2896* (2013.01); *A61K 2039/505* (2013.01); *C07K 2317/92* (2013.01)

(58) Field of Classification Search
   None
   See application file for complete search history.

(56) References Cited

U.S. PATENT DOCUMENTS

| | | |
|---|---|---|
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,363,799 A | 12/1982 | Kung et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,515,894 A | 5/1985 | Kung et al. |
| 4,657,760 A | 4/1987 | Kung et al. |
| 4,675,386 A | 6/1987 | Royston et al. |
| 4,880,935 A | 11/1989 | Thorpe |
| 5,122,368 A | 6/1992 | Greenfield et al. |
| 5,208,020 A | 5/1993 | Chari et al. |
| 5,413,923 A | 5/1995 | Kucherlapati et al. |
| 5,416,064 A | 5/1995 | Chari et al. |

(Continued)

FOREIGN PATENT DOCUMENTS

| EP | 0 425 235 | 9/1996 |
|---|---|---|
| EP | 0 349 578 | 10/1998 |

(Continued)

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Strop et al., Chemistry and Biology 20: 161-167 (Year: 2013).*
Antin et al., "Selective Depletion of Bone Marrow T Lymphocytes with Anti-CD5 Monoclonal Antibodies: Effective Prophylaxis for Graft-Versus-Host Disease in Patients with Hematologic Malignancies", Blood, vol. 78, No. 8, Oct. 15, 1991, pp. 2139-2149.
Barbas III et al., "Assembly of combinatorial antibody libraries on phage surfaces: The gene III site", Proc. Natl. Acad. Sci. USA, vol. 88, Sep. 1991, pp. 7978-7982.

(Continued)

*Primary Examiner* — Phuong Huynh
(74) *Attorney, Agent, or Firm* — Grüneberg and Myers PLLC

(57) ABSTRACT

The invention provides anti-CD5 antibodies, antigen-binding fragments thereof, and antibody drug conjugates thereof, for use in treating, for example, a stem cell disorder, cancer, or autoimmune disease, among other hematological and proliferative diseases. Compositions and methods for depleting populations of CD5+ cells, such as CD5+ cancer cells and CD5+ immune cells are described, and can be used to treat cancers and autoimmune diseases directly as stand-alone therapies by eradicating cancerous cells and autoreactive immune cells that express CD5 and/or to prepare a patient for hematopoietic stem cell transplantation, for instance, by depleting populations of CD5+ immune cells that cross-react with, and mount an immune response against, non-self hematopoietic stem cells.

13 Claims, 9 Drawing Sheets

Specification includes a Sequence Listing.

(56) References Cited

U.S. PATENT DOCUMENTS

| | | |
|---|---|---|
| 5,475,092 A | 12/1995 | Chari et al. |
| 5,530,101 A | 6/1996 | Queen et al. |
| 5,545,806 A | 8/1996 | Lonberg et al. |
| 5,569,825 A | 10/1996 | Lonberg et al. |
| 5,585,089 A | 12/1996 | Queen et al. |
| 5,585,499 A | 12/1996 | Chari et al. |
| 5,621,002 A | 4/1997 | Bosslet et al. |
| 5,621,083 A | 4/1997 | Better et al. |
| 5,622,929 A | 4/1997 | Willner et al. |
| 5,625,126 A | 4/1997 | Lonberg et al. |
| 5,633,425 A | 5/1997 | Lonberg et al. |
| 5,635,483 A | 6/1997 | Pettit et al. |
| 5,648,237 A | 7/1997 | Carter |
| 5,661,016 A | 8/1997 | Lonberg et al. |
| 5,663,149 A | 9/1997 | Pettit et al. |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kuntsmann et al. |
| 5,730,979 A | 3/1998 | Bazin et al. |
| 5,739,116 A | 4/1998 | Hamann et al. |
| 5,744,580 A | 4/1998 | Better et al. |
| 5,756,699 A | 5/1998 | Better et al. |
| 5,766,886 A | 6/1998 | Studnicka et al. |
| 5,767,285 A | 6/1998 | Hamann et al. |
| 5,770,196 A * | 6/1998 | Studnicka ................ A61P 17/06 424/134.1 |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,795,572 A | 8/1998 | Diegel et al. |
| 5,807,734 A | 9/1998 | Diegel et al. |
| 5,814,318 A | 9/1998 | Lonberg et al. |
| 5,817,311 A | 10/1998 | Bazin et al. |
| 5,821,123 A | 10/1998 | Studnicka |
| 5,824,805 A | 10/1998 | King et al. |
| 5,837,491 A | 11/1998 | Better et al. |
| 5,840,523 A | 11/1998 | Simmons et al. |
| 5,846,545 A | 12/1998 | Chari et al. |
| 5,869,619 A * | 2/1999 | Studnicka .......... C07K 16/2866 530/387.3 |
| 5,877,296 A | 3/1999 | Hamann et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,951,983 A | 9/1999 | Bazin et al. |
| 6,010,902 A | 1/2000 | Ledbetter et al. |
| 6,054,297 A | 4/2000 | Carter et al. |
| 6,146,631 A | 11/2000 | Better et al. |
| 6,146,850 A | 11/2000 | Better et al. |
| 6,162,432 A | 12/2000 | Wallner et al. |
| 6,180,370 B1 | 1/2001 | Queen et al. |
| 6,214,345 B1 | 4/2001 | Firestone et al. |
| 6,218,519 B1 | 4/2001 | Kenten et al. |
| 6,268,488 B1 | 7/2001 | Barbas, III et al. |
| 6,333,410 B1 | 12/2001 | Chari et al. |
| 6,376,217 B1 | 4/2002 | Better et al. |
| 6,441,163 B1 | 8/2002 | Chari et al. |
| 6,541,611 B1 | 4/2003 | Bazin et al. |
| 6,558,662 B2 | 5/2003 | Sykes et al. |
| 6,649,742 B1 | 11/2003 | Better et al. |
| 6,677,435 B2 | 1/2004 | Barbas, III et al. |
| 6,716,821 B2 | 4/2004 | Zhao et al. |
| 6,759,509 B1 | 7/2004 | King et al. |
| 6,764,688 B2 | 7/2004 | Yamashita et al. |
| 6,835,807 B1 | 12/2004 | Susaki et al. |
| 6,849,258 B1 | 2/2005 | Bazin et al. |
| 7,115,259 B2 | 10/2006 | Horwitz |
| 7,153,932 B2 | 12/2006 | Better et al. |
| 7,192,736 B2 | 3/2007 | McDonald et al. |
| 7,223,837 B2 | 5/2007 | De Groot et al. |
| 7,250,167 B2 | 7/2007 | Bazin et al. |
| 7,276,497 B2 | 10/2007 | Chari et al. |
| 7,332,157 B2 | 2/2008 | Sykes |
| 7,368,565 B2 | 5/2008 | Chari et al. |
| 7,408,039 B2 | 8/2008 | Sykes et al. |
| 7,473,796 B2 | 1/2009 | Chari et al. |
| 7,521,541 B2 | 4/2009 | Eigenbrot et al. |
| 7,592,006 B1 | 9/2009 | Bazin et al. |
| 7,638,121 B2 | 12/2009 | Sykes |
| 7,754,681 B2 | 7/2010 | Feng |
| 7,939,062 B2 | 5/2011 | Sykes |
| 8,236,319 B2 | 8/2012 | Chari et al. |
| 8,679,500 B2 | 3/2014 | Boumsell et al. |
| 9,233,173 B2 | 1/2016 | Faulstich et al. |
| 9,399,681 B2 | 7/2016 | Anderl et al. |
| 9,504,756 B2 | 11/2016 | Lyon et al. |
| 9,636,421 B2 | 5/2017 | Verkade et al. |
| 9,676,702 B2 | 6/2017 | Lutz et al. |
| 10,072,091 B2 | 9/2018 | Weissman et al. |
| 10,842,882 B2 | 11/2020 | Anderl et al. |
| 2002/0051784 A1 | 5/2002 | Boussiotis et al. |
| 2003/0096743 A1 | 5/2003 | Senter et al. |
| 2003/0130189 A1 | 7/2003 | Senter et al. |
| 2004/0018194 A1 | 1/2004 | Francisco et al. |
| 2004/0052793 A1 | 3/2004 | Carter et al. |
| 2004/0121940 A1 | 6/2004 | De Groot et al. |
| 2004/0265315 A1 | 12/2004 | Dingivan et al. |
| 2005/0169933 A1 | 8/2005 | Steeves et al. |
| 2005/0238649 A1 | 10/2005 | Doronina et al. |
| 2005/0256030 A1 | 11/2005 | Feng |
| 2006/0051355 A1 | 3/2006 | van Oosterhout et al. |
| 2006/0084107 A1 | 4/2006 | Wallner et al. |
| 2008/0245027 A1 | 10/2008 | Lambertini |
| 2008/0254027 A1* | 10/2008 | Bernett .................... A61P 35/02 435/375 |
| 2011/0091453 A1 | 4/2011 | Dingivan |
| 2011/0250203 A1 | 10/2011 | Klitgaard et al. |
| 2011/0280868 A1 | 11/2011 | Dingivan et al. |
| 2012/0045435 A1* | 2/2012 | Deisher .................... A61K 35/28 435/375 |
| 2012/0121598 A1 | 5/2012 | Boumsell et al. |
| 2012/0213805 A1 | 8/2012 | Faulstich et al. |
| 2013/0183322 A1 | 7/2013 | Reisner et al. |
| 2014/0294865 A1 | 10/2014 | Simon et al. |
| 2014/0369974 A1 | 12/2014 | Reisner et al. |
| 2015/0004145 A1 | 1/2015 | Lemischka et al. |
| 2015/0079114 A1 | 3/2015 | Ohtsuka et al. |
| 2015/0218220 A1 | 8/2015 | Mendelsohn et al. |
| 2016/0002298 A1 | 1/2016 | Müller et al. |
| 2016/0089450 A1 | 3/2016 | Faulstich et al. |
| 2016/0120947 A1 | 5/2016 | Scadden et al. |
| 2016/0303254 A1 | 10/2016 | Kolakowski et al. |
| 2016/0324982 A1 | 11/2016 | Scadden et al. |
| 2017/0080102 A1 | 3/2017 | Whiteman et al. |
| 2017/0129128 A1 | 5/2017 | Mortaro et al. |
| 2017/0298145 A1 | 10/2017 | Verkade et al. |
| 2017/0360954 A1* | 12/2017 | Nixon ................ A61K 47/6803 |
| 2018/0289832 A1 | 10/2018 | Hartigan et al. |
| 2018/0346876 A1 | 12/2018 | Xiao et al. |
| 2019/0100593 A1 | 4/2019 | Scadden et al. |
| 2019/0134217 A1 | 5/2019 | Nixon et al. |
| 2019/0314411 A1 | 10/2019 | Xiao et al. |

FOREIGN PATENT DOCUMENTS

| | | |
|---|---|---|
| EP | 0 527 839 | 12/1998 |
| EP | 0 589 877 | 10/2005 |
| EP | 1 661 584 | 5/2006 |
| EP | 1 859 811 | 11/2007 |
| EP | 2 416 805 | 10/2010 |
| WO | 89/06968 | 8/1989 |
| WO | 92/01047 | 1/1992 |
| WO | 92/14491 | 9/1992 |
| WO | 92/16563 | 10/1992 |
| WO | 94/20619 | 9/1994 |
| WO | 94/23747 | 10/1994 |
| WO | 96/33735 | 10/1996 |
| WO | 96/34096 | 10/1996 |
| WO | 96/41608 | 12/1996 |
| WO | 98/13059 | 4/1998 |
| WO | 98/24893 | 6/1998 |

(56) References Cited

FOREIGN PATENT DOCUMENTS

| WO | 99/03502 | 1/1999 | | |
|---|---|---|---|---|
| WO | 02/088172 | 11/2002 | | |
| WO | 2004/032828 | 4/2004 | | |
| WO | 2005/026210 | 3/2005 | | |
| WO | 2005/037992 | 4/2005 | | |
| WO | 2005/081711 | 9/2005 | | |
| WO | 2006/034488 | 3/2006 | | |
| WO | WO-2008121160 | A2 * | 10/2008 | ............ A61P 35/02 |
| WO | 2010/022737 | 3/2010 | | |
| WO | 2010/115630 | 10/2010 | | |
| WO | WO-2010115629 | A2 * | 10/2010 | ........ A61K 47/6831 |
| WO | 2010/145895 | 12/2010 | | |
| WO | 2014/083505 | 6/2014 | | |
| WO | 2014/151030 | 9/2014 | | |
| WO | WO-2016071856 | A1 * | 5/2016 | ............ C07K 16/22 |
| WO | WO-2016142049 | A1 * | 9/2016 | ............ A61K 38/12 |
| WO | 2016/164502 | 10/2016 | | |
| WO | 2016/172606 | 10/2016 | | |
| WO | 2017/004026 | 1/2017 | | |
| WO | 2017/046658 | 3/2017 | | |
| WO | 2017/089607 | 6/2017 | | |
| WO | 2017/149077 | 9/2017 | | |
| WO | 2017/191579 | 11/2017 | | |
| WO | 2017/219025 | 12/2017 | | |
| WO | 2018/115466 | 6/2018 | | |
| WO | 2018/134787 | 7/2018 | | |
| WO | 2019/030171 | 2/2019 | | |
| WO | 2019/084064 | 5/2019 | | |
| WO | 2019/108863 | 6/2019 | | |
| WO | 2020/023561 | 1/2020 | | |

OTHER PUBLICATIONS

Bird et al., "Single-Chain Antigen-Binding Proteins", Science, vol. 242, Oct. 21, 1988, pp. 423-426.
Bose et al., "Rational Design of a Highly Efficient Irreversible DNA Interstrand Cross-Linking Agent Based on the Pyrrolobenzodiazepine Ring System", J. Am. Chem. Soc., vol. 114, No. 12, 1992, pp. 4939-4941.
Branco et al., "Selective Deletion of Antigen-Specific, Activated T Cells by a Humanized MAB to CD2 (MEDI-507) is Mediated by NK Cells", Transplantation, vol. 68, No. 10, Nov. 27, 1999, pp. 1588-1596.
Bradley A. Katz, "Structural and Mechanistic Determinants of Affinity and Specificity of Ligands Discovered or Engineered by Phage Display", Annu. Rev. Biophys. Biomol. Struct., vol. 26, 1997, pp. 27-45.
Brian K. Kay, "Biologically displayed random peptides as reagents in mapping protein-protein interactions", Perspectives in Drug Discovery and Design, vol. 2, Mar. 9, 1995, pp. 251-268.
Byers et al., "Use of an Anti-Pan T-Lymphocyte Ricin A Chain Immunotoxin in Steroid-Resistant Acute Graft-Versus-Host Disease", Blood, vol. 75, No. 7, Apr. 1, 1990, pp. 1426-1432.
Carl et al., "A Novel Connector Linkage Applicable in Prodrug Design", Journal of Medicinal Chemistry, vol. 24, No. 5, May 1981, pp. 479-480.
Chakravarty et al., "Plasmin-Activated Prodrugs for Cancer Chemotherapy. 2. Synthesis and Biological Activity of Peptidyl Derivatives of Doxorubicin", J. Med. Chem., vol. 26, No. 5, 1983, pp. 638-644.
Chari et al., "Immunoconjugates Containing Novel Maytansinoids: Promising Anticancer Drugs", Cancer Research, vol. 52, Jan. 1, 1992, pp. 127-131.
Chiswell et al., "Phage antibodies: will new 'coliclonal' antibodies replace monoclonal antibodies?", Trends Biotechnol., vol. 10, Mar. 1992, pp. 80-84.
Clackson et al., "Making antibody fragments using phage display libraries", Nature, vol. 352, Aug. 15, 1991, pp. 624-628.
Cox et al., "A directory of human germ-line Vx segments reveals a strong bias in their usage", Eur. J. Immunol., vol. 24, 1994, pp. 827-836.

Dall'Acqua et al., "Properties of Human IgG1s Engineered for Enhanced Binding to the Neonatal Fc Receptor (FcRn)", The Journal of Biological Chemistry, vol. 281, No. 33, Aug. 18, 2006, pp. 23514-23524.
Datta-Mannan et al., "Humanized $IgG_1$ Variants with Differential Binding Properties to the Neonatal Fc Receptor: Relationship to Pharmacokinetics in Mice and Primates", Drug Metabolism and Disposition, vol. 35, No. 1, Oct. 11, 2006, pp. 86-94.
De Groot et al., "Elongated Multiple Electronic Cascade and Cyclization Spacer Systems in Activatible Anticancer Prodrugs for Enhanced Drug Release", J. Org. Chem., vol. 66, No. 26, Jul. 3, 2001, pp. 8815-8830.
Doronina et al., "Development of potent monoclonal antibody auristatin conjugates for cancer therapy", Nature Biotechnology, vol. 21, No. 7, Jul. 2003, pp. 778-784.
Doronina et al., "Enhanced Activity of Monomethylauristatin F through Monoclonal Antibody Delivery: Effects of Linker Technology on Efficacy and Toxicity", Bioconjugate Chem., vol. 17, No. 1, 2006, pp. 114-124.
Dubowchik et al., "Receptor-mediated and enzyme-dependent targeting of cytotoxic anticancer drugs", Pharmacology & Therapeutics, vol. 83, 1999, pp. 67-123.
Extended European Search Report dated Oct. 12, 2021, in EP 18883067.3, 9 pages.
Extended European Search Report dated Jan. 26, 2024, in EP 20818567.8, 16 pages.
Felici et al., "Peptide and protein display on the surface of filamentous Bacteriophage", Biotechnology Annual Review, vol. 1, 1995, pp. 149-183.
Graham et al., "Characteristics of a Human Cell Line Transformed by DNA from Human Adenovirus Type 5", J. Gen Virol., vol. 36, Feb. 10, 1977, pp. 59-72.
Gregson et al., "Design, Synthesis, and Evaluation of a Novel Pyrrolobenzodiazepine DNA-Interactive Agent with Highly Efficient Cross-Linking Ability and Potent Cytotoxicity", J. Med. Chem., vol. 44, No. 5, 2001, pp. 737-748.
Greg T. Hermanson, "Bioconjugate Techniques" Second Edition, Academic Press: New York, Homobifunctional Crosslinkers, 2013, pp. 234-242.
Gu et al., "Generation of Dual-Variable-Domain Immunoglobulin Molecules for Dual-Specific Targeting", Methods in Enzymology, vol. 502, 2012, pp. 25-41.
Hay et al., "A 2-Nitroimidazole Carbamate Prodrug of 5-Amino-1-(Chloromethyl)-3-[(5,6,7-Trimethoxyindol-2-YL)Carbonyl]-1,2-Dihydro-3H-Benze[E]Indole (AMINO-SECO-CBI-TMI) For Use With Debt and GDEPT", Bioorg. Med. Chem. Lett., vol. 9, Jun. 25, 1999, pp. 2237-2242.
Henslee et al., "A New Approach to the Prevention of Graft-Versus-Host Disease Using XomaZyme-H65 Following Histo-incompatible Partially T-depleted Marrow Grafts", Transplantation Proceedings, vol. 21, No. 1, Feb. 1989, pp. 3004-3007.
Henslee-Downey et al., "Combined in vitro T Lymphocyte Depletion for the control of Graft-Versus-Host disease Following Haploidentical Marrow Transplant", Transplantation, vol. 61, No. 5, Mar. 15, 1996, pp. 1-17.
Hinman et al., "Preparation and Characterization of Monoclonal Antibody Conjugates of the Calicheamicins: A Novel and Potent Family of Antitumor Antibiotics", Cancer Research, vol. 53, Jul. 15, 1993, pp. 3336-3342.
Hinton et al., "Engineered Human IgG Antibodies with Longer Serum Half-Lives in Primates", The Journal of Biological Chemistry, vol. 279, No. 8, Feb. 20, 2004, pp. 6213-6216.
Hinton et al., "An Engineered Human IgG1 Antibody with Longer Seru Half-Life", J. Immunol., vol. 176, No. 1, Jan. 1, 2006, pp. 346-356.
Hirahara et al., "$CD4^+$ T-cell subsets in inflammatory diseases: beyond the $T_h1/T_h2$ paradigm", International Immunology, vol. 28, No. 4, Feb. 12, 2016, pp. 163-171.
Holliger et al., ""Diabodies": Small bivalent and bispecific antibody fragments", Proc. Natl. Acad. Sci. USA, vol. 90, Jul. 1993, pp. 6444-6448.
Hoogenboom et al., "Antibody phage display technology and its applications", Immunotechnology, vol. 4, Feb. 13, 1998, pp. 1-20.

(56) References Cited

OTHER PUBLICATIONS

Huston et al., "Protein engineering of antibody binding sites: Recovery of specific Activity in an anti-digoxin single-chain Fv analogue produced in *Escherichia coli*", Proc. Natl. Acad. Sci. USA, vol. 85, Aug. 1988, pp 5879-5883.
International Search Report received for PCT/US2018/063175, dated Apr. 26, 2019, 6 pages.
International Search Report received for PCT/US2020/036494, dated Sep. 21, 2020, 4 pages.
Jain et al., "Current ADC Linker Chemistry", Pharm. Res., vol. 32, Mar. 11, 2015, pp. 3526-3540.
Jennie P. Mather, "Establishment and Characterization of Two Distinct Mouse Testicular Epithelial Cell Lines", Biology of Reproduction, vol. 23, Apr. 29, 1980, pp. 243-252.
Jones et al., "Isolation of complementary DNA clones encoding the human lymphocyte glycoprotein T1/Leu-1", Nature, vol. 323, Sep. 25, 1986, pp. 346-349.
Kay et al., "High-throughput screening strategies to identify inhibitors of protein-protein interactions", Molecular Diversity, vol. 1, 1995, pp. 139-140.
Keith A. Charlton, "Expression and Isolation of Recombinant Antibody Fragments in *E. coli*", Antibody Engineering Methods and Protocols, Methods in Molecular Biology™, (Benny K. C. Lo, ed., Human Press, Totowa, N.J.), vol. 248, 2004, pp. 245-254.
Kim et al., "Mapping the site on human IgG for binding of the MHC class I-related receptor, FcRn", Eur. J. Immunol., vol. 29, Sep. 6, 1999, pp. 2819-2825.
Kostelny et al., "Formation of A Bispecific Antibody by the use of Leucin Zippers", The Journal of Immunology, vol. 148, No. 5, Mar. 1, 1992, pp. 1547-1553.
Laguzza et al., "New Antitumor Monoclonal Antibody-Vinca Conjugates LY203725 and Related Compounds: Design, Preparation, and Representative in Vivo Activity", J. Med. Chem., vol. 32, No. 3, 1989, pp. 548-555.
Leriche et al., "Cleavable linkers in chemical biology", Bioorganic & Medicinal Chemistry, vol. 20, 2012, pp. 571-582.
Liu et al., "New Produces for Preparation and Isolation of Conjugates of Proteins and a Synthetic Copolymer of D-Amino Acids and Immunochemical characterization of Such Conjugates", Biochemistry, vol. 18, No. 4, 1979, pp. 690-697.
Lode et al., "Targeted Therapy with a Novel Enediyne Antibiotic Calicheamicin $\theta^<_1$, Effectively Suppresses Growth and Dissemination of Liver Metastases in a Syngenic Model of Murine Neuroblastoma", Cancer Research, vol. 58, Jul. 15, 1998, pp. 2925-2928.
Manske et al., "Antigenic Modulation by Anti-Cd5 Immunotoxins", The Journal of Immunology, vol. 136, No. 12, Jun. 15, 1986, pp. 4721-4728.
Maher et al., "Culture of Testicular Cells in Hormone-Supplemented Serum-Free Medium", Annals N.Y. Acad. Sci., vol. 383, 1982, pp. 44-68.
McCafferty et al., "Phage antibodies: filamentous phage displaying antibody variable domains", Nature, vol. 348, Dec. 6, 1990, pp. 552-554.
Miller et al., "A New Class of Antibody-Drug Conjugates with Potent DNA Alkylating Activity", Mol. Cancer Ther., vol. 15, No. 8, Aug. 2016, pp. 1870-1878.
Miller et al., "Monoclonal Antibody Therapeutic Trials in Seven Patients With T-Cell Lymphoma", Blood, vol. 62, No. 5, Nov. 1983, pp. 988-995.
Neville, Jr. et al., "Enhancement of Immunotoxin Efficacy by Acid-cleavable Cross-linking Agents Utilizing Diphtheria Toxin and Toxin Mutants", The Journal of Biological Chemistry, vol. 264, No. 25, Mar. 30, 1989, pp. 14653-14661.
N. R. Bachur, "Free Radical Damage", Anthracycline Antibiotics in Cancer Therapy, 1982, pp. 97-102.
Paul Polakis, "Antibody Drug Conjugates for Cancer Therapy", Pharmacol. Rev., vol. 68, Jan. 2016, pp. 3-19.

Peterson et al., "Transport and Storage of Anthracycline in Experimental Systems and Human Leukemia" in *Anthracycline Antibiotics in Cancer Therapy*, Sep. 16-18, 1981, pp. 132-146.
Petkova et al., "Enhanced half-life of genetically engineered human IgG1 antibodies in a humanized FcRn mouse model: potential application in humorally mediated autoimmune disease", International Immunology, vol. 18, No. 12, Oct. 31, 2006, pp. 1759-1769.
Pettit et al., "The Absolute Configuration and Synthesis of Natural (−)-Dolastatin 101", J. Am. Chem. Soc., vol. 111, No. 14, 1989, pp. 5463-5465.
Pettit et al., "Dolastatins 24. Synthesis of (−)-dolastatin 10.1 X-Ray molecular structure of N,N-dimethylvalyl-valyl-dolaisoleuine tert-butyl ester", J. Chem. Soc. Perkin Trans., vol. 1, 1996, pp. 859-863.
Pettit et al., "Antineoplastic agents 365. Dolastatin 10 SAR probes", Anti-Cancer Drug Design, vol. 13, Sep. 3, 1997, pp. 243-277.
Pettit et al., "Specific Activities of Dolastatin 10 and Peptide Derivatives against *Cryptococcus neoformans*", Antimicrobial Agents and Chemotherapy, vol. 42, No. 11, Nov. 1998, pp. 2961-2965.
Pettit et al., "The Dolastatins; 18: Stereospecific Synthesis of Dolaproine", Synthesis, Jun. 1996, pp. 719-725.
Przepiorka et al., "Evaluation of anti-CD5 ricin A chain immunoconjugate for prevention of acute graft-vs.-host disease after HLA-identical marrow transplantation", Therapeutic Immunology, vol. 1, 1994, pp. 77-82.
Quintieri et al., "Formation and Antitumor Activity of PNU-159682, A Major Metabolite of Nemorubicin in Human Liver Microsomes", Clinical Cancer Research, vol. 11, Feb. 15, 2005, pp. 1608-1617.
Raphael et al., "T cell subsets and their signature cytokines in autoimmune and inflammatory diseases", Cytokine, vol. 74, No. 1, Jul. 2015, pp. 5-17.
Riechmann et al., "Reshaping human antibodies for therapy", Nature, vol. 332, Mar. 24, 1988, pp. 323-327.
Royston et al., "Human T Cell Antigens defined by Monoclonal Antibodies: the 65,000-Dalton Antigen of T Cells (T65) is also found on Chronic Lymphocytic Leukemia Cells bearing surface immunoglobulin1", The Journal of Immunology, vol. 125, No. 2, Aug. 1980, pp. 725-731.
Seed et al., "Molecular cloning of the CD2 antigen, the T-cell erythrocyte receptor, by a rapid immunoselection procedure", Proc. Natl. Acad. Sci. USA, vol. 84, May 1987, pp. 3365-3369.
Sessa et al., "Ongoing phase I and II studies of novel anthracyclines", Cardiovasc. Toxicol., vol. 7, May 22, 2007, pp. 75-79.
Sewell et al., "Molecular cloning of the human T-lymphocyte surface CD2 (T11) antigen", Proc. Natl. Acad. Sci. USA, vol. 83, Nov. 1986, pp. 8718-8722.
Shawler et al., "Induction of in Vitro and in Vivo Antigenic Modulation by the Anti-Human T-Cell Monoclonal Antibody T101", Cancer Research, vol. 44, Dec. 1984, pp. 5921-5927.
Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, vol. 276, No. 9, Mar. 2, 2001, pp. 6591-6604.
Sondermann et al., "The 3.2-Å crystal structure of the human IgG1 Fc fragment-FcγRIII complex", Nature, vol. 406, Jul. 20, 2000, pp. 267-273.
Songsivilai et al., "Bispecific antibody: a tool for diagnosis and treatment of disease", Clin. Exp. Immunol., vol. 79, 1990, pp. 315-321.
Sullivan et al., "Bone Marrow Transplantation for Non-Malignant Disease", American Society of Hematology, 2000, pp. 319-338.
Sun et al., "Overview of Orchestration of CD4+ T Cell Subsets in Immune Responses", Adv. Exp. Med. Biol., vol. 841, 2014, pp. 1-13.
Sussman et al., "Engineered cysteine antibodies: an improved antibody-drug conjugate platform with a novel mechanism of drug-linker stability", Protein Engineering, Design & Selection, vol. 31, No. 2, Jan. 23, 2018, pp. 47-54.
Sutherland et al., "SGN-CD33A: a novel CD33-targeting antibody-drug conjugate using a pyrrolobenzodiazepine dimer is active in models of drug-resistant AML", Blood, vol. 122, No. 8, Aug. 22, 2013, pp. 1455-1463.

(56) References Cited

OTHER PUBLICATIONS

Thorpe et al., "New Coupling Agents for the Synthesis of Immunotoxins Containing a Hindered Disulfide Bond with Improved Stability in Vivo", Cancer Research, vol. 47, Nov. 15, 1987, pp. 5924-5931.

Urlaub et al., "Isolation of Chinese hamster cell mutants deficient in dihydrofolate Reductase activity", Proc. Natl. Acad. Sci. USA, vol. 77, No. 7, Jul. 1980, pp. 4216-4220.

Vaccaro et al., "Engineering the Fc region of immunoglobulin G to modulate in vivo antibody levels", Nature Biotechnology, vol. 23, No. 10, Oct. 2005, pp. 1283-1288.

Ward et al., "Binding activities of a repertoire of single immunoglobulin variable domains secreted from *Escherichia coli*", Nature, vol. 341, Oct. 12, 1989, pp. 544-546.

Werner-Favre et al., "Cell surface antigen CD5 is a marker for activated human B cells", Eur. J. Immunol., vol. 19, 1989, pp. 1209-1213.

Williams et al., "Cell-based selection of internalizing fully human antagonistic antibodies directed against FLT3 for suppression of leukemia cell growth", Leukemia, vol. 19, Jun. 2, 2005, pp. 1432-1438.

Woyke et al., "In Vitro Activities and Postantifungal Effects of the Potent Dolastatin 10 Derivative Auristatin PHE", Antimicrobial Agents and Chemotherapy, vol. 45, No. 12, Dec. 2001, pp. 3580-3584.

Written Opinion dated Apr. 26, 2019, in PCT/US2018/063175, 12 pages.

Written Opinion dated Sep. 21, 2020, in PCT/US2020/036494, 5 pages.

Yazaki et al., "Expressions of Recombinant Antibodies in Mammalian Cell lines", Antibody Engineering Methods and Protocols, Methods in Molecular Biology, vol. 248, 2004, pp. 255-268.

Yeung et al., "A Therapeutic Anti-VEGF Antibody with Increased Potency Independent of Pharmacokinetic Half-life", Cancer Research, vol. 70, No. 8, Apr. 15, 2010, pp. 3269-3277.

Zalevsky et al., "Enhanced antibody half-life improves in vivo activity", Nat. Biotechnol., vol. 28, No. 2, Feb. 2010, pp. 157-159.

Zambrano-Zaragoza et al., "Th17 Cells in Autoimmune and Infectious Diseases", International Journal of Inflammation, Article ID 651503, Aug. 3, 2014, pp. 1-12.

Zanotti et al., "Synthesis of analogues of amaninamide, an amatoxin from the white Amanita virosa mushroom", Int. J. Peptide Protein Res., vol. 30, Jan. 30, 1987, pp. 450-459.

U.S. Appl. No. 17/457,607, filed Dec. 3, 2021, Patent Publication No. 2022/0249683, Boitano et al.

\* cited by examiner

COMPOSITIONS AND METHODS FOR THE DEPLETION OF CD5+ CELLS

RELATED APPLICATIONS

This application is a continuation of U.S. patent application Ser. No. 16/851,082, filed on Apr. 16, 2020, which is a continuation of International Patent Appln. No. PCT/US2018/063175, filed on Nov. 29, 2018, which claims the benefit of priority to U.S. Provisional Patent Appln. No. 62/592,214, filed on Nov. 29, 2017. The contents of the aforementioned applications are incorporated by reference herein in their entirety.

SEQUENCE LISTING

The instant application contains a Sequence Listing that has been submitted electronically in ASCII format and is hereby incorporated by reference in its entirety. Said ASCII copy, created on Apr. 29, 2021, is named M103034_1060US_C2_SL.txt and is 71,718 bytes in size.

BACKGROUND OF THE INVENTION

Despite advances in the medicinal arts, there remains a demand for treating pathologies of the hematopoietic system, such as diseases of a particular blood cell, metabolic disorders, cancers, and autoimmune conditions, among others. While hematopoietic stem cells have significant therapeutic potential, a limitation that has hindered their use in the clinic has been the difficulty associated with ensuring engraftment of hematopoietic stem cell transplants in a host. A patient's own immune system often attacks the transplanted cells and mediates rejection of the transplanted hematopoietic stem cells. In order to avoid rejection, a patient is treated with immune system destroying agents prior to hematopoietic stem cell transplantation, e.g., chemotherapeutic agents or radiation. Unfortunately, efforts to induce tolerance of the hematopoietic stem cell transplantation in the patient often result in serious complications. Thus, there is a need for new compositions and methods to improve hematopoietic stem cell transplantation.

SUMMARY OF THE INVENTION

There is currently a need for compositions and methods for treating disorders of the hematopoietic system, such as autoimmune disorders, as well as compositions and methods for promoting the engraftment of exogenous hematopoietic stem cell grafts such that the multi-potency and hematopoietic functionality of these cells is preserved following transplantation. In one aspect, the present invention provides compositions and methods for the direct treatment of various disorders of the hematopoietic system, metabolic disorders, cancers, and autoimmune diseases, among others. The compositions and methods disclosed herein target immune cells for conditioning a human patient for a hematopoietic stem cell transplantation for treatment of a disease such as, but not limited to, blood cancer or an autoimmune disease.

In another aspect, the invention additionally features compositions and methods for conditioning a patient, such as a human patient, prior to receiving hematopoietic stem cell transplant therapy so as to promote the engraftment of hematopoietic stem cell grafts. The patient may be one that is suffering from an autoimmune disease or one or more blood disorders, such as cancer, hemoglobinopathy, or other hematopoietic pathology, and is thus in need of hematopoietic stem cell transplantation. As described herein, hematopoietic stem cells are capable of differentiating into a multitude of cell types in the hematopoietic lineage, and can be administered to a patient in order to populate or repopulate a cell type that is deficient in the patient. In certain aspects, the invention features antibodies and antibody-drug conjugates capable of binding CD5, as well as methods of administering the same to a patient so as to (i) directly treat a blood disorder, such as an autoimmune disease, by selectively depleting a population of immune cells that express CD5, such as an autoreactive T cell, B cell, or natural killer (NK) cell, and/or to (ii) deplete a population of T cells, B cells, or NK cells prior to administration of a hematopoietic stem cell transplant to the patient, thereby reducing the likelihood of hematopoietic stem cell graft rejection. The former activity enables the direct treatment of a wide range of autoimmune disorders, as CD5 may be expressed by a T cell, B cell, or NK cell that cross-reacts with, and mounts an inappropriate immune response against, a self antigen. Administration of an anti-CD5 antibody, antigen-binding fragment thereof, or an antibody-drug conjugate to a patient in this case can cause depletion of a population of CD5+ autoimmune cells, such as T cells, B cells, or NK cells that cross-react with one or more self antigens, thereby treating the autoimmune pathology. The latter activity facilitates the generation of an environment that is conducive to hematopoietic stem cell engraftment, as T cells. B cells, and/or NK cells that cross-react with one or more non-self antigens expressed by a hematopoietic stem cell, such as one or more non-self MHC antigens expressed by a hematopoietic stem cell, can mount an immune response against transplanted hematopoietic stem cells and thus promote graft rejection. In this latter case, patients suffering from a disorder such as cancer, an autoimmune disease, or other condition of the hematopoietic system can subsequently be administered a hematopoietic stem cell transplant in order, for instance, to repopulate one or more blood cell lineages that are defective or depleted in the patient. In one aspect, the invention thus provides methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, as well as cancers and autoimmune diseases, among others.

In one aspect, the invention provides a method of depleting a population of CD5+ cells, for instance, in a human patient, such as a population of CD5+ T cells, CD5+ B cells, and/or CD5+ NK cells in a human patient, by administering to the patient an effective amount of an antibody, antigen-binding fragment thereof, or antibody-drug conjugate that binds to CD5.

In another aspect, the invention provides a method of depleting a population of CD5+ cells in a human patient in need of a hematopoietic stem cell transplant, such as a population of CD5+ T cells, CD5+ B cells, and/or CD5+ NK cells in a human patient in need of hematopoietic stem cell transplant, by administering to the patient an effective amount of an antibody, antigen-binding fragment thereof, or antibody-drug conjugate that binds to CD5, for example, prior to the patient receiving a transplant including hematopoietic stem cells.

In an additional aspect, the invention provides a method of preventing or reducing the likelihood of rejection of a hematopoietic stem cell graft in a human patient in need of hematopoietic stem cell transplant therapy by administering, prior to the patient receiving a transplant including hematopoietic stem cells, an effective amount of an antibody, antigen-binding fragment thereof, or antibody-drug conjugate that binds to CD5.

In another aspect, the invention provides a method of depleting a population of endogenous T cells in a human patient in need of hematopoietic stem cell transplant therapy by administering, prior to the patient receiving a transplant including hematopoietic stem cells, an effective amount of an antibody, antigen-binding fragment thereof, or antibody-drug conjugate that binds to CD5.

In another aspect, the invention features a method, for example, of treating a human patient in need of a hematopoietic stem cell transplant, including administering to a human patient a transplant including hematopoietic stem cells, wherein the patient has been previously administered an antibody or antigen-binding fragment thereof that binds to CD5. The antibody, antigen-binding fragment thereof, or antibody-drug conjugate may be administered to the patient in an amount sufficient to deplete a population of CD5+ cells in the patient, such as a population of CD5+ T cells, CD5+ B cells, and/or CD5+ NK cells in the human patient.

In an additional aspect, the invention features a method, for example, of treating a human patient in need of a hematopoietic stem cell transplant, including: administering to a human patient an antibody, antigen-binding fragment thereof, or antibody-drug conjugate that binds to CD5 in an amount sufficient to deplete a population of CD5+ cells in the patient, such as a population of CD5+ T cells, CD5+ B cells, and/or CD5+ NK cells in the patient, and subsequently administering to the patient a transplant including hematopoietic stem cells.

In some embodiments of any of the above aspects, the antibody or antigen-binding fragment thereof is produced by the hybridoma cell line ATCC CRL 8000. In some embodiments, the antibody or antigen-binding fragment thereof competitively inhibits the binding of CD5 to an antibody or antigen-binding fragment thereof produced by the hybridoma cell line ATCC CRL 8000.

In some embodiments of any of the above aspects, the antibody or antigen-binding fragment thereof comprises the following variable domains:

```
a V_L having the amino acid sequence
                                         (SEQ ID NO: 1)
DIQMTQSPSSMSASLGDRVTITCRASQDINSYLSWFQQKPGKSPKTLIYR

ANRLVDGVPSRFSGSGSGTDYTLTISSLQYEDFGIYYCQQYDESPWTFGG

GTKLEIK;
and a V_H having the amino acid sequence
                                         (SEQ ID NO: 2)
QIQLVQSGPGLKKPGGSVRISCAASGYTFTNYGMNWVKQAPGKGLRWMGW

INTHTGEPTYADDFKGRFTFSLDTSKSTAYLQINSLRAEDTATYFCTRRG

YDWYFDVWGQGTTVTSS.
```

In some embodiments, the antibody or antigen-binding fragment thereof competitively inhibits the binding of CD5 to an antibody or antigen-binding fragment thereof that comprises the foregoing variable domains.

In some embodiments of any of the above aspects, the antibody or antigen-binding fragment thereof includes the following CDRs:

a CDR-H1 having the amino acid sequence GYTFTNY (SEQ ID NO: 3);
a CDR-H2 having the amino acid sequence NTHTGE (SEQ ID NO: 4);
a CDR-H3 having the amino acid sequence RGYDWYFDV (SEQ ID NO: 5);
a CDR-L1 having the amino acid sequence RASQDINSYLS (SEQ ID NO: 6);
a CDR-L2 having the amino acid sequence RANRLVD (SEQ ID NO: 7); and
a CDR-L3 having the amino acid sequence QQYDESPWT (SEQ ID NO: 8).

In some embodiments, the antibody or antigen-binding fragment thereof competitively inhibits the binding of CD5 to an antibody or antigen-binding fragment thereof that comprises the foregoing CDRs.

In some embodiments of any of the above aspects, the antibody or antigen-binding fragment thereof comprises the following variable domains:

```
a V_L having the amino acid sequence
                                         (SEQ ID NO: 9)
DIQMTQSPSSLSASVGDRVTITCRASQDINSYLSWFQQKPGKAPKTLIYR

ANRLESGVPSRFSGSGSGTDYTLTIS SLQYEDFGIYYCQQYDESPWTFG

GGTKLEIK;
and a V_H having the amino acid sequence
                                         (SEQ ID NO: 10)
EIQLVQSGGGLVKPGGSVRISCAASGYTFTNYGMNWVRQAPGKGLEWMGW

INTHYGEPTYADSFKGTRTFSLDDSKNTAYLQINSLRAEDTAVYFCTRRG

YDWYFDVWGQGGTTVTVSS.
```

In some embodiments, the antibody or antigen-binding fragment thereof competitively inhibits the binding of CD5 to an antibody or antigen-binding fragment thereof that comprises the foregoing variable domains.

In some embodiments of any of the above aspects, the antibody or antigen-binding fragment thereof includes the following CDRs:

a CDR-H1 having the amino acid sequence GYTFTNY (SEQ ID NO: 11);
a CDR-H2 having the amino acid sequence NTHYGE (SEQ ID NO: 12);
a CDR-H3 having the amino acid sequence RRGYDWYFDV (SEQ ID NO: 13);
a CDR-L1 having the amino acid sequence RASQDINSYLS (SEQ ID NO: 14);
a CDR-L2 having the amino acid sequence RANRLES (SEQ ID NO: 15); and
a CDR-L3 having the amino acid sequence QQYDESPWT (SEQ ID NO: 16).

In some embodiments, the antibody or antigen-binding fragment thereof competitively inhibits the binding of CD5 to an antibody or antigen-binding fragment thereof that comprises the foregoing CDRs.

In some embodiments of any of the above aspects, the antibody or antigen-binding fragment thereof includes the following CDRs:

a CDR-H1 having the amino acid sequence GYSITSGYY (SEQ ID NO: 17);
a CDR-H2 having the amino acid sequence ISYSGFT (SEQ ID NO: 18);
a CDR-H3 having the amino acid sequence AGDRTGSWFAY (SEQ ID NO: 19);

a CDR-L1 having the amino acid sequence QDISNY (SEQ ID NO: 20);
a CDR-L2 having the amino acid sequence ATS (SEQ ID NO: 21); and
a CDR-L3 having the amino acid sequence LQYASYPFT (SEQ ID NO: 22).

In some embodiments, the antibody or antigen-binding fragment thereof competitively inhibits the binding of CD5 to an antibody or antigen-binding fragment thereof that comprises the foregoing CDRs.

In some embodiments of any of the above aspects, the antibody or antigen-binding fragment thereof includes the following CDRs:
a CDR-H1 having the amino acid sequence GYIFTNYG (SEQ ID NO: 23);
a CDR-H2 having the amino acid sequence INTYNGEP (SEQ ID NO: 24);
a CDR-H3 having the amino acid sequence ARGDYYGYEDY (SEQ ID NO: 25);
a CDR-L1 having the amino acid sequence QGISNY (SEQ ID NO: 26);
a CDR-L2 having the amino acid sequence YTS (SEQ ID NO: 27); and
a CDR-L3 having the amino acid sequence QQYSKLPWT (SEQ ID NO: 28).

In some embodiments, the antibody or antigen-binding fragment thereof competitively inhibits the binding of CD5 to an antibody or antigen-binding fragment thereof that comprises the foregoing CDRs.

In some embodiments of any of the above aspects, the antibody or antigen-binding fragment thereof includes the following CDRs:
a CDR-H1 having the amino acid sequence FSLSTSGMG (SEQ ID NO: 29);
a CDR-H2 having the amino acid sequence WWDDD (SEQ ID NO: 30);
a CDR-H3 having the amino acid sequence RRATGTGFDY (SEQ ID NO: 31);
a CDR-L1 having the amino acid sequence QDVGTA (SEQ ID NO: 32);
a CDR-L2 having the amino acid sequence WTSTRHT (SEQ ID NO: 33); and
a CDR-L3 having the amino acid sequence YNSYNT (SEQ ID NO: 34).

In some embodiments, the antibody or antigen-binding fragment thereof competitively inhibits the binding of CD5 to an antibody or antigen-binding fragment thereof that comprises the foregoing CDRs.

In some embodiments of any of the above aspects, the antibody or antigen-binding fragment thereof contains a combination of CDR-H1, CDR-H2, CDR-H3, CDR-L1, CDR-L2, and CDR-L3 regions set forth in Table 1, below. In some embodiments, the antibody or antigen-binding fragment thereof competitively inhibits the binding of CD5 to an antibody or antigen-binding fragment thereof that comprises a combination of CDRs set forth in Table 1, below.

In some embodiments, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

In some embodiments, the antibody is conjugated to a cytotoxin.

In some embodiments, the cytotoxin is selected from the group consisting of an amatoxin, Pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof.

In another aspect, the invention provides a method of depleting a population of CD5+ cells in a human patient, such as a population of CD5+ T cells, CD5+ B cells, and/or CD5+ NK cells in a human patient, by administering to the patient an effective amount of an antibody, fragment thereof, or antibody-drug conjugate capable of binding CD5.

In an additional aspect, the invention provides a method of depleting a population of CD5+ cells in a human patient in need of a hematopoietic stem cell transplant, such as a population of CD5+ T cells, CD5+ B cells, and/or CD5+ NK cells in a human patient in need of hematopoietic stem cell transplant, by administering, prior to the patient receiving a transplant including hematopoietic stem cells, an effective amount of an antibody, fragment thereof, or antibody-drug conjugate capable of binding CD5.

In another aspect, the invention features a method, for example, of treating a human patient in need of a hematopoietic stem cell transplant, including administering to a human patient a transplant including hematopoietic stem cells, wherein the patient has been previously administered an antibody, fragment thereof, or antibody-drug conjugate that binds to CD5 in an amount sufficient to deplete a population of CD5+ cells in the patient, such as a population of CD5+ T cells, CD5+ B cells, and/or CD5+ NK cells in the human patient.

In an additional aspect, the invention features a method, for example, of treating a human patient in need of a hematopoietic stem cell transplant, including: administering to a human patient an antibody, fragment thereof, or antibody-drug conjugate that binds to CD5 in an amount sufficient to deplete a population of CD5+ cells in the patient, such as a population of CD5+ T cells, CD5+ B cells, and/or CD5+ NK cells in the patient, and subsequently administering to the patient a transplant including hematopoietic stem cells.

In some embodiments of any of the preceding four aspects, the antibody or fragment thereof that binds to CD5 (e.g., on the surface of a CD5+ T cell, CD5+ B cell, or CD5+ NK cell) is covalently bound to an Fc domain, such as a dimeric Fc domain isolated from a human antibody (for example, isolated from an IgG1, IgG2, IgG3, or IgG4 isotype human antibody). In some embodiments, the Fc domain is a monomeric Fc domain containing a single polypeptide strand. In some embodiments, the N-terminus of the antibody or fragment thereof is bound to the Fc domain. In some embodiments, the C-terminus of the antibody or fragment thereof is bound to the Fc domain. The Fc domain may be conjugated to one or more copies of the antibody or fragment thereof. For instance, conjugates that may be used in conjunction with the methods described herein include dimeric Fc domains in which each polypeptide strand of the Fc domain is conjugated to the antibody or fragment thereof. The Fc domain may in turn be conjugated to a cytotoxin, such as a cytotoxin described herein (for example, an amatoxin, such as α-amanitin, Pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

In some embodiments, the anti-CD5 antibody or fragment thereof is covalently bound to a cytotoxin, such as a cytotoxin described herein (for example, an amatoxin, such as α-amanitin, *Pseudomonas* exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof). In some embodiments, the N-terminus of the antibody or fragment thereof is bound to the cytotoxin. In some embodiments, the C-terminus of the antibody or fragment thereof is bound to the cytotoxin. The cytotoxin may in turn be conjugated to an Fc domain.

In some embodiments, the anti-CD5 antibody or fragment thereof is covalently bound to the cytotoxin at one site on the antibody or fragment thereof (for example, the N- or C-terminus of the antibody or fragment thereof) and is covalently bound to an Fc domain at another site on the antibody or fragment thereof (for example, the opposite terminus of the antibody or fragment thereof).

In some embodiments, the Fc domain is a human IgG1 isotype Fc domain. In some embodiments, the Fc domain is a human IgG2 isotype Fc domain. In some embodiments, the Fc domain is a human IgG3 isotype Fc domain. In some embodiments, the Fc domain is a human IgG4 isotype Fc domain.

In some embodiments of any of the above aspects, the cytotoxin is an amatoxin or derivative thereof, such as α-amanitin, β-amanitin, γ-amanitin, ε-amanitin, amanin, amaninamide, amanullin, amanullinic acid, and proamanullin. In one embodiment, the cytotoxin is an amanitin. In some embodiments of any of the above aspects, the cytotoxin is an amatoxin, and the antibody, or the antigen-binding fragment thereof, conjugated to the cytotoxin is represented by the formula Ab-Z-L-Am, wherein Ab is the anti-CD5 antibody, antigen-binding fragment thereof, L is a linker, Z is a chemical moiety, and Am is the amatoxin. In some embodiments, the amatoxin is conjugated to a linker. In some embodiments, the amatoxin-linker conjugate Am-L-Z is represented by formula (I)

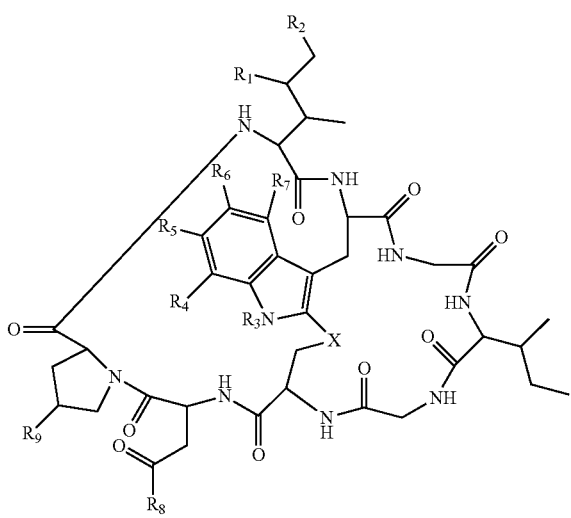

(I)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group:
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—:
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene; a dipeptide. —C(=O)—, a peptide, or a combination thereof; and
Z is a chemical moiety formed from a coupling reaction between a reactive substituent present on L and a reactive substituent present within an antibody, or an antigen-binding fragment thereof, that binds to CD5, such as on the surface of a CD5+ T cell, CD5+ B cell, or CD5+ NK cell.

In some embodiments, Am contains exactly one $R_C$ substituent.

In some embodiments, the linker L and the chemical moiety Z, taken together as L-Z, is

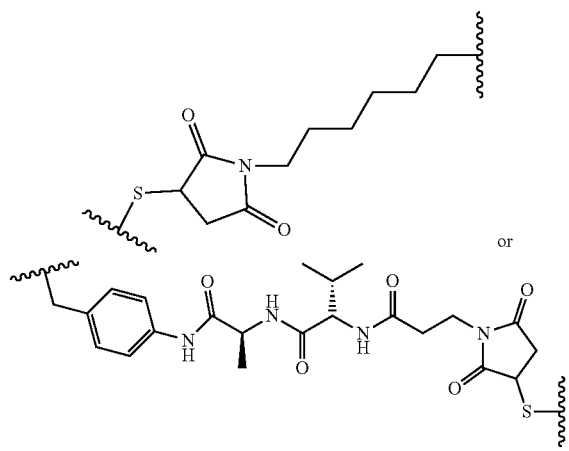

where S is a sulfur atom which represents the reactive substituent present within an antibody, or antigen-binding fragment thereof, that binds CD5 (e.g., from the —SH group of a cysteine residue).

In some embodiments, L-Z is

In some embodiments, Am-L-Z-Ab is:

In some embodiments, Am-L-Z is represented by formula (IA)

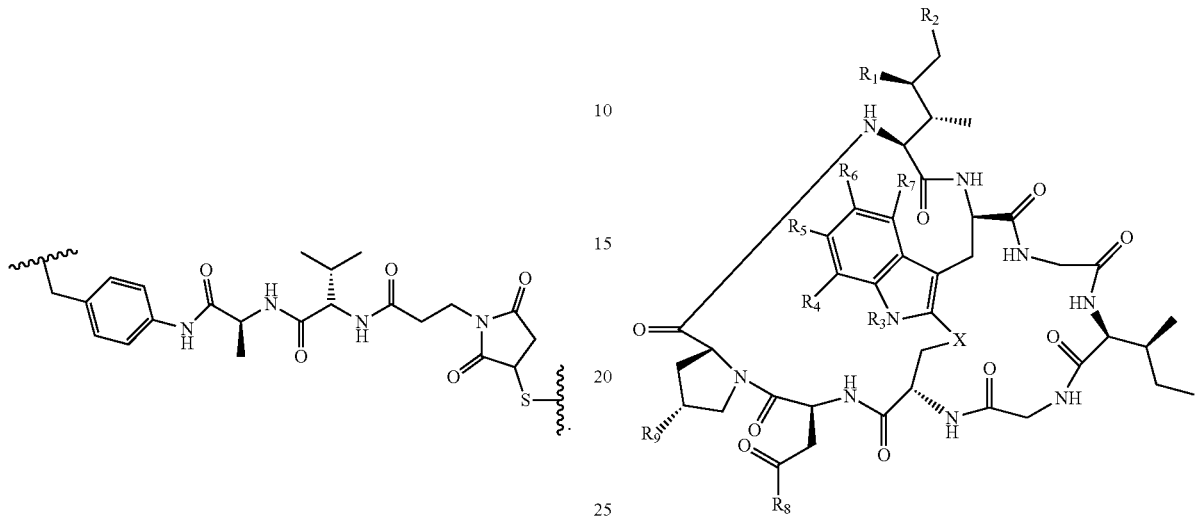

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocyclolalkyl group;

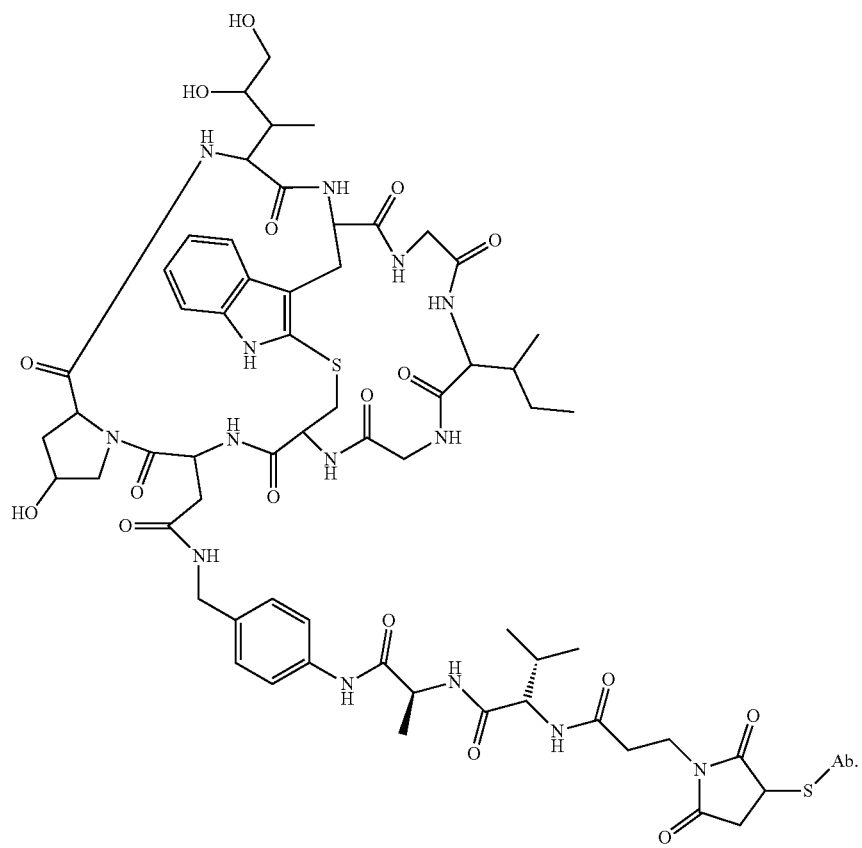

R$_3$ is H, R$_C$, or R$_D$;

R$_4$ is H, OH, OR$_C$, OR$_D$, R$_C$, or R$_D$;

R$_5$ is H, OH, OR$_C$, OR$_D$, R$_C$, or R$_D$;

R$_6$ is H, OH, OR$_C$, OR$_D$, R$_C$, or R$_D$;

R$_7$ is H, OH, OR$_C$, OR$_D$, R$_C$, or R$_D$;

R$_8$ is OH, NH$_2$, OR$_C$, OR$_D$, NHR$_C$, or NR$_C$R$_D$;

R$_9$ is H, OH, OR$_C$, or OR$_D$;

X is —S—, —S(O)—, or —SO$_2$—;

R$_C$ is -L-Z;

R$_D$ is optionally substituted alkyl (e.g., C$_1$-C$_6$ alkyl), optionally substituted heteroalkyl (e.g., C$_1$-C$_6$ heteroalkyl), optionally substituted alkenyl (e.g., C$_2$-C$_6$ alkenyl), optionally substituted heteroalkenyl (e.g., C$_2$-C$_6$ heteroalkenyl), optionally substituted alkynyl (e.g., C$_2$-C$_6$ alkynyl), optionally substituted heteroalkynyl (e.g., C$_2$-C$_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., C$_1$-C$_6$ alkylene), optionally substituted heteroalkylene (C$_1$-C$_6$ heteroalkylene), optionally substituted alkenylene (e.g., C$_2$-C$_6$ alkenylene), optionally substituted heteroalkenylene (e.g., C$_2$-C$_6$ heteroalkenylene), optionally substituted alkynylene (e.g., C$_2$-C$_6$ alkynylene), optionally substituted heteroalkynylene (e.g., C$_2$-C$_6$ heteroalkynylene), optionally substituted cycloalkylene, optionally substituted heterocycloalkylene, optionally substituted arylene, optionally substituted heteroarylene; a dipeptide, —C(=O)—, a peptide, or a combination thereof;

Z is a chemical moiety formed from a coupling reaction between a reactive substituent present on L and a reactive substituent present within an antibody, or an antigen-binding fragment thereof, that binds CD5, such as on the surface of a CD5+ T cell, CD5+ B cell, or CD5+ NK cell; and wherein Am contains exactly one R$_C$ substituent.

In some embodiments, the linker L and the chemical moiety Z, taken together as L-Z, is

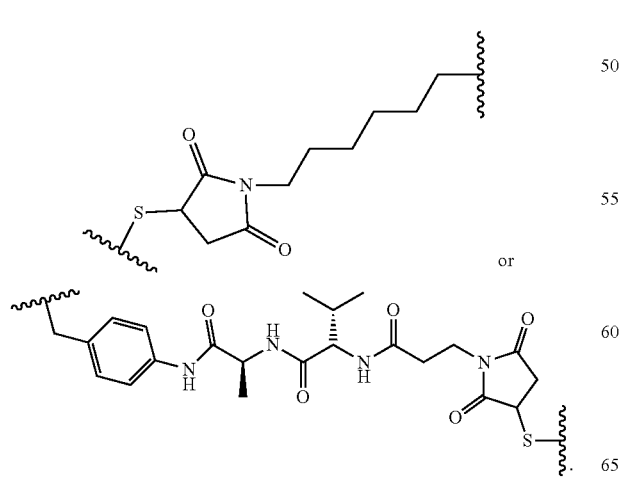

In some embodiments, L-Z is

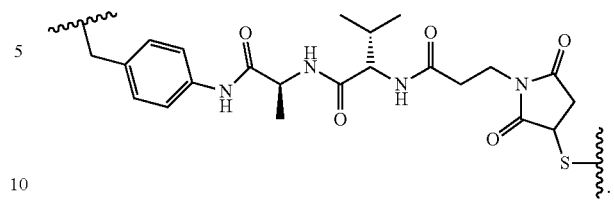

In some embodiments, Am-L-Z-Ab is

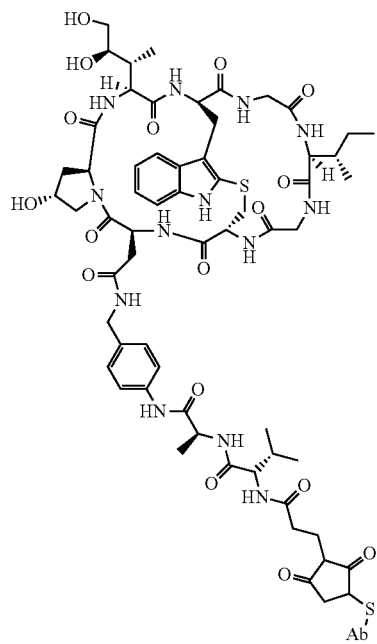

In some embodiments, Am-L-Z-Ab is

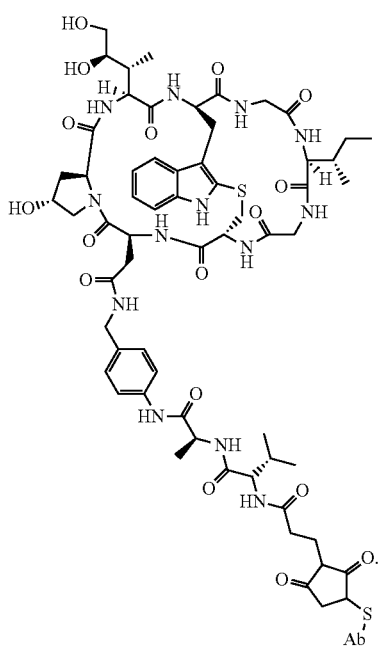

In some embodiments, Am-L-Z is represented by formula (IB)

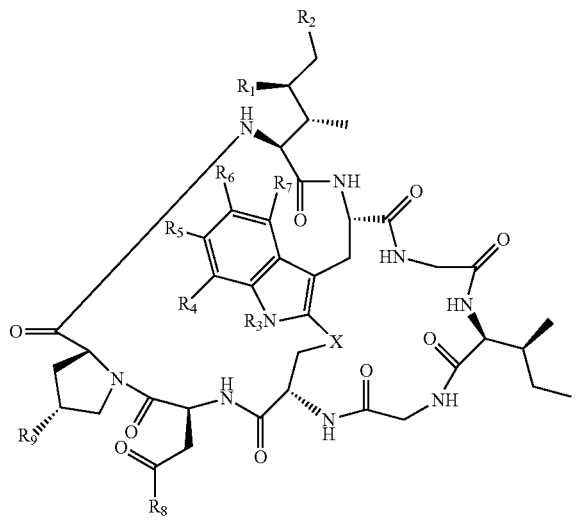

(IB)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocyclolalkyl group:
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, optionally substituted heteroaryl, a dipeptide. —C(=O)—, a peptide, or a combination thereof;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene;
Z is a chemical moiety formed from a coupling reaction between a reactive substituent present on L and a reactive substituent present within an antibody, or an antigen-binding fragment thereof, that binds CD5, such as on the surface of a CD5+ T cell, CD5+ B cell, or CD5+ NK cell; and
wherein Am contains exactly one $R_C$ substituent.

In some embodiments, $R_A$ and $R_B$, together with the oxygen atoms to which they are bound, combine to form a 5-membered heterocycloalkyl group of formula:

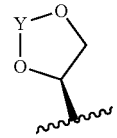

wherein Y is —C(=O)—, —C(=S)—, —C=(NR$_E$)—, or —C(R$_E$R$_{E'}$)—; and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am-L-Z is represented by formula (IA) or formula (IB), wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form:

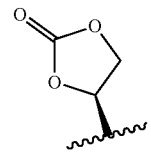 [SMILES: *[C@@H]1COC(=O)O1]

$R_3$ is H or $R_C$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, or $NHR_C$;
$R_9$ is H or OH; and
wherein $R_C$ and $R_D$ are each as defined above.

In some embodiments, Am is represented by formula (IA) or formula (IB),
wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form:

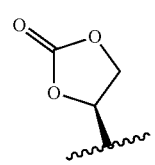 [SMILES: *[C@@H]1COC(=O)O1]

$R_3$ is H or $R_C$;
$R_4$ and $R_5$ are each independently H, OH, $OR_C$, $R_C$, or $OR_D$;

$R_6$ and $R_7$ are each H;
$R_8$ is OH, $NH_2$, $OR_C$, or $NHR_C$;
$R_9$ is H or OH; and
wherein X, $R_C$, and $R_{C'}$ are each as defined above.

In some embodiments, Am-L-Z is represented by formula (IA) or formula (IB),
wherein $R_1$ is H, OH, or $OR_A$;
$R_2$ is H, OH, or $OR_B$;
$R_A$ and $R_B$, together with the oxygen atoms to which they are bound, combine to form:

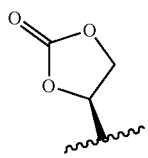 [SMILES: *[C@@H]1COC(=O)O1]

$R_3$, $R_4$, $R_6$, and $R_7$ are each H;
$R_5$ is $OR_C$;
$R_8$ is OH or $NH_2$;
$R_9$ is H or OH; and
wherein X and $R_C$ are as defined above.

In some embodiments, Am is represented by formula (IA) or formula (IB),
wherein $R_1$ and $R_2$ are each independently H or OH;
$R_3$ is $R_C$;
$R_4$, $R_6$, and $R_7$ are each H:
$R_5$ is H, OH, or $OC_1$-$C_6$ alkyl;
$R_8$ is OH or $NH_2$;
$R_9$ is H or OH; and
wherein X and $R_C$ are as defined above.

In some embodiments, Am-L-Z is represented by formula (IA) or formula (IB),
wherein $R_1$ and $R_2$ are each independently H or OH;
$R_3$, $R_6$, and $R_7$ are each H:
$R_4$ and $R_5$ are each independently H, OH, $OR_C$, or $R_C$;
$R_8$ is OH or $NH_2$;
$R_9$ is H or OH; and
wherein X or $R_C$ are as defined above.

In some embodiments, Am-L-Z is represented by formula (IA) or formula (IB),
wherein $R_1$ and $R_2$ are each independently H or OH;
$R_3$, $R_6$, and $R_7$ are each H:
$R_4$ and $R_5$ are each independently H or OH;
$R_8$ is OH, $NH_2$, $OR_C$, or $NHR_C$;
$R_9$ is H or OH; and
wherein X and $R_C$ are as defined above.

In some embodiments, the linker L and the chemical moiety Z, taken together as L-Z, is

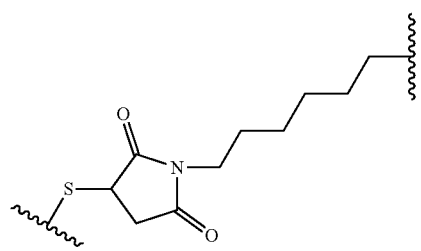

or

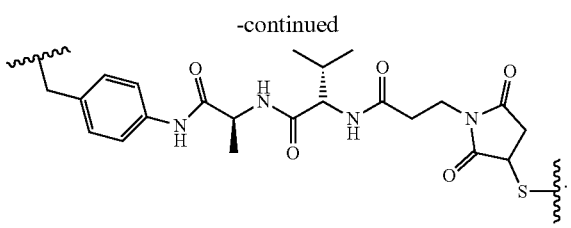

In some embodiments, L-Z is

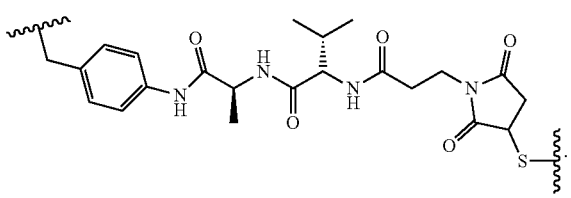

In some embodiments, Am-L-Z-Ab is

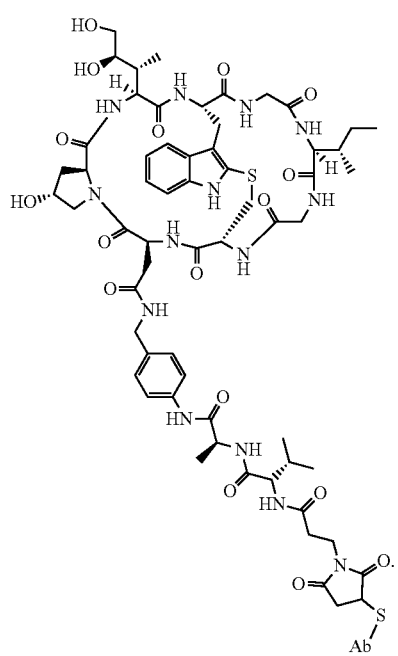

In some embodiments, Am-L-Z-Ab is

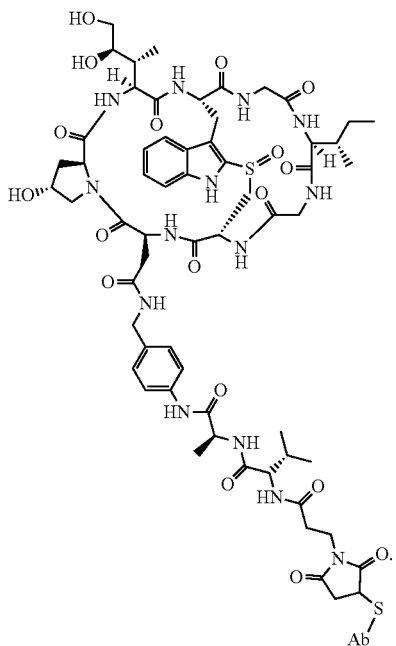

In some embodiments, Am-L-Z is represented by formula (II), formula (IIA), or formula (IIB)

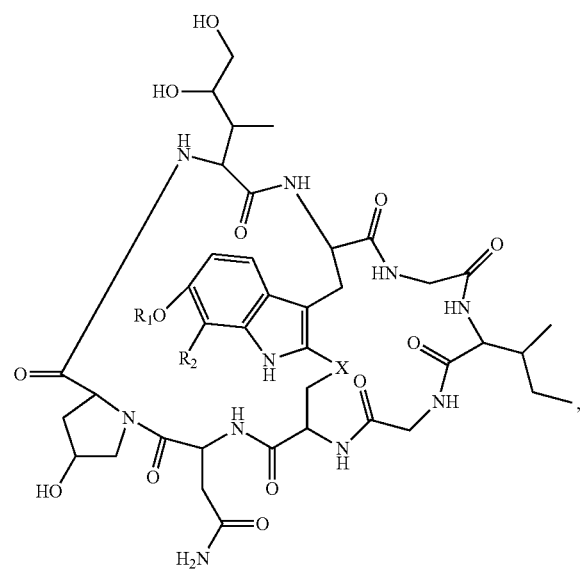

(II)

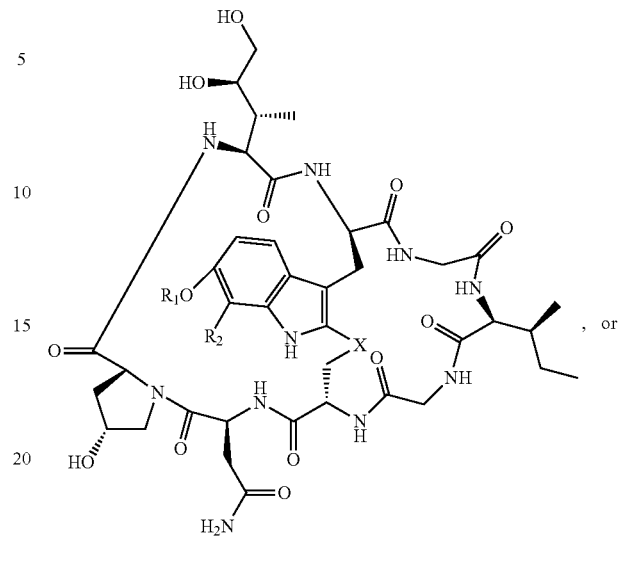

(IIA)

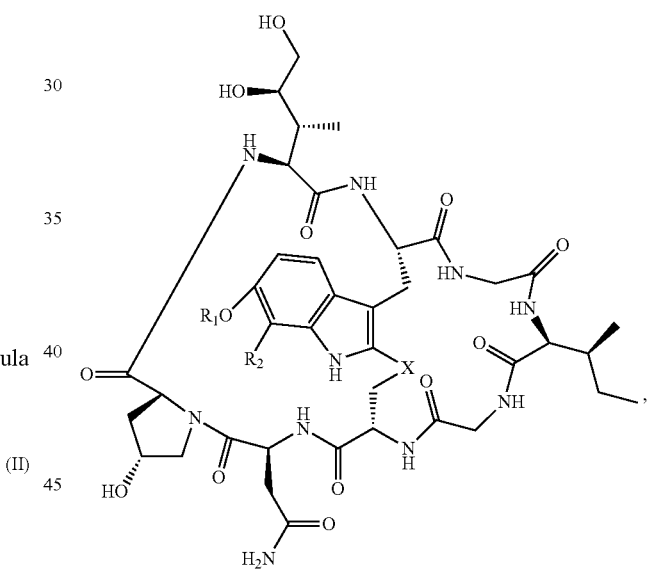

(IIB)

wherein X is S, SO, or $SO_2$; $R_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and $R_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; wherein when $R_1$ is H, $R_2$ is the linker, and when $R_2$ is H, $R_1$ is the linker.

In some embodiments, the linker comprises a $-(CH_2)_n-$ unit, where n is an integer from 2-6.

In some embodiments, R₁ is the linker and R₂ is H, and the linker and chemical moiety, together as L-Z, is In some embodiments, Am-L-Z-Ab is In some embodiments, Am-L-Z-Ab is In some embodiments, Am-L-Z-Ab is In some embodiments of any of the above aspects, the cytotoxin is a maytansinoid selected from the group consisting of DM1 and DM4. In some embodiments, the cytotoxin is an auristatin selected from the group consisting of monomethyl auristatin E and monomethyl auristatin F. In some embodiments, the cytotoxin is an anthracycline selected from the group consisting of daunorubicin, doxorubicin, epirubicin, and idarubicin.

In some embodiments, the cytotoxin is a pyrrolobenzodiazepine dimer represented by formula (IV):

(IV)

In some embodiments, the cytotoxin is conjugated to the antibody, or the antigen-binding fragment thereof, by way of a maleimidocaproyl linker.

In some embodiments, the cytotoxin is an auristatin selected from the group consisting of monomethyl auristatin E and monomethyl auristatin F.

In some embodiments, the cytotoxin is an anthracycline selected from the group consisting of daunorubicin, doxorubicin, epirubicin, and idarubicin.

In some embodiments, the anti-CD5 antibody, the antigen-binding fragment thereof, or antibody-drug conjugate is internalized by an immune cell, such as a T cell, B cell, or NK cell (e.g., a CD5+ T cell, CD5+ B cell, or CD5+ NK cell) following administration to the patient. For instance, the anti-CD5 antibody, antigen-binding fragment thereof, or antibody-drug conjugate may be internalized by T cells by receptor mediated endocytosis (e.g., upon binding to cell-surface CD5). In some embodiments, a cytotoxin covalently bound to the antibody, or the antigen-binding fragment thereof, may be released intracellularly by chemical cleavage (for instance, by enzymatic or non-specific cleavage of a linker described herein). The cytotoxin may then access its intracellular target (such as RNA polymerase, the mitotic spindle apparatus, nuclear DNA, ribosomal RNA, or topoisomerases, among others) so as to promote the death of an endogenous immune cell (e.g., CD5+ T cell, CD5+ B cell, or CD5+ NK cell) prior to hematopoietic stem cell transplantation therapy.

In some embodiments, the anti-CD5 antibody, the antigen-binding fragment thereof, or the antibody-drug conjugate is capable of promoting necrosis of an immune cell, such as a T cell, B cell, or NK cell (e.g., a CD5+ T cell, CD5+ B cell, or CD5+ NK cell). In some embodiments, the antibody, or the antigen-binding fragment thereof, may promote the death of an endogenous immune cell (e.g., CD5+ T cell, CD5+ B cell, or CD5+ NK cell) prior to transplantation therapy by recruiting one or more complement proteins, NK cells, macrophages, neutrophils, and/or eosinophils to the immune cell upon administration to the patient.

In some embodiments, an autologous transplant containing hematopoietic stem cells is administered to the patient. For instance, autologous hematopoietic stem cells can be removed from a patient, such as a patient in need of hematopoietic stem cell transplant therapy, and the cells can subsequently be administered to (e.g., infused into) the patient so as to re-populate one or more cell types of the hematopoietic lineage. The withdrawn hematopoietic stem cells may be freshly re-infused into the subject, for instance, following maintenance ex vivo for one or more hours, days, or weeks. For instance, the withdrawn hematopoietic stem cells may re-infused into the patient from 1 hour to about 1 week, from 1 hour to about 72 hours, from about 1 hour to about 48 hours, or from about 1 hour to about 24 hours following withdrawal from the patient. In some embodiments, the withdrawn hematopoietic stem cells are frozen for longer-term storage prior to re-infusion into the patient. For instance, the withdrawn hematopoietic stem cells may be frozen and cryopreserved for from 1 week to 1 year, or longer, prior to re-infusion into the patient.

In some embodiments, an allogenic transplant containing hematopoietic stem cells is administered to the patient. For instance, allogeneic hematopoietic stem cells can be removed from a donor, such as donor that is HLA-matched with respect to the patient, for instance, a closely related family member of the patient. In some embodiments, the allogenic hematopoietic stem cells are HLA-mismatched with respect to the patient. Following withdrawal of the allogeneic hematopoietic stem cells from a donor, the cells can subsequently be administered to (e.g., infused into) the patient so as to re-populate one or more cell types of the hematopoietic lineage. The withdrawn hematopoietic stem cells may be freshly infused into the subject, for instance, following maintenance ex vivo for one or more hours, days, or weeks. For instance, the withdrawn hematopoietic stem cells may infused into the patient from 1 hour to about 1 week, from 1 hour to about 72 hours, from about 1 hour to about 48 hours, or from about 1 hour to about 24 hours following withdrawal from the donor. In some embodiments, the withdrawn hematopoietic stem cells are frozen for longer-term storage prior to infusion into the patient. For instance, the withdrawn hematopoietic stem cells may be frozen and cryopreserved for from 1 week to 1 year, or longer, prior to infusion into the patient.

In some embodiments, a transplant containing hematopoietic stem cells is administered to the patient after the concentration of the anti-CD5 antibody, the antigen-binding fragment thereof, or antibody-drug conjugate has substantially cleared from the blood of the patient.

In some embodiments, a transplant containing hematopoietic stem cells is administered to the patient from 1 hour to 7 days (e.g., from 6 hours to 3 days, 12 hours to 36 hours, or about 24 hours) after the concentration of the anti-CD5 antibody, the antigen-binding fragment, or the antibody-drug conjugate has substantially cleared from the blood of the patient.

In some embodiments, the hematopoietic stem cells or progeny thereof maintain hematopoietic stem cell functional potential after two or more days (for example, from about 2 to about 5 days, from about 2 to about 7 days, from about 2 to about 20 days, from about 2 to about 30 days, such as 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or more) following transplantation of the hematopoietic stem cells into the patient.

In some embodiments, the population of CD5+ cells comprises CD34+ cells. For instance, the proportion of CD34+ cells in the population of CD5+ cells may be about 10%, 20%, 30%, 40%, 50%, 60%, 70%, 80%, 90%, 95%, 99%, or 100% of the total quantity of cells in the population.

In some embodiments, the hematopoietic stem cells or progeny thereof are capable of localizing to hematopoietic tissue, such as the bone marrow, and/or reestablishing hematopoiesis following transplantation of the hematopoietic stem cells into the patient.

In some embodiments, upon transplantation into the patient, the hematopoietic stem cells give rise to recovery of a population of cells selected from the group consisting of megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T lymphocytes, and B lymphocytes.

In some embodiments, the patient is suffering from cancer. The cancer can be a blood cancer or a type of leukemia, such as acute myeloid leukemia, acute lymphoid leukemia, chronic myeloid leukemia, or chronic lymphoid leukemia.

In some embodiments, the CD5+ cells comprise cancer cells.

In some embodiments, the anti-CD5 antibody, antigen-binding fragment thereof, or antibody-drug conjugate depletes cancer cells in a patient. For example, the antibody or antigen-binding fragment thereof may deplete 10%, 20%, 30%, 40%, 50%, 60%, 70%, 80%, 90%, or substantially all of the cancer cells in a patient.

In some embodiments, the anti-CD5 antibody, antigen-binding fragment thereof, or antibody-drug conjugate depletes blood cancer cells (e.g., leukemic cells) in a patient. In some embodiments, the blood cancer cells are acute myeloid leukemic cells, acute lymphoid leukemic cells, chronic myeloid leukemic cells, or chronic lymphoid leukemic cells. In some embodiments, the blood cancer cells are megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells. T lymphocytes, or B lymphocytes.

In some embodiments, the population of CD5+ cells comprises immune cells, such as CD5+ T cells, CD5+ B cells, and/or CD5+ NK cells.

In some embodiments of any of the above aspects, the method is used to treat one or more disorders, such as by depleting a population of immune cells in a patient, for instance, prior to hematopoietic stem cell transplant therapy so as to prevent or reduce the likelihood of rejection of the hematopoietic stem cell transplant that could otherwise be caused by a population of immune cells that cross-reacts with the hematopoietic stem cell graft, such as non-self MHC antigens expressed by the hematopoietic stem cell graft. Following transplantation, the hematopoietic stem cells may establish productive hematopoiesis, so as to replenish a deficient cell type in the patient or a cell type that is being actively killed or has been killed, for instance, by chemotherapeutic methods. For instance, the patient may be one that is suffering from a stem cell disorder. In some embodiments, the patient is suffering from a hemoglobin-opathy disorder, such as sickle cell anemia, thalassemia, Fanconi anemia, aplastic anemia, and Wiskott-Aldrich syndrome. The patient may be suffering from an immunodeficiency disorder, such as a congenital immunodeficiency disorder or an acquired immunodeficiency disorder (e.g., human immunodeficiency virus or acquired immune deficiency syndrome). In some embodiments, the patient is suffering from a metabolic disorder, such as glycogen storage diseases, mucopolysaccharidoses, Gaucher's Disease, Hurlers Disease, sphingolipidoses, and metachromatic leukodystrophy. In some embodiments, the patient is suffering from a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis. In some embodiments, the patient is suffering from an autoimmune disease, such as scleroderma, multiple sclerosis, ulcerative colitis, Chron's disease, ant Type 1 diabetes. In some embodiments, the patient is suffering from cancer or myeloproliferative disease, such as a hematological cancer. In some embodiments, the patient is suffering from acute myeloid leukemia, acute lymphoid leukemia, chronic myeloid leukemia, chronic lymohoid leukemia, multiple myeloma, diffuse large B-cell lymphoma, or non-Hodgkin's lymphoma. In some embodiments, the patient is suffering from a myelodysplastic disease, such as myelodysplastic syndrome.

In some embodiments of any of the above aspects, the method is used to directly treat a cancer, such as a cancer characterized by CD5+ cells (e.g., a leukemia characterized by CD5+ cells), by administration of an antibody, antigen-binding fragment thereof, or antibody-drug conjugate that depletes a population of CD5+ cancer cells in the patient and/or by administration of an antibody, or the antigen-binding fragment thereof, prior to hematopoietic stem cell transplant therapy so as to prevent or reduce the likelihood of rejection of the hematopoietic stem cell transplant that could otherwise be caused by a population of immune cells that cross-reacts with non-self antigens expressed by the hematopoietic stem cell graft. In the latter case, the transplantation may in turn re-constitute, for example, a population of cells depleted during the process of eradicating cancer cells. The cancer may be a hematological cancer, such as acute myeloid leukemia, acute lymphoid leukemia, chronic myeloid leukemia, chronic lymohoid leukemia, multiple myeloma, diffuse large B-cell lymphoma, or non-Hodgkin's lymphoma.

In some embodiments of any of the above aspects, the method is used to treat an autoimmune disease, such as by administration of an anti-CD5 antibody, an antigen-binding fragment thereof, or an antibody-drug conjugate so as to deplete a population of CD5+ autoimmune cells (e.g., a population of autoreactive. CD5+ T cells, B cell, and/or NK cells) and/or by administration of an antibody, or an antigen-binding fragment thereof, prior to hematopoietic stem cell transplant therapy so as to prevent or reduce the likelihood of rejection of the hematopoietic stem cell transplant that could otherwise be caused by a population of immune cells that cross-reacts with the hematopoietic stem cell graft, such as with non-self MHC antigens expressed by the hematopoietic stem cell graft. In the latter case, the transplantation may in turn re-constitute, for example, a population of cells depleted during the process of eradicating autoimmune cells. The autoimmune disease may be, for example, scleroderma, multiple sclerosis (MS), human systemic lupus (SLE), rheumatoid arthritis (RA), inflammatory bowel disease (IBD), treating psoriasis, Type 1 diabetes mellitus (Type 1 diabetes), acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis.

Thus, in some embodiments of any of the above aspects, the invention features a method of treating a hemoglobinopathy disorder, such as sickle cell anemia, thalassemia, Fanconi anemia, aplastic anemia, and Wiskott-Aldrich syndrome. In some embodiments, the invention features a method of treating an immunodeficiency disorder, such as a congenital immunodeficiency disorder or an acquired immunodeficiency disorder (e.g., human immunodeficiency virus or acquired immune deficiency syndrome). In some embodiments, the invention features a method of treating a metabolic disorder, such as glycogen storage diseases, mucopolysaccharidoses, Gaucher's Disease, Hurlers Disease, sphingolipidoses, and metachromatic leukodystrophy. In some embodiments, the invention features a method of treating a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis. In some embodiments, the invention features a method of treating an autoimmune disease, such as scleroderma, multiple sclerosis, ulcerative colitis, Chron's disease, ant Type 1 diabetes. In some embodiments, the invention features a method of treating a cancer or myeloproliferative disease, such as a hematological cancer. In some embodiments, the invention features a method of treating acute myeloid leukemia, acute lymphoid leukemia, chronic myeloid leukemia, chronic lymohoid leukemia, multiple myeloma, diffuse large B-cell lymphoma, or non-Hodgkin's lymphoma. In some embodiments, the patient is suffering from a myelodyplastic disease, such as myelodysplastic syndrome. In these embodiments, the method may include administering to the patient an antibody, an antigen-binding fragment thereof, or conjugate thereof that binds CD5, such as the antibody, the antigen-binding fragment thereof, or conjugate thereof of any of the aspects or embodiments of the invention. The method may additionally include administering to the patient a hematopoietic stem cell transplant, for instance, according to the method of any of the aspects or embodiments of the invention.

Similarly, in some embodiments of any of the above aspects, the invention provides a method of treating cancer directly, such as a cancer characterized by CD5+ cells (e.g., a leukemia characterized by CD5+ cells). In these embodiments, the method may include administering to the patient an antibody, an antigen-binding fragment thereof, or conjugate thereof that binds CD5, such as the such as the antibody, the antigen-binding fragment thereof, or conjugate thereof of any of the aspects or embodiments of the invention. The cancer may be a hematological cancer, such as acute myeloid leukemia, acute lymphoid leukemia, chronic myeloid leukemia, chronic lymohoid leukemia, multiple myeloma, diffuse large B-cell lymphoma, or non-Hodgkin's lymphoma.

Additionally, in some embodiments of any of the above aspects, the invention provides a method of treating an autoimmune disease, such as MS. SLE, RA, IBD, psoriasis, Type 1 diabetes, ADEM, Addison's disease, alopecia universalis, ankylosing spondylitisis, APS, aplastic anemia, autoimmune hemolytic anemia, autoimmune hepatitis, AIED, ALPS, autoimmune oophoritis, Balo disease, Behcet's disease, bullous pemphigoid, cardiomyopathy, Chagas' disease, CFIDS, chronic inflammatory demyelinating polyneuropathy, Crohn's disease, cicatrical pemphigoid, coeliac sprue-dermatitis herpetiformis, cold agglutinin disease. CREST syndrome, Degos disease, discoid lupus, dysautonomia, endometriosis, essential mixed cryoglobulinemia, fibromyalgia-fibromyositis, Goodpasture's syndrome. Grave's disease, GBS, Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, MCTD, myasthenia gravis, neuromyotonia, OMS, optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis. In these embodiments, the method may include administering to the patient an antibody, an antigen-binding fragment thereof, or conjugate thereof that binds CD5, such as the antibody, the antigen-binding fragment thereof, or conjugate thereof of any of the aspects or embodiments of the invention.

In another aspect, the invention features an antibody, or an antigen-binding fragment thereof, capable of binding CD5, wherein the antibody or antigen-binding fragment thereof is conjugated to a toxin.

In some embodiments, the antibody or antigen-binding fragment thereof is produced by the hybridoma cell line ATCC CRL 8000. In some embodiments, the antibody or antigen-binding fragment thereof competitively inhibits the binding of CD5 to an antibody or antigen-binding fragment thereof produced by the hybridoma cell line ATCC CRL 8000.

In some embodiments, the antibody or antigen-binding fragment thereof comprises the following variable domains:

```
a V_L having the amino acid sequence
                                        (SEQ ID NO: 1)
DIQMTQSPSSMSASLGDRVTITCRASQDINSYLSWFQQKPGKSPKTLIYR

ANRLVDGVPSRFSGSGSGTDYTLTISSLQYEDFGIYYCQQYDESPWTFGG

GTKLEIK;
and a V_H having the amino acid sequence
                                        (SEQ ID NO: 2)
QIQLVQSGPGLKKPGGSVRISCAASGYTFTNYGMNWVKQAPGKGLRWMGW

INTHTGEPTYADDFKGRFTFSLDTSKSTAYLQINSLRAEDTATYFCTRRG

YDWYFDVWGQGTTVTSS.
```

In some embodiments, the antibody or antigen-binding fragment thereof competitively inhibits the binding of CD5 to an antibody or antigen-binding fragment thereof that comprises the foregoing variable domains.

In some embodiments, the antibody or antigen-binding fragment thereof includes the following CDRs:
   a CDR-H1 having the amino acid sequence GYTFTNY (SEQ ID NO: 3);
   a CDR-H2 having the amino acid sequence NTHTGE (SEQ ID NO: 4);
   a CDR-H3 having the amino acid sequence RGYDWYFDV (SEQ ID NO: 5);

a CDR-L1 having the amino acid sequence RASQDIN-SYLS (SEQ ID NO: 6);
a CDR-L2 having the amino acid sequence RANRLVD (SEQ ID NO: 7); and
a CDR-L3 having the amino acid sequence QQYDESPWT (SEQ ID NO: 8).

In some embodiments, the antibody or antigen-binding fragment thereof competitively inhibits the binding of CD5 to an antibody or antigen-binding fragment thereof that comprises the foregoing CDRs.

In some embodiments, the antibody or antigen-binding fragment thereof comprises the following variable domains:

a $V_L$ having the amino acid sequence
(SEQ ID NO: 9)
DIQMTQSPSSLSASVGDRVTITCRASQDINSYLSWFQQKPGKAPKTLIYR
ANRLESGVPSRFSGSGSGTDYTLTIS SLQYEDFGIYYCQQYDESPWTFG
GGTKLEIK;
and a $V_H$ having the amino acid sequence
(SEQ ID NO: 10)
EIQLVQSGGGLVKPGGSVRISCAASGYTFTNYGMNWVRQAPGKGLEWMGW
INTHYGEPTYADSFKGTRTFSLDDSKNTAYLQINSLRAEDTAVYFCTRRG
YDWYFDVWGQGGTTVTVSS.

In some embodiments, the antibody or antigen-binding fragment thereof competitively inhibits the binding of CD5 to an antibody or antigen-binding fragment thereof that comprises the foregoing variable domains.

In some embodiments, the antibody or antigen-binding fragment thereof includes the following CDRs:
a CDR-H1 having the amino acid sequence GYTFTNY (SEQ ID NO: 11);
a CDR-H2 having the amino acid sequence NTHYGE (SEQ ID NO: 12);
a CDR-H3 having the amino acid sequence RRGYDWYFDV (SEQ ID NO: 13);
a CDR-L1 having the amino acid sequence RASQDIN-SYLS (SEQ ID NO: 14);
a CDR-L2 having the amino acid sequence RANRLES (SEQ ID NO: 15); and
a CDR-L3 having the amino acid sequence QQYDESPWT (SEQ ID NO: 16).

In some embodiments, the antibody or antigen-binding fragment thereof competitively inhibits the binding of CD5 to an antibody or antigen-binding fragment thereof that comprises the foregoing CDRs.

In some embodiments, the antibody or antigen-binding fragment thereof includes the following CDRs:
a CDR-H1 having the amino acid sequence GYSITSGYY (SEQ ID NO: 17);
a CDR-H2 having the amino acid sequence ISYSGFT (SEQ ID NO: 18);
a CDR-H3 having the amino acid sequence AGDRTGSWFAY (SEQ ID NO: 19);
a CDR-L1 having the amino acid sequence QDISNY (SEQ ID NO: 20);
a CDR-L2 having the amino acid sequence ATS (SEQ ID NO: 21); and
a CDR-L3 having the amino acid sequence LQYASYPFT (SEQ ID NO: 22).

In some embodiments, the antibody or antigen-binding fragment thereof competitively inhibits the binding of CD5 to an antibody or antigen-binding fragment thereof that comprises the foregoing CDRs.

In some embodiments, the antibody or antigen-binding fragment thereof includes the following CDRs:
a CDR-H1 having the amino acid sequence GYIFTNYG (SEQ ID NO: 23);
a CDR-H2 having the amino acid sequence INTYNGEP (SEQ ID NO: 24);
a CDR-H3 having the amino acid sequence ARGDYYGYEDY (SEQ ID NO: 25);
a CDR-L1 having the amino acid sequence QGISNY (SEQ ID NO: 26);
a CDR-L2 having the amino acid sequence YTS (SEQ ID NO: 27); and
a CDR-L3 having the amino acid sequence QQYSK-LPWT (SEQ ID NO: 28).

In some embodiments, the antibody or antigen-binding fragment thereof competitively inhibits the binding of CD5 to an antibody or antigen-binding fragment thereof that comprises the foregoing CDRs.

In some embodiments, the antibody or antigen-binding fragment thereof includes the following CDRs:
a CDR-H1 having the amino acid sequence FSLST-SGMG (SEQ ID NO: 29);
a CDR-H2 having the amino acid sequence WWDDD (SEQ ID NO: 30);
a CDR-H3 having the amino acid sequence RRATGTGFDY (SEQ ID NO: 31);
a CDR-L1 having the amino acid sequence QDVGTA (SEQ ID NO: 32);
a CDR-L2 having the amino acid sequence WTSTRHT (SEQ ID NO: 33); and
a CDR-L3 having the amino acid sequence YNSYNT (SEQ ID NO: 34).

In some embodiments, the antibody or antigen-binding fragment thereof competitively inhibits the binding of CD5 to an antibody or antigen-binding fragment thereof that comprises the foregoing CDRs.

In some embodiments, the antibody or antigen-binding fragment thereof contains a combination of CDR-H1, CDR-H2, CDR-H3, CDR-L1, CDR-L2, and CDR-L3 regions set forth in Table 1, below. In some embodiments, the antibody or antigen-binding fragment thereof competitively inhibits the binding of CD5 to an antibody or antigen-binding fragment thereof that comprises a combination of CDRs set forth in Table 1, below.

In some embodiments, the anti-CD5 antibody or antigen-binding fragment thereof comprises a heavy chain variable region as set forth in SEQ ID NO: 257 and a light chain variable region as set forth in SEQ ID NO: 258. In some embodiments, the antibody or antigen-binding fragment thereof competitively inhibits the binding of CD5 to an antibody or antigen-binding fragment thereof that comprises a heavy chain variable region as set forth in SEQ ID NO: 257 and a light chain variable region as set forth in SEQ ID NO: 258.

In some embodiments, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, an scFv, a diabody, a triabody, a nanobody, an antibody-like protein scaffold, a Fv fragment, a Fab fragment, a F(ab')$_2$ molecule, and a tandem di-scFv.

In some embodiments, the antibody has an isotype selected from the group consisting of IgG, IgA, IgM, IgD, and IgE.

In some embodiments, the antibody, or the antigen-binding fragment thereof, conjugated to the cytotoxin is represented by the formula Ab-Cy, wherein Ab is the antibody, or the antigen-binding fragment thereof, and Cy is the cytotoxin. In some embodiments, the cytotoxin is selected from the group consisting of an amatoxin, *Pseudomonas* exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof.

In some embodiments, the cytotoxin is an amatoxin or derivative thereof, such as α-amanitin, β-amanitin, γ-amanitin, ε-amanitin, amanin, amaninamide, amanullin, amanullinic acid, and proamanullin. In some embodiments, the cytotoxin is an amatoxin, and the antibody, or the antigen-binding fragment thereof, conjugated to the cytotoxin is represented by the formula Ab-Z-L-Am, wherein Ab is the antibody, or the antigen-binding fragment thereof, Z is a chemical moiety, Li is a linker, and Am is the amatoxin. In some embodiments, Am-L-Z is represented by formula (I)

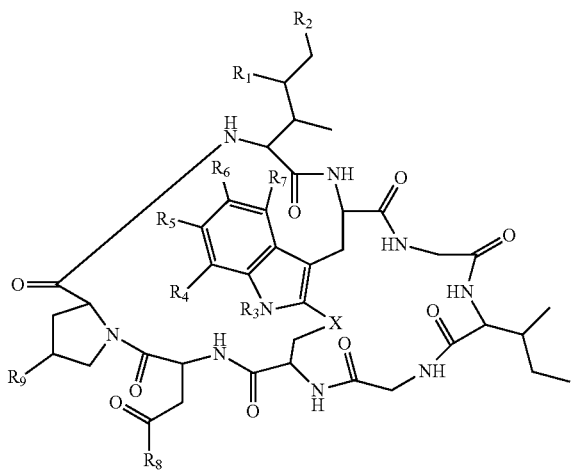

(I)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocycloalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z:

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene; a dipeptide, —C(=O)—, a peptide, or a combination thereof; and Z is a chemical moiety formed from a coupling reaction between a reactive substituent present on L and a reactive substituent present within an antibody, or an antigen-binding fragment thereof, that binds CD5, such as on the surface of a CD5+ T cell, CD5+ B cell, or CD5+ NK cell.

In some embodiments, Am contains exactly one $R_C$ substituent.

In some embodiments, Am-L-Z is represented by formula (IA)

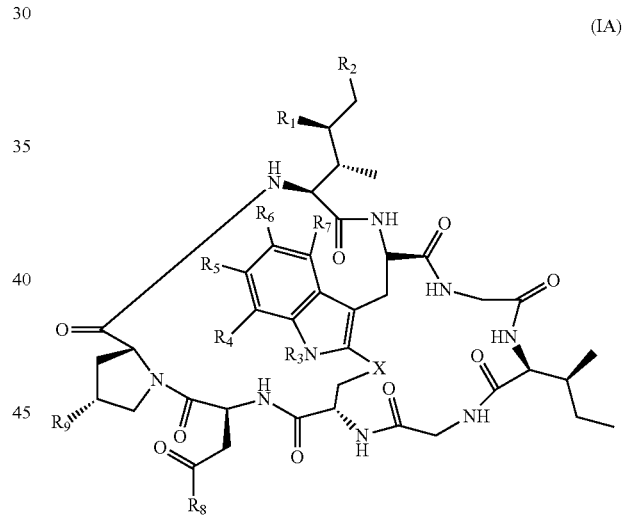

(IA)

wherein $R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form an optionally substituted 5-membered heterocyclolalkyl group:

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —C(=O)—, a peptide, or a combination thereof;

Z is a chemical moiety formed from a coupling reaction between a reactive substituent present on L and a reactive substituent present within an antibody, an antigen-binding fragment thereof, that binds CD5, such as on the surface of a CD5+ T cell, CD5+ B cell, or CD5+ NK cell; and wherein Am contains exactly one $R_C$ substituent.

In some embodiments, the linker L and the chemical moiety Z, taken together as L-Z, is

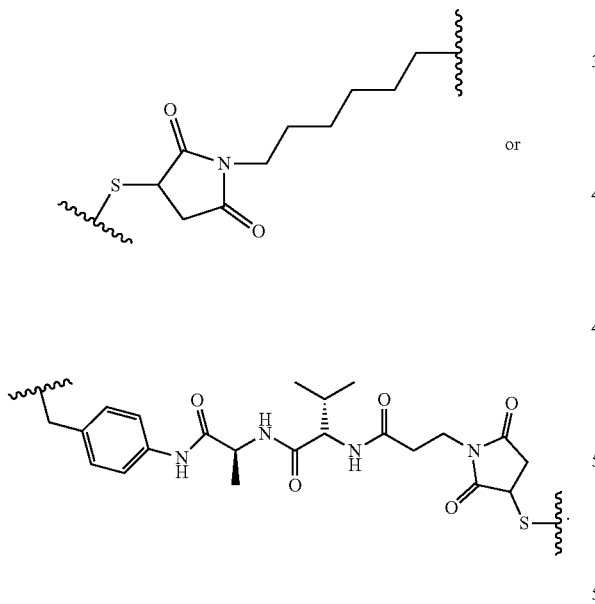

or

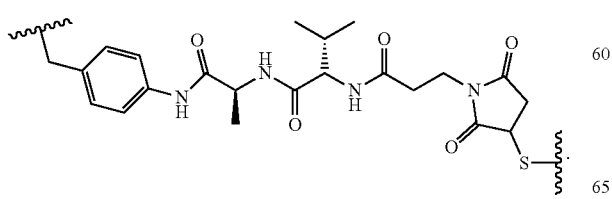

In some embodiments, L-Z is

In some embodiments, Am-L-Z-Ab is

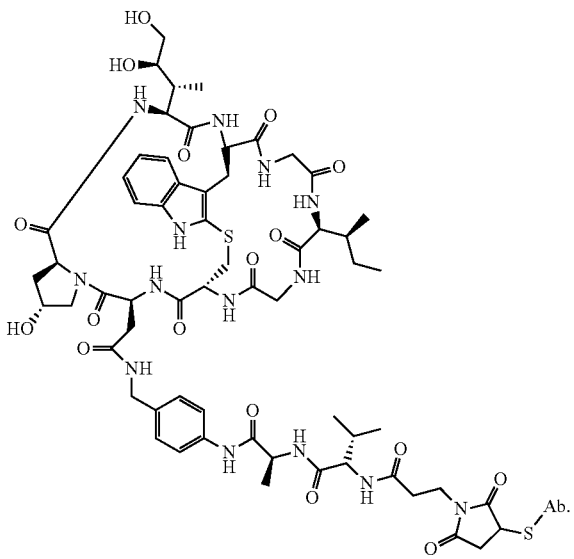

In some embodiments, Am-L-Z-Ab is

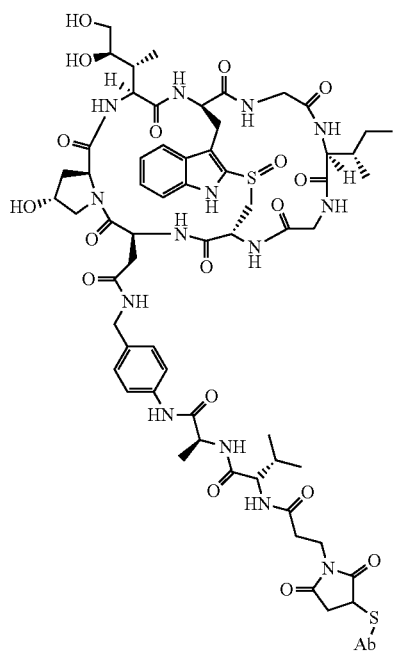

In some embodiments, Am-L-Z is represented by formula (IB)

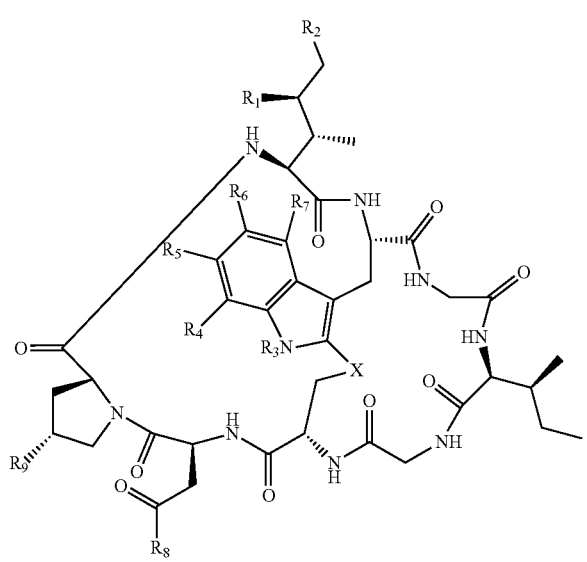

(IB)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocyclolalkyl group:
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —C(=O)—, a peptide, or a combination thereof;
Z is a chemical moiety formed from a coupling reaction between a reactive substituent present on L and a reactive substituent present within an antibody, or an antigen-binding fragment thereof, that binds CD5, such as on the surface of a CD5+ T cell, CD5+ B cell, or CD5+ NK cell; and
wherein Am contains exactly one $R_C$ substituent.

In some embodiments, the linker L and the chemical moiety Z, taken together as L-Z, is

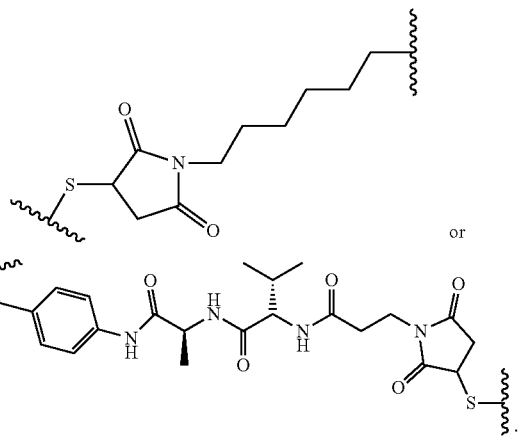

In some embodiments, L-Z is

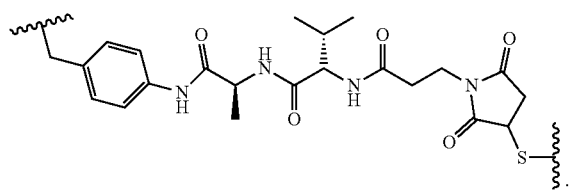

In some embodiments, Am-L-Z-Ab is

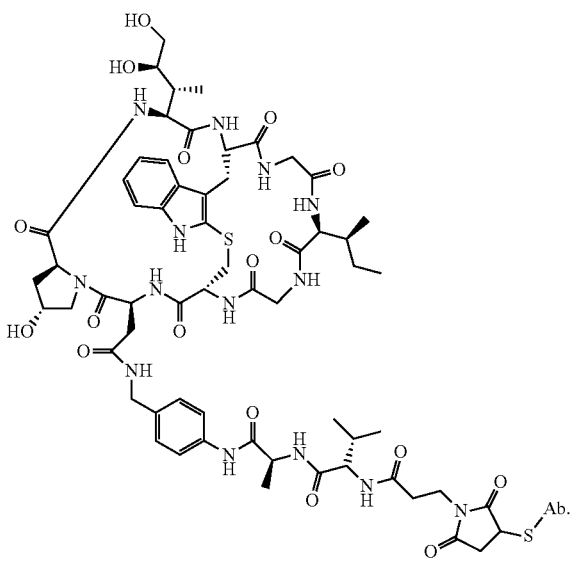

In some embodiments, Am-L-Z-Ab is

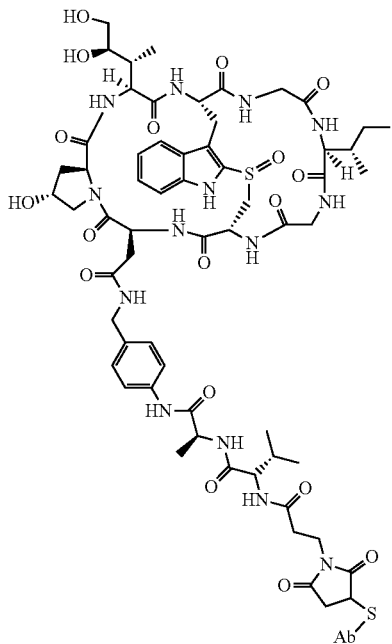

In some embodiments, $R_A$ and $R_B$, together with the oxygen atoms to which they are bound, combine to form a 5 membered heterocycloalkyl group of formula:

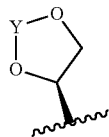

wherein Y is —C(=O)—, —C(=S)—, —C(=NR$_E$)—, or —C(R$_E$R$_{E'}$)—; and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am-L-Z is represented by formula (IA) or formula (IB), wherein $R_1$ is H, OH, OR$_A$, or OR$_C$;

$R_2$ is H, OH, OR$_B$, or OR$_C$;

$R_A$ and $R_B$, together with the oxygen atoms to which they are bound, combine to form:

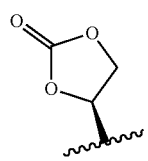 [SMILES: *[C@@H]1COC(=O)O1]

$R_3$ is H or $R_C$;
$R_4$ is H, OH, OR$_C$, OR$_D$, $R_C$, or $R_D$;
$R_5$ is H, OH, OR$_C$, OR$_D$, $R_C$, or $R_D$;
$R_6$ is H, OH, OR$_C$, OR$_D$, $R_C$, or $R_D$;
$R_7$ is H, OH, OR$_C$, OR$_D$, $R_C$, or $R_D$;
$R_8$ is OH, NH$_2$, OR$_C$, or NHR$_C$;
$R_9$ is H or OH; and
wherein X, $R_C$ and $R_D$ are each as defined above.

In some embodiments, Am-L-Z is represented by formula (IA) or formula (IB), wherein $R_1$ is H, OH, OR$_A$, or OR$_C$;
$R_2$ is H, OH, OR$_B$, or OR$_C$;
$R_A$ and $R_B$, together with the oxygen atoms to which they are bound, combine to form:

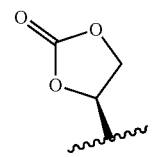 [SMILES: *[C@@H]1COC(=O)O1]

$R_3$ is H or $R_C$;
$R_4$ and $R_5$ are each independently H, OH, OR$_C$, $R_C$, or OR$_D$;
$R_6$ and $R_7$ are each H;
$R_8$ is OH, NH$_2$, OR$_C$, or NHR$_C$;
$R_9$ is H or OH; and
wherein $R_C$ is as defined above.

In some embodiments, Am is represented by formula (IA) or formula (IB), wherein $R_1$ is H, OH, or OR$_A$;
$R_2$ is H, OH, or OR$_B$;
$R_A$ and $R_B$, together with the oxygen atoms to which they are bound, combine to form:

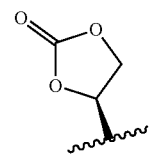 [SMILES: *[C@@H]1COC(=O)O1]

$R_3$, $R_4$, $R_6$, and $R_7$ are each H;
$R_5$ is OR$_C$;
$R_8$ is OH or NH$_2$;
$R_9$ is H or OH; and
wherein X and $R_C$ are as defined above.

In some embodiments, Am-L-Z is represented by formula (IA) or formula (IB), wherein $R_1$ and $R_2$ are each independently H or OH:
$R_3$ is $R_C$;
$R_4$, $R_6$, and $R_7$ are each H:
$R_5$ is H, OH, or OC$_1$-C$_6$ alkyl;
$R_8$ is OH or NH$_2$;
$R_9$ is H or OH; and
wherein X and $R_C$ are as defined above.

In some embodiments, Am-L-Z is represented by formula (IA) or formula (IB), wherein $R_1$ and $R_2$ are each independently H or OH:
$R_3$, $R_6$, and $R_7$ are each H;
$R_4$ and $R_5$ are each independently H, OH, OR$_C$, or $R_C$;
$R_8$ is OH or NH$_2$;
$R_9$ is H or OH; and
Wherein X and $R_C$ areas defined above.

In some embodiments, Am-L-Z is represented by formula (IA) or formula (IB), wherein R₁ and R₂ are each independently H or OH:

R₃, R₆, and R₇ are each H;

R₄ and R₅ are each independently H or OH;

R₈ is OH, NH₂, OR$_C$, or NHR$_C$;

R₉ is H or OH; and wherein A and R$_C$ are as defined above.

In some embodiments, the linker L and the chemical moiety Z, taken together as L-Z, is

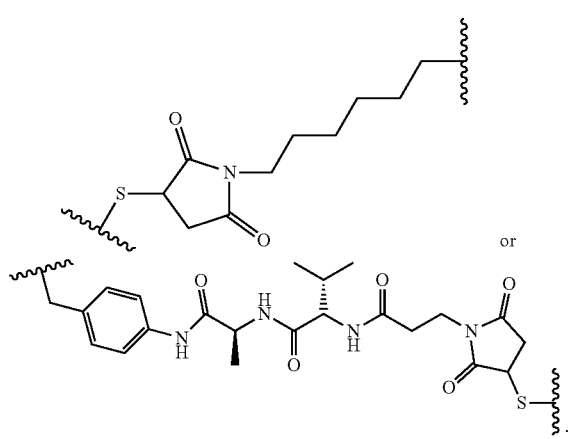

or

In some embodiments, L-Z is

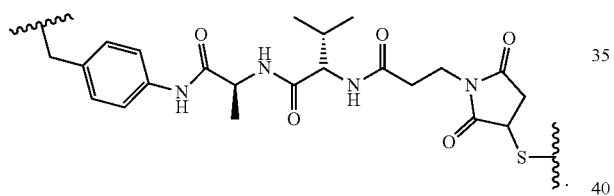

In some embodiments, the Am-L-Z precursor is

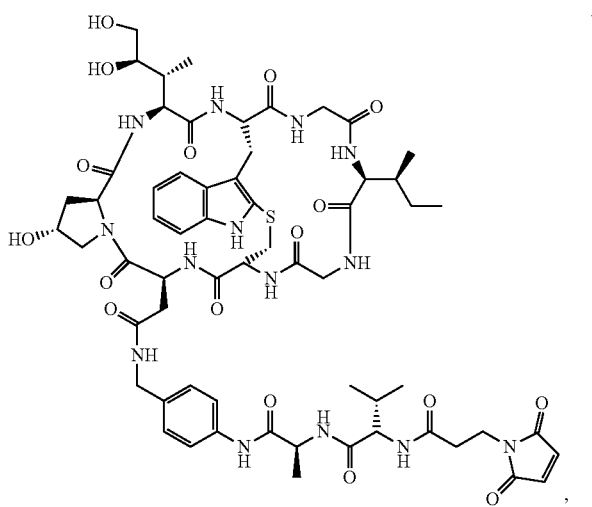

wherein the maleimide reacts with a thiol group found on a cysteine in the antibody.

In some embodiments, the Am-L-Z precursor is

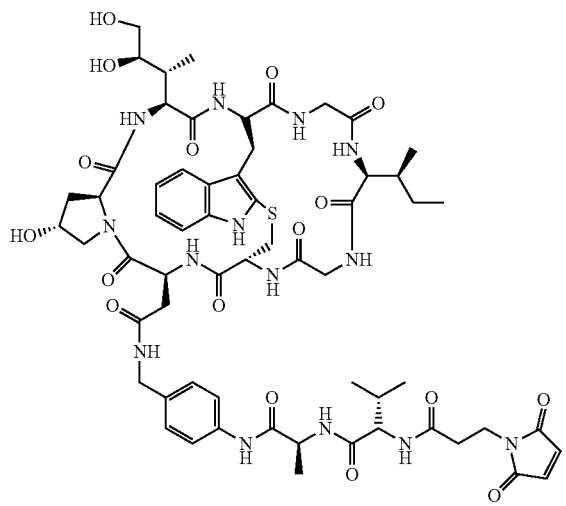

wherein the maleimide reacts with a thiol group found on a cysteine in the antibody.

In some embodiments, Am-L-Z is represented by formula (II), formula (IIA), or formula (IIB)

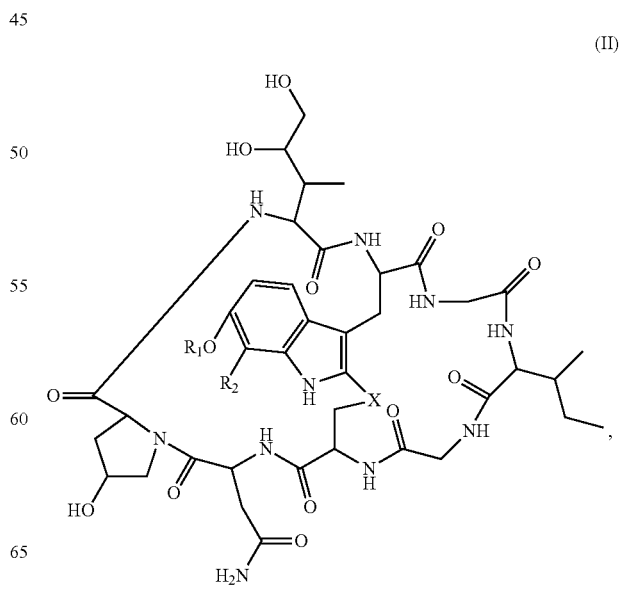

(II)

-continued (IIA)

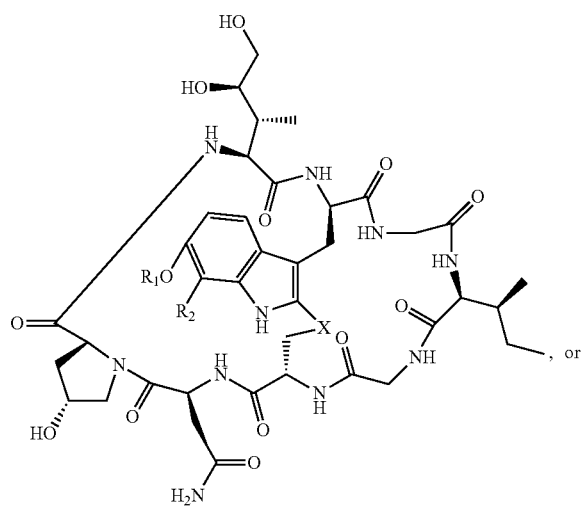

(IIB)

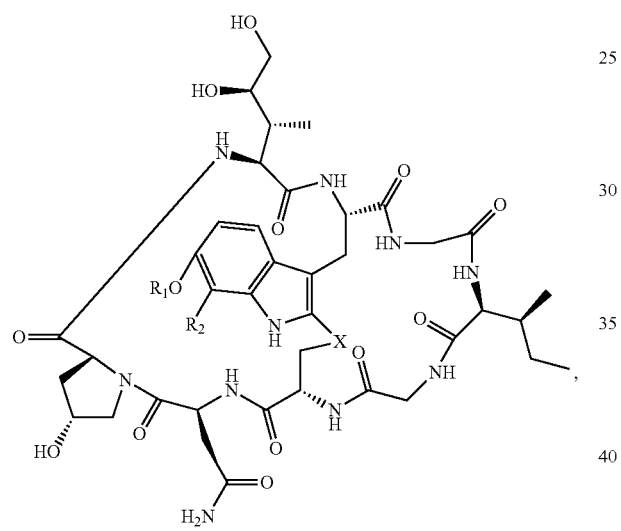

wherein X is S, SO, or SO₂; R₁ is H or a linker covalently bound to the antibody or antigen-binding fragment thereof through a chemical moeity Z, formed from a coupling reaction between a reactive substituent present on the linker and a reactive substituent present within an antibody, or antigen-binding fragment thereof; and R₂ is H or a linker covalently bound to the antibody or antigen-binding fragment thereof through a chemical moeity Z, formed from a coupling reaction between a reactive substituent present on the linker and a reactive substituent present within an antibody, or antigen-binding fragment thereof; wherein when R₁ is H, R₂ is the linker, and when R₂ is H, R₁ is the linker.

In some embodiments, the linker comprises a —(CH)$_{2n}$— unit, where n is an integer from 2-6.

In some embodiments, R₁ is the linker and R₂ is H, and the linker and chemical moiety, together as L-Z, is

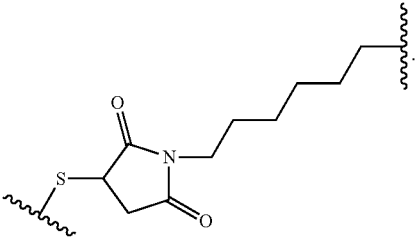 [SMILES: *CCCCCCN1C(=O)CC(S*)C1=O]

In some embodiments, Ab-Z-L-Am is

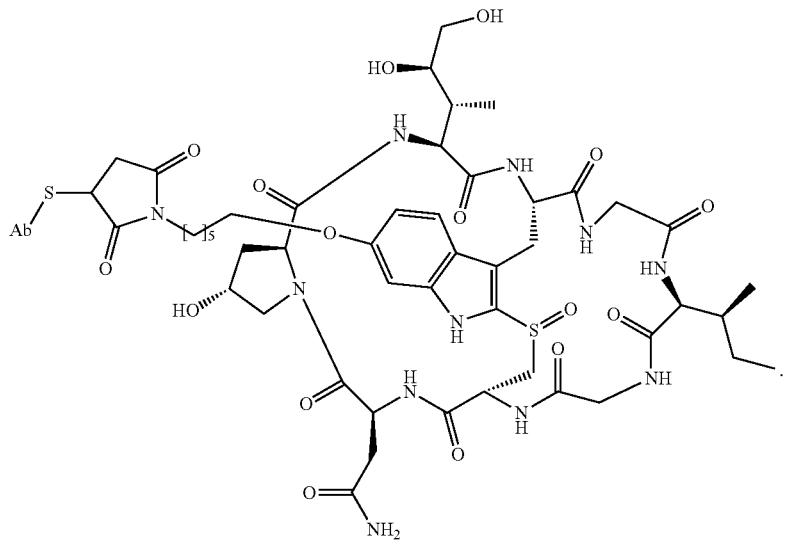

In some embodiments, Ab-Z-L-Am is

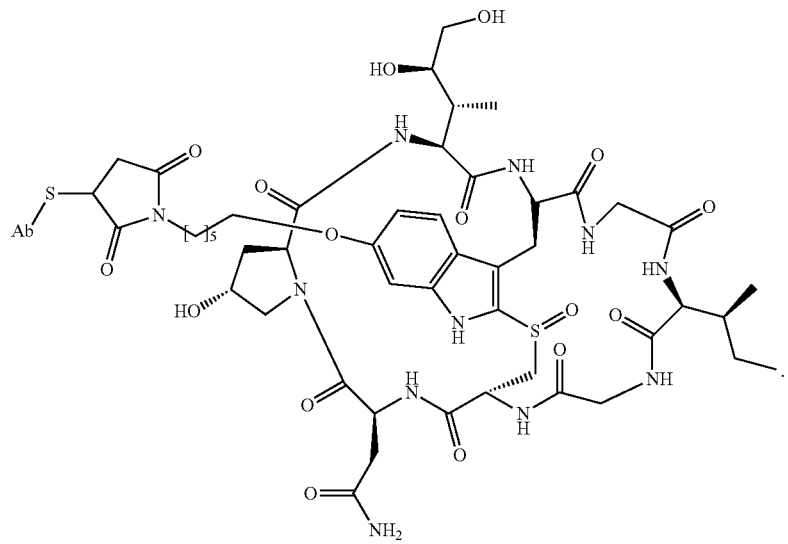

In some embodiments, the Am-L-Z precursor is one of:

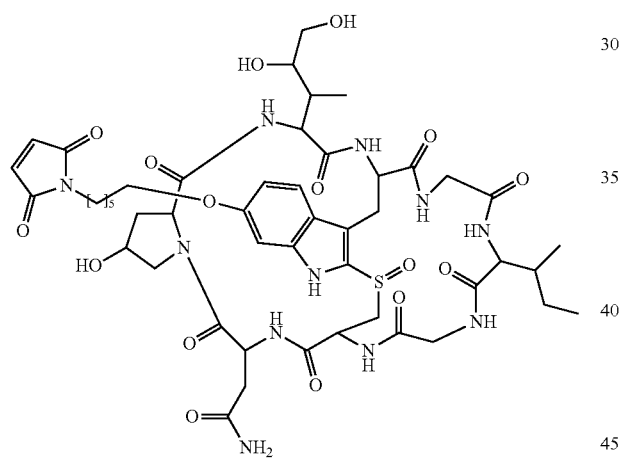

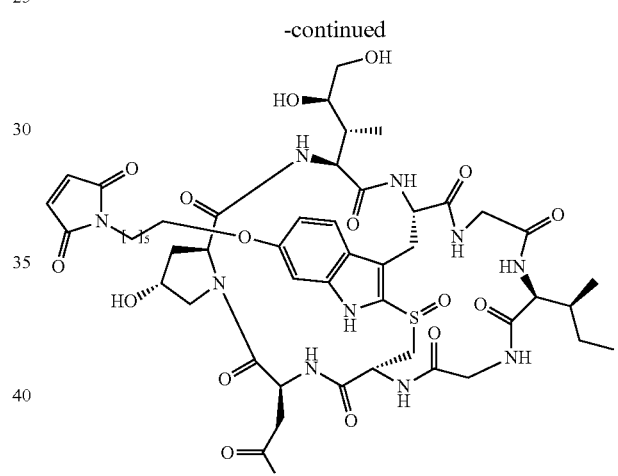

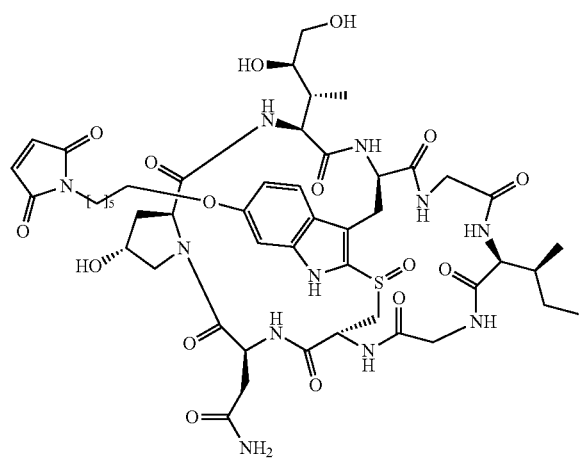

wherein the maleimide reacts with a thiol group found on a cysteine in the antibody.

In some embodiments, the cytotoxin is a maytansinoid selected from the group consisting of DM1 and DM4. In some embodiments, the cytotoxin is an aurstatin selected from the group consisting of monomethyl auristatin E and monomethyl auristatin F. In some embodiments, the cytotoxin is an anthracycline selected from the group consisting of daunorubicin, doxorubicin, epirubicin, and idarubicin.

In some embodiments, the cytotoxin is a pyrrolobenzodiazepine dimer represented by formula (IV):

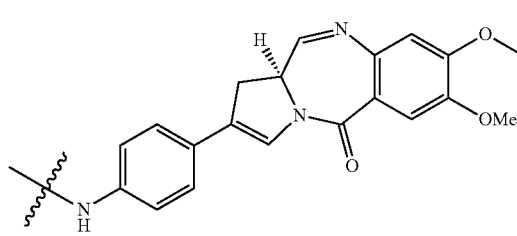

(IV)

In some embodiments, the cytotoxin is conjugated to the antibody, or the antigen-binding fragment thereof, by way of a maleimidocaproyl linker.

In some embodiments, the cytotoxin is an auristatin selected from the group consisting of monomethyl auristatin E and monomethyl auristatin F.

In some embodiments, the cytotoxin is an anthracycline selected from the group consisting of daunorubicin, doxorubicin, epirubicin, and idarubicin.

In another aspect, the invention features a pharmaceutical composition comprising the antibody, or the antigen-binding fragment thereof, of any of the above aspects or embodiments of the invention and a pharmaceutically acceptable excipient.

In some embodiments, the pharmaceutical composition is formulated for administration to a human patient transdermally, subcutaneously, intranasally, intravenously, intramuscularly, intraocularly, intratumorally, parenterally, topically, intrathecally or intracerebroventricularly.

BRIEF DESCRIPTION OF THE FIGURES

In FIG. 3A, the anti-CD5-ADC T-cell killing analysis is shown in comparison to an unconjugated anti-CD5 5D7 antibody (i.e., "CD5 Naked"). In FIG. 3B, the anti-CD5 antibody the results are shown in comparison to an anti-CD5 5D7 antibody having a H435A mutation that decreases the half life of the antibody (i.e., "CD5 Fast % Life AM"). The results show the number of viable T-cells (y-axis) as a function of ADC (CD5 5D7 AM, CD5 5D7 D265C.H435A AM) or unconjugated antibody (CD5 5D7) concentration (x-axis) as assessed using flow cytometry.

FIGS. 5A-5C also show the level of T-cell depletion following treatment of humanized NSG mice with 3 mg/kg of an unconjugated anti-CD5 antibody or with the indicated controls (i.e., 3 mg/kg hIgG1-amanitan-ADC ("hIgG1-AM") or PBS).

DETAILED DESCRIPTION

Figure 1:
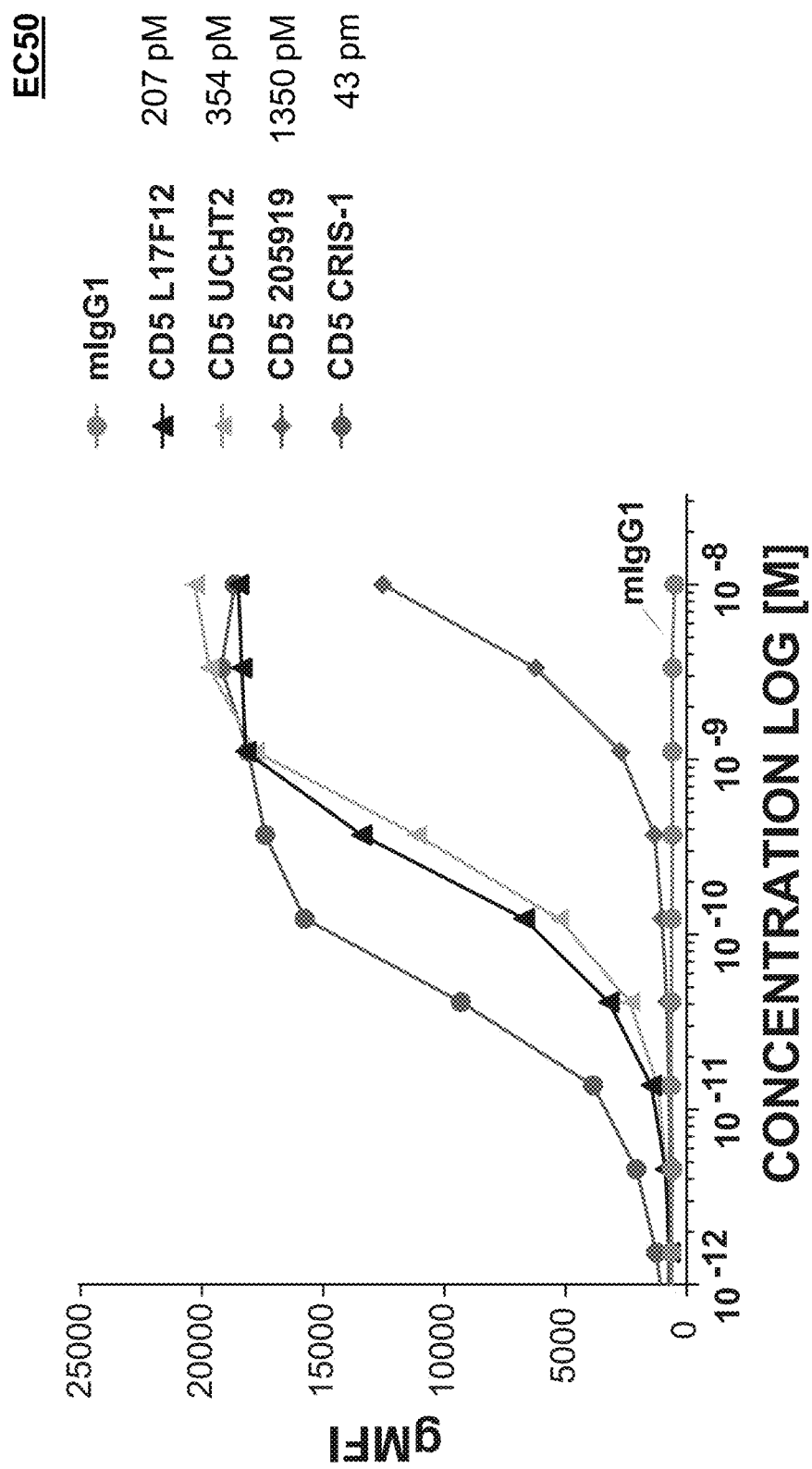
FIG. 1 graphically depicts the results of an in vitro cell line binding assay in which each of the indicated anti-CD5 antibodies or a negative control (i.e., mIgG1) was incubated with MOLT-4 cells (i.e., a human T lymphoblast cell line) followed by incubation of a fluorophore-conjugated anti-IgG antibody. Signal was detected through flow cytometry and is indicated as the geometric mean fluorescence intensity (y-axis) as a function of anti-CD5 antibody concentration (x-axis).

The present invention is based in part on the discovery that antibodies, or the antigen-binding fragments thereof, that bind to CD5 (also referred to as Lymphocyte antigen T1/Leu-1) can be used as therapeutic agents to (i) directly treat cancers and autoimmune diseases characterized by CD5+ cells and (ii) promote the engraftment of transplanted hematopoietic stem cells in a patient in need of transplant therapy by depleting populations of immune cells that cross-react with, and mount an immune response against, non-self hematopoietic stem cell grafts. These therapeutic activities can arise, for instance, by the binding of anti-CD5 antibodies, or antigen-binding fragments thereof, to CD5 expressed on the surface of a cell, such as a cancer cell, autoimmune cell, or immune cell that cross-reacts with a non-self hematopoietic stem cell antigen, thereby inducing death of the bound cell. In the case of depleting a population of cancer cells or autoimmune cells, the anti-CD5 antibody, or the antigen-binding fragment thereof, can be used to directly treat a cancer or autoimmune disease, such as a cancer autoimmune disease described herein. In the case of depleting a population of immune cells that cross-react with a non-self hematopoietic stem cell antigen (e.g., a non-self MHC antigen expressed by the hematopoietic stem cell graft), the anti-CD5 antibody, or the antigen-binding fragment thereof, can be used to prevent or reduce the likelihood of graft rejection in a patient that is suffering from a stem cell disorder, cancer, or autoimmune disease and that is undergoing hematopoietic stem cell transplant therapy. In such instances, the depletion of CD5+ immune cells that cross-react with one or more non-self hematopoietic stem cell antigens (e.g., one or more non-self MHC antigens) enables the successful engraftment of transplanted hematopoietic stem cells within the transplant recipient. As the transplanted cells engraft, they can home to hematopoietic tissue, where productive hematopoiesis can then ensue. The transplanted hematopoietic stem cells can subsequently give rise to a population of cells that is deficient or defective in the transplant recipient, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T lymphocytes, and B lymphocytes. In this way, anti-CD5 antibodies, or the fragments thereof, can be used to promote the successful engraftment of hematopoietic stem cells in a patient, such as human patient suffering from a stem cell disorder described herein.

Definitions

As used herein, the term "about" refers to a value that is within 10% above or below the value being described. For example, the term "about 5 nM" indicates a range of from 4.5 nM to 5.5 nM.

As used herein, the term "amatoxin" refers to a member of the amatoxin family of peptides produced by *Amanita phalloides* mushrooms, a synthetic amatoxin, a variant amatoxin, or a derivative thereof, such as a variant or derivative thereof capable of inhibiting RNA polymerase II activity. Also included are synthetic amatoxins (see, e.g., U.S. Pat. No. 9,676,702, incorporated by reference herein). As described herein, amatoxins may be conjugated to an antibody, or antigen-binding fragment thereof, for instance, by way of a linker moiety (L) (thus forming a conjugate (also referred to as an antibody drug conjugate (ADC)). Exemplary methods of amatoxin conjugation and linkers useful for such processes are described below. Exemplary linker-containing amatoxins useful for conjugation to an antibody, or antigen-binding fragment, in accordance with the compositions and methods are also described herein.

In certain embodiments, amatoxins useful in conjunction with the compositions and methods described herein include compounds according to formula (III), below, such as α-amanitin, β-amanitin, γ-amanitin, ε-amanitin, amanin, amaninamide, amanullin, amanullinic acid, and proamanullin. Formula (III) is as follows:

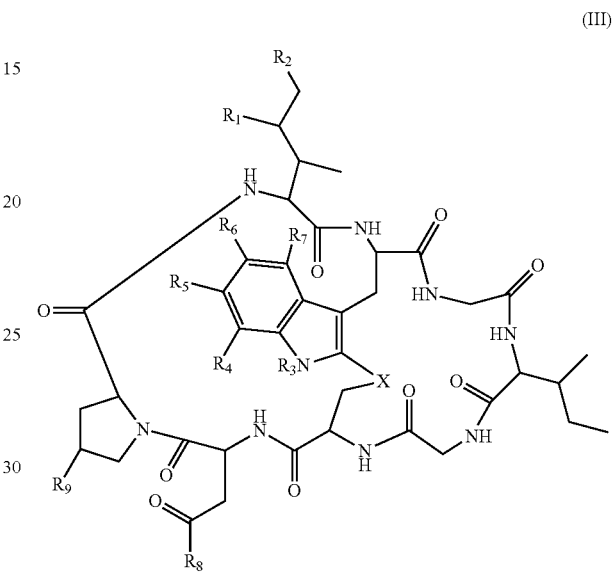

(III)

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocyclolalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —SO$_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

For instance, in one embodiment, amatoxins useful in conjunction with the compositions and methods described herein include compounds according to formula (IIIA), below:

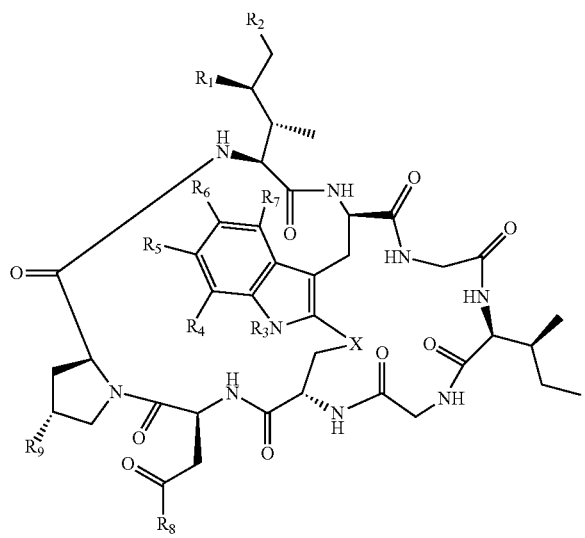

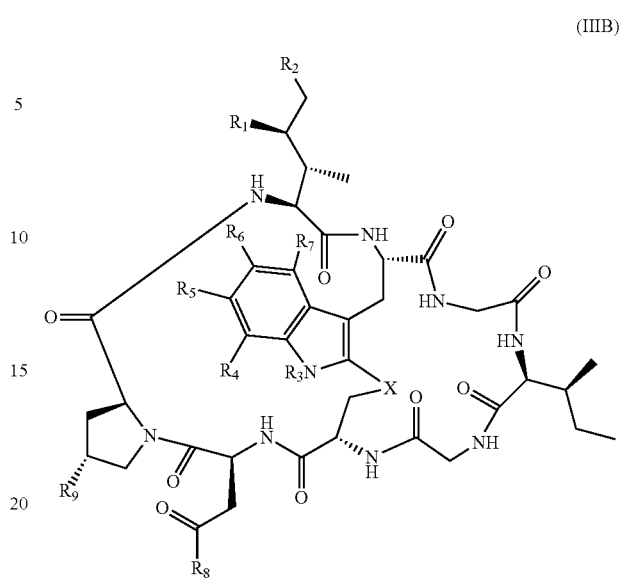

(IIIB)

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocyclolalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_0$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

In one embodiment, amatoxins useful in conjunction with the compositions and methods described herein also include compounds according to formula (IIIB), below:

wherein $R_1$ is H, OH, or $OR_A$;

$R_2$ is H, OH, or $OR_B$;

$R_A$ and $R_B$, when present, together with the oxygen atoms to which they are bound, combine to form an optionally substituted 5-membered heterocyclolalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —$SO_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_8$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

As described herein, amatoxins may be conjugated to an antibody, or an antigen-binding fragment thereof, for instance, by way of a linker moiety. Exemplary methods of amatoxin conjugation and linkers useful for such processes are described in the section entitled "Linkers for chemical conjugation," as well as in Table 1, below. Exemplary linker-containing amatoxins useful for conjugation to an antibody, an antigen-binding fragment, in accordance with the compositions and methods described herein are shown in structural formulas (I), (IA), (IB), (II), (IIA), and (IIB) recited herein.

As used herein, the term "antibody" refers to an immunoglobulin molecule that specifically binds to, or is immunologically reactive with, a particular antigen. Examples of antibodies include polyclonal, monoclonal, genetically engineered, and otherwise modified forms of antibodies, including but not limited to chimeric antibodies, humanized antibodies, heteroconjugate antibodies (e.g., bi- tri- and quad-specific antibodies, diabodies, triabodies, and tetrabodies), and antigen binding fragments of antibodies, including, for example. Fab', F(ab')$_2$, Fab, Fv, rIgG, and scFv fragments. As used herein, the Fab and F(ab')$_2$ fragments refer to antibody fragments that lack the Fc fragment of an intact antibody. Examples of these antibody fragments are described herein.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains. CH1, CH2 and CH3. Each light chain is comprised of a light chain variable region (abbreviated herein as LCVR or VL) and a light chain constant region. The light chain constant region is comprised of one domain, CL. The VH, and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order; FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding fragment," as used herein, refers to a molecule other than an intact antibody that comprises a portion of an intact antibody and that binds the antigen to which the intact antibody binds. The antigen-binding function of an antibody can be performed by fragments of a full-length antibody. The antibody fragments can be, for example, a Fv, Fab, Fab', F(ab')$_2$, scFv, diabody, single chain antibody molecules (e.g., scFv), a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment that consists of a $V_H$ domain (see, e.g., Ward et al., Nature 341:544-546, 1989); (vii) a dAb which consists of a $V_H$ or a $V_L$ domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, $V_1$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, for example. Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "anti-CD5 antibody" or "an antibody that binds to CD5" refers to an antibody that specifically binds to CD5. An antibody "which binds" an antigen of interest, i.e., CD5, is one capable of binding that antigen with sufficient affinity such that the antibody is useful in targeting a cell expressing the antigen. In a preferred embodiment, the antibody specifically binds to human CD5 (hCD5), the amino acid sequence of which is described in SEQ ID NO: 261.

As used herein, the term "bispecific antibody" refers to a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553. The two binding sites of a bispecific antibody will bind to two different epitopes, which may reside on the same or different protein targets. For instance, one of the binding specificities can be directed towards a T cell surface antigen, such as CD5, the other can be for a different T cell surface antigen or another cell surface protein, such as a receptor or receptor subunit involved in a signal transduction pathway that potentiates cell growth, among others.

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each comprise four framework regions that primarily adopt a β-sheet configuration, connected by three CDRs, which form loops that connect, and in some cases form part of, the -sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, MD., 1987). As used herein, numbering of immunoglobulin amino acid residues is performed according to the immunoglobulin amino acid residue numbering system of Kabat et al., unless otherwise indicated.

As used herein, the terms "condition" and "conditioning" refer to processes by which a patient is prepared for receipt of a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation. According to the methods described herein, a patient may be conditioned for hematopoietic stem cell transplant therapy by administration to the patient of an antibody or antigen-binding fragment thereof capable of binding an antigen expressed by T cells, such as CD5. As described herein, the anti-CD5 antibody may be covalently conjugated to a cytotoxin so as to form an antibody-drug conjugate (ADC). Administration of an antibody, antigen-binding fragment thereof, or antibody-drug conjugate capable of binding one or more of the foregoing antigens to a patient in need of hematopoietic stem cell transplant therapy can promote the engraftment of a hematopoietic stem cell graft, for example, by selectively depleting endogenous immune cells, such as CD5+ T cells (e.g., CD4+ and/or CD8+ T cells), CD5+ B cells, and/or CD5+ NK cells that cross-react with one or more non-self antigens expressed by a hematopoietic stem cell, such as one or more non-self MHC antigens expressed by the hematopoietic stem cell graft. This selective depletion of immune cells in turn prevents or reduces the likelihood of graft rejection following transplantation of an exogenous (for instance, an autologous, allogeneic, or syngeneic) hematopoietic stem cell graft.

As used herein, the term "conjugate" refers to a compound formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules (e.g., an anti-CD5 antibody and a cytotoxin) bound to one another. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, antigen-binding fragment thereof, or antibody, such as an antibody, antigen-binding fragment thereof, or antibody specific for CD5 known in the art or described herein. Examples of suitably reactive substituents include a nucleophile/electrophile pair (e.g., a thiol/haloalkyl pair, an amine/carbonyl pair, or a thiol/α,β-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, "CRU (competitive repopulating unit)" refers to a unit of measure of long-term engrafting stem cells, which can be detected after in-vivo transplantation.

As used herein, "drug-to-antibody ratio" or "DAR" refers to the number of cytotoxins, e.g., amatoxin, attached to the antibody of an ADC. The DAR of an ADC can range from 1 to 8, although higher loads are also possible depending on the number of linkage sites on an antibody. Thus, in certain embodiments, an ADC described herein has a DAR of about 1, 2, 3, 4, 5, 6, 7, or 8.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies comprising three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al., Proc. Natl. Acad. Sci. USA 90:6444-48, 1993).

As used herein, a "dual variable domain immunoglobulin" ("DVD-Ig") refers to an antigen binding protein that combines the target-binding variable domains of two antibodies by way of linkers to create a tetravalent, dual-targeting single agent (see, for example, Gu et al., Meth. Enzymol., 502:25-41, 2012).

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T lymphocyte (e.g., a CD4+ or CD8+ T lymphocyte), or B lymphocyte) that is found naturally in a particular organism, such as a human patient, for instance, a human patient undergoing hematopoietic stem cell transplant therapy as described herein.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "excipient" refers to a substance formulated alongside the active ingredient of a medication. They may be included, for example, for the purpose of long-term stabilization, or to confer a therapeutic enhancement on the active ingredient in the final dosage form.

As used herein, the term "exogenous" describes a substance, such as a molecule, cell, tissue, or organ (e.g., a T cell, hematopoietic stem cell, or a cell of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T lymphocyte, or B lymphocyte) that is not found naturally in a particular organism, such as a human patient. Exogenous substances include those that are provided from an external source to an organism or to cultured matter extracted therefrom.

As used herein, the term "framework region" or "FW region" includes amino acid residues that are adjacent to the CDRs of an antibody or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

The terms "full length antibody," "intact antibody," and "whole antibody" are used herein interchangeably to refer to antibody generally comprising at least two full-length heavy chains and two full-length light chains, but in some instances may include fewer chains such as antibodies naturally occurring in camelids which may comprise only heavy chains.

As used herein, the term "hematopoietic stem cells" ("HSCs") refers to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B cells and T cells). Such cells may include CD34+ cells. CD34+ cells are immature cells that express the CD34 cell surface marker. In humans, CD34+ cells are believed to include a subpopulation of cells with the stem cell properties defined above, whereas in mice, HSCs are CD34−. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38−, CD45RA−, CD90+, CD49F+, and lin− (negative for mature lineage markers, including CD5, CD3, CD4, CD7, CD8, CD10, CD11B, CD19, CD20, CD56, and CD235A). In mice, bone marrow LT-HSCs are CD34−, SCA-1+, C-kit+, CD135−, Slamfl/CD150+, CD48−, and lin− (negative for mature lineage markers, including Ter119, CD11b, Gr1, CD3, CD4, CD8, B220, and IL7ra), whereas ST-HSCs are CD34+, SCA-1+, C-kit+, CD135−, Slamfl/CD150+, and lin− (negative for mature lineage markers, including Ter119, CD11b, Gr1, CD3, CD4, CD8, B220, and IL7ra). In addition, ST-HSCs are less quiescent and more proliferative than LT-HSCs under homeostatic conditions. However, LT-HSC have greater self-renewal potential (i.e., they survive throughout adulthood, and can be serially transplanted through successive recipients), whereas ST-HSCs have limited self-renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B cells and T cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the terms "Major histocompatibility complex antigens" ('MHC', also referred to as "human leukocyte antigens" ("HLA") in the context of humans) refer to proteins expressed on the cell surface that confer a unique antigenic identity to a cell. MHC/HLA antigens are target molecules that are recognized by T cells and NK cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR. DP, and DO in humans) are involved in reactions between lymphocytes and antigen presenting cells. Both have been implicated in the rejection of transplanted organs. An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules. The genes commonly used for HLA typing are the six MHC Class I and Class proteins, two alleles for each of HLA-A; HLA-B and HLA-DR. The HLA genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA-matched" refers to a donor-recipient pair in which none of the HLA antigens are mismatched between the donor and recipient, such as a donor providing a hematopoietic stem cell graft to a recipient in need of hematopoietic stem cell transplant therapy. HLA-matched (i.e., where all of the 6 alleles are matched) donor-recipient pairs have a decreased risk of graft rejection, as endogenous T cells and NK cells are less likely to recognize the incoming graft as foreign, and are thus less likely to mount an immune response against the transplant.

As used herein, the term "HLA-mismatched" refers to a donor-recipient pair in which at least one HLA antigen, in particular with respect to HLA-A, HLA-B and HLA-DR, is mismatched between the donor and recipient, such as a donor providing a hematopoietic stem cell graft to a recipient in need of hematopoietic stem cell transplant therapy. In some embodiments, one haplotype is matched and the other is mismatched. HLA-mismatched donor-recipient pairs may have an increased risk of graft rejection relative to HLA-matched donor-recipient pairs, as endogenous T cells and NK cells are more likely to recognize the incoming graft as foreign in the case of an HLA-mismatched donor-recipient pair, and such T cells and NK cells are thus more likely to mount an immune response against the transplant.

As used herein, the term "human antibody" refers to an antibody in which substantially every part of the protein (for example, all CDRs, framework regions, $C_L$, $C_H$ domains (e.g., $C_H1$, $C_H2$, $C_H3$), hinge, and $V_L$ and $V_H$ domains) is substantially non-immunogenic in humans, with only minor sequence changes or variations. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO1998/24893; WO1992/01047; WO1996/34096; WO1996/33735; U.S. Pat. Nos. 5,413,923; 5,625, 126; 5,633,425; 5,569,825; 5,661,016; 5,545,806; 5,814, 318; 5,885,793; 5,916,771; and 5,939,598). In one embodiment, a human antibody is made using recombinant methods such that the glycosylation pattern of the antibody is different than an antibody having the same sequence if it were to exist in nature.

As used herein, the term "humanized" antibody refers to a chimeric antibody generally comprising amino acid sequences from non-human CDRs and human framework regions. In one embodiment, a humanized antibody is a human antibody (recipient antibody) in which residues from the CDRs of the recipient are replaced by residues from the CDRs of a non-human species (donor antibody) such as mouse, rat, rabbit, or nonhuman primate having the desired specificity, affinity, and/or capacity. In general, a humanized antibody contains substantially all of at least one, and typically two, variable domains, in which all or substantially all of the CDR regions correspond to those of a non-human immunoglobulin. All or substantially all of the FW regions may also be those of a human immunoglobulin sequence. The humanized antibody can also comprise at least a portion of an immunoglobulin constant region (Fc), typically that of a human immunoglobulin consensus sequence. Methods of antibody humanization are known in the art and have been described, for example, in Riechmann et al., Nature 332: 323-327, 1988; U.S. Pat. Nos. 5,530,101; 5,585,089; 5,693, 761; 5,693,762; and 6,180.370.

As used herein, the term "immune cell" refers to a cell of the immune system that participates in the mounting and maintaining of an innate or adaptive immune response. Immune cells include lymphocytes that contain a receptor that specifically binds, and mounts an immune response against, an antigen of interest, such as a self antigen in the case of an autoimmune cell. Exemplary immune cells include mast cells, basophils, neutrophils, eosinophils, microglia, granulocytes, monocytes, antigen-presenting cells, macrophages, dendritic cells, natural killer cells, T lymphocytes, and B lymphocytes.

As used herein, patients that are "in need of" a hematopoietic stem cell transplant include patients that exhibit a defect or deficiency in one or more blood cell types, as well as patients having a stem cell disorder. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B cells and T cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a non-malignant hemoglobinopathy that may cause a defect or deficiency in one or more blood cell types, such as sickle cell anemia, thalassemia, Fanconi anemia, and Wiskott-Aldrich syndrome. The subject may be one that is suffering from adenosine deaminase severe combined immunodeficiency (ADA SCID), HIV/AIDS, metachromatic leukodystrophy. Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as a malignancy selected from the group consisting of hematologic cancers (e.g., leukemia, lymphoma, multiple myeloma, or myelodysplastic syndrome) and neuroblastoma. In some embodiments, the subject has or is otherwise affected by a metabolic disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may be one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T lymphocytes, and B lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

The term "isolated" when used in the context of a protein, e.g., an antibody, refers to a protein that by virtue of its origin or source of derivation is not associated with naturally associated components that accompany it in its native state; is substantially free of other proteins from the same species; is expressed by a cell from a different species; or does not occur in nature. Thus, a protein that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "monoclonal antibody" or "mAb" refers to an antibody obtained from a population of substantially homogeneous antibodies, i.e., the individual antibodies comprising the population are identical and/or bind to the same epitope, except for possible variant antibodies, e.g., naturally occurring mutations or variants arising during production of a monoclonal antibody preparation, where such variants may be present in minor amounts. In contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "pharmaceutical composition" means a mixture containing a therapeutic compound to be administered to a subject, such as a mammal, e.g., a human, in order to prevent, treat or control a particular disease or condition affecting the mammal, such as an autoimmune disorder, cancer, or blood disorder, among others, e.g., as described herein.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "rejection" in the context of a transplant, such as a hematopoietic stem cell graft, refers to the process by which a recipient mounts an immune response against an incoming transplant, thereby reducing the ability of the transplanted matter (e.g., hematopoietic stem cells) to persist in the recipient. Rejection of a transplanted graft, such as a hematopoietic stem cell graft, can be quantified, for instance, by measuring the quantity or concentration of transplanted cells in various samples isolated from a patient at distinct time points following transplantation. A finding that the quantity or concentration of transplanted cells in samples isolated from the patient diminishes over time, for instance, by 20%, 25%, 30%, 35%, 40%, 56%, 50%, 55%, 60%, 65%, 70%, 75%, 80%, 85%, 90%, 95%, or more, indicates that the patient is suffering from graft rejection. Conversely, a finding that the quantity or concentration of transplanted cells in samples isolated from the patient remains stable over time, for instance, by being diminished by less than 20%, 15%, 10%, 5%, or fewer, indicates that the patient is not suffering from graft rejection. Alternatively, graft rejection can be quantified by measuring the quantity or concentration of immune cells, such as T cells and/or NK cells, that cross-react with MHC antigens expressed by the transplanted cells in various samples isolated from a patient at distinct time points following transplantation. A finding that the quantity or concentration of immune cells, such as T cells and/or NK cells, that cross-react with MHC antigens expressed by the transplanted cells in samples isolated from the patient increases over time, for instance, by 10%, 15%, 20%, 25%, 30%, 35%, 40%, 56%, 50%, 55%, 60%, 65%, 70%, 75%, 80%, 85%, 90%, 95%, 100%, 200%, 300%, or more, indicates that the patient is suffering from graft rejection. Conversely, a finding that the quantity or concentration of immune cells, such as T cells and/or NK cells, that cross-react with MHC antigens expressed by the transplanted cells in samples isolated from the patient diminishes over time, for instance, by 20%, 25%, 30%, 35%, 40%, 56%, 50%, 55%, 60%, 65%, 70%, 75%, 80%, 85%, 90%, 95%, or more, indicates that the patient is not suffering from graft rejection.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

The terms "specific binding" or "specifically binds" in reference to the interaction of an antibody, or antibody fragment, with a second chemical species, means that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In one embodiment, an antibody specifically binds to a target, e.g., CD5, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to CD5" or "specifically binds to CD5," as used herein, refers to an antibody or that binds to CD5 and has a dissociation constant ($K_D$) of $1.0 \times 10^{-7}$ M or less, as determined by surface plasmon resonance. In one embodiment, $K_D$ is determined according to standard bio-layer interferometery (BLI). It shall be understood, however, that the antibody may be capable of specifically binding to two or more antigens which are related in sequence. For example, in one embodiment, an antibody can specifically bind to both human and a non-human (e.g., mouse or non-human primate) orthologs of CD5.

As used herein, the terms "subject" and "patient" refer to a mammal, such as a human, that receives treatment for a particular disease or condition as described herein. For instance, a patient, such as a human patient, may be one that is suffering from an autoimmune disease described herein, and may be administered an anti-CD5 antibody or antibody-drug conjugate described herein so as to (i) deplete a population of autoimmune cells (e.g., a population of autoimmune CD5+ T cells, B cells, and/or NK cells) and/or (ii) deplete a population of CD5+ immune cells (e.g., CD5+ T cells, B cells, and/or NK cells that cross-react with a non-self antigen expressed by hematopoietic stem cells, such as a non-self MHC antigen expressed by a hematopoietic stem cell graft, thereby preventing or reducing the likelihood of graft rejection prior to hematopoietic stem cell transplant therapy.

As used herein, the phrase "substantially cleared from the blood" refers to a point in time following administration of a therapeutic agent (such as an anti-CD5 antibody, or an antigen-binding fragment thereof) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, or antibody fragments, such as ELISA-based detection assays known in the art or described herein. Additional assays that can be used to detect antibodies, and antibody fragments, include immunoprecipitation techniques and immunoblot assays, among others known in the art.

As used herein, the phrase "stem cell disorder" broadly refers to any disease, disorder, or condition that may be treated or cured by conditioning a subject's target tissues, for instance, by ablating an endogenous T cell population in a target tissue) and/or by engrafting or transplanting stem cells in a subject's target tissues. For example, Type I diabetes patients have been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, Wiskott-Aldrich syndrome, ADA SCID, HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as a malignancy selected from the group consisting of hematologic cancers (e.g., leukemia, lymphoma, multiple myeloma, or myelodysplastic syndrome) and neuroblastoma. In some embodiments, the subject has or is otherwise affected by a metabolic disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the terms "treat" or "treatment" refer to therapeutic treatment, in which the object is to prevent or slow down (lessen) an undesired physiological change or disorder or to promote a beneficial phenotype in the patient being treated. Beneficial or desired clinical results include, but are not limited to, a reduction in the quantity of autoimmune cells present in a sample isolated from the patient, such as a population of CD5+ T cells, B cells, and/or NK cells that cross-react with a self antigen in the case of treating an autoimmune disorder directly, or an antigen expressed by hematopoietic stem cells prior to hematopoietic stem cell transplantation in the case of treating an autoimmune disease by administration an anti-CD5 antibody, or antigen-binding fragment thereof, and a hematopoietic stem cell graft. Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myoblast, basophil, neutrophil, eosinophil, microglial cell, granulocyte, monocyte, osteoclast, antigen-presenting cell, macrophage, dendritic cell, natural killer cell, T lymphocyte, or B lymphocyte, following conditioning therapy and subsequent hematopoietic stem cell transplant therapy.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "alkyl" refers to a straight- or branched-chain alkyl group having, for example, from 1 to 20 carbon atoms in the chain. Examples of alkyl groups include methyl, ethyl, n-propyl, isopropyl, butyl, isobutyl, sec-butyl, tert-butyl, pentyl, isopentyl, tert-pentyl, hexyl, isohexyl, and the like.

As used herein, the term "alkylene" refers to a straight- or branched-chain divalent alkyl group. The divalent positions may be on the same or different atoms within the alkyl chain. Examples of alkylene include methylene, ethylene, propylene, isopropylene, and the like.

As used herein, the term "heteroalkyl" refers to a straight or branched-chain alkyl group having, for example, from 1 to 20 carbon atoms in the chain, and further containing one or more heteroatoms (e.g., oxygen, nitrogen, or sulfur, among others) in the chain.

As used herein, the term "heteroalkylene" refers to a straight- or branched-chain divalent heteroalkyl group. The divalent positions may be on the same or different atoms within the heteroalkyl chain. The divalent positions may be one or more heteroatoms.

As used herein, the term "alkenyl" refers to a straight- or branched-chain alkenyl group having, for example, from 2 to 20 carbon atoms in the chain. Examples of alkenyl groups include vinyl, propenyl, isopropenyl, butenyl, tert-butylenyl, hexenyl, and the like.

As used herein, the term "alkenylene" refers to a straight- or branched-chain divalent alkenyl group. The divalent positions may be on the same or different atoms within the alkenyl chain. Examples of alkenylene include ethenylene, propenylene, isopropenylene, butenylene, and the like.

As used herein, the term "heteroalkenyl" refers to a straight- or branched-chain alkenyl group having, for example, from 2 to 20 carbon atoms in the chain, and further containing one or more heteroatoms (e.g., oxygen, nitrogen, or sulfur, among others) in the chain.

As used herein, the term "heteroalkenylene" refers to a straight- or branched-chain divalent heteroalkenyl group. The divalent positions may be on the same or different atoms within the heteroalkenyl chain. The divalent positions may be one or more heteroatoms.

As used herein, the term "alkynyl" refers to a straight- or branched-chain alkynyl group having, for example, from 2 to 20 carbon atoms in the chain. Examples of alkynyl groups include propargyl, butynyl, pentynyl, hexynyl, and the like.

As used herein, the term "alkynylene" refers to a straight- or branched-chain divalent alkynyl group. The divalent positions may be on the same or different atoms within the alkynyl chain.

As used herein, the term "heteroalkynyl" refers to a straight- or branched-chain alkynyl group having, for example, from 2 to 20 carbon atoms in the chain, and further containing one or more heteroatoms (e.g., oxygen, nitrogen, or sulfur, among others) in the chain.

As used herein, the term "heteroalkynylene" refers to a straight- or branched-chain divalent heteroalkynyl group. The divalent positions may be on the same or different atoms within the heteroalkynyl chain. The divalent positions may be one or more heteroatoms.

As used herein, the term "cycloalkyl" refers to a monocyclic, or fused, bridged, or spiro polycyclic ring structure that is saturated and has, for example, from 3 to 12 carbon ring atoms. Examples of cycloalkyl groups include cyclopropyl, cyclobutyl, cyclopentyl, cyclohexyl, cycloheptyl, cyclooctyl, bicyclo[3.1.0]hexane, and the like.

As used herein, the term "cycloalkylene" refers to a divalent cycloalkyl group. The divalent positions may be on the same or different atoms within the ring structure. Examples of cycloalkylene include cyclopropylene, cyclobutylene, cyclopentylene, cyclohexylene, and the like.

As used herein, the term "heterocycloalkyl" refers to a monocyclic, or fused, bridged, or spiro polycyclic ring structure that is saturated and has, for example, from 3 to 12 ring atoms per ring structure selected from carbon atoms and heteroatoms selected from, e.g., nitrogen, oxygen, and sulfur, among others. The ring structure may contain, for example, one or more oxo groups on carbon, nitrogen, or sulfur ring members. Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

As used herein, the term "heterocycloalkylene" refers to a divalent heterocylolalkyl group. The divalent positions may be on the same or different atoms within the ring structure. As used herein, the term "aryl" refers to a monocyclic or multicyclic aromatic ring system containing, for example, from 6 to 19 carbon atoms. Aryl groups include, but are not limited to, phenyl, fluorenyl, naphthyl, and the like. The divalent positions may be one or more heteroatoms.

As used herein, the term "arylene" refers to a divalent aryl group. The divalent positions may be on the same or different atoms.

As used herein, the term "heteroaryl" refers to a monocyclic heteroaromatic, or a bicyclic or a tricyclic fused-ring heteroaromatic group in which one or more ring atoms is a heteroatom, e.g., nitrogen, oxygen, or sulfur. Heteroaryl groups include pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-trazinyl, 1,2,3-trazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyrdyl, pyrido[4,3-b]pyrdyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heteroarylene" refers to a divalent heteroaryl group. The divalent positions may be on the same or different atoms. The divalent positions may be one or more heteroatoms.

Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", "heterocycloalkylene". "aryl," "arylene", "heteroaryl", and "heteroarylene" groups can optionally be substituted with, for example, from 1 to 5 substituents selected from the group consisting of alkyl, alkenyl, alkynyl, cycloalkyl, heterocycloalkyl, alkyl aryl, alkyl heteroaryl, alkyl cycloalkyl, alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. Typical substituents include, but are not limited to, —X, —R, —OH, —OR, —SH, —SR, $NH_2$, —NHR, —N(R)$_2$, —N$^+$(R)$_3$, —CX$_3$, —CN, —OCN, —SCN, —NCO, —NCS, —NO, —NO$_2$, —N$_3$, —NC(=O)H, —NC(=O)R, —C(=O)H, —C(=O)R, —C(=O)NH$_2$, —C(=O)N(R)$_2$, —SO$_3$—, —SO$_3$H, —S(=O)$_2$R, —OS(=O)$_2$OR, —S(=O)$_2$NH$_2$—S(=O)$_2$N(R)$_2$, —S(=O)R, —OP(=O)(OH)$_2$, —OP(=O)(OR)$_2$, —P(=O)(OR)$_2$, —PO$_3$, —PO$_3$H$_2$, —C(=O)X, —C(=S)R, —CO$_2$H, —CO$_2$R, —CO$_2$—, —C(=S)OR, —C(=O)SR, —C(=S)SR, —C(=O)NH$_2$, —C(=O)N(R)$_2$, —C(=S)NH$_2$, —C(=S)N(R)$_2$, —C(=NH)NH$_2$, and —C(=NR)N(R)$_2$; wherein each X is independently selected for each occasion from F, Cl, Br, and I; and each R is independently selected for each occasion from alkyl, aryl, heterocycloalkyl or heteroaryl, protecting group and prodrug moiety. Wherever a group is described as "optionally substituted," that group can be substituted with one or more of the above substituents, independently for each occasion. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated Anti-CD5 Antibodies The present invention is based in part on the discovery that anti-CD5 antibodies, or antigen-binding fragments thereof, can be used to treat cancers and autoimmune diseases directly, for instance, due to the ability of such agents to kill CD5+ cancer cells (e.g., CD5+ leukemic cells) and CD5+ autoimmune cells (e.g., CD5+ autoimmune T cells, B cells, and/or NK cells). In particular, an anti-CD5 antibody described herein is conjugated to a cytotoxin via a linker. Thus, where anti-CD5 antibodies are described, conjugates thereof are also contemplated unless otherwise indicated.

The invention is additionally based in part on the discovery that antibodies, or antigen-binding fragments thereof, capable of binding CD5 can be used as therapeutic agents to promote the engraftment of transplanted hematopoietic stem cells in a patient in need of transplant therapy by preventing or reducing the likelihood of immune cell-mediated graft rejection. For instance, anti-CD5 antibodies, and antigen binding fragments, can bind cell-surface CD5 expressed by immune cells such as T cells, B cells, or NK cells that cross-react with, and mount an immune response against, non-self hematopoietic stem cell antigens, such as non-self MHC antigens expressed by a hematopoietic stem cell graft. The binding of such antibodies, and antigen-binding fragments, to hematopoietic stem cell-specific CD5+ immune cells can induce death of the bound immune cell, for instance, by antibody-dependent cell-mediated cytotoxicity or by the action of a cytotoxic agent that is conjugated to the antibody, or the antigen-binding fragment thereof. The depletion of a population of CD5+ immune cells that cross-react with non-self hematopoietic stem cells can thus facilitate the engraftment of hematopoietic stem cell transplants in a patient in need thereof by attenuating the ability of the recipient's immune system to mount an immune response against the incoming graft. In this way, a patient suffering from a stem cell disorder, cancer, autoimmune disease, or other blood disorder described herein can be treated, as a hematopoietic stem cell transplant can be provided to a subject in order to repopulate a lineage of cells that is defective and/or deficient in the subject. The subject may be deficient in a population of cells due to, for instance, chemotherapy that has been administered to the subject with the aim of eradicating cancerous cells but that has, in the process, depleted healthy hematopoietic cells as well.

For example, the invention thus provides compositions and methods of promoting the engraftment of transplanted hematopoietic stem cells by administration of an antibody, or an antigen-binding fragment thereof, capable of binding an antigen expressed by T cells. This administration can cause the selective depletion of a population of endogenous T cells, such as CD4+ and CD8+ T cells. This selective depletion of T cells can, in turn, prevent graft rejection following transplantation of an exogenous (for instance, an autologous, allogeneic, or syngeneic) hematopoietic stem cell graft. For instance, the selective depletion of CD4+ and/or CD8+ T cells using an anti-CD5 antibody, antigen-binding fragment, antibody-drug conjugate, or antibody-drug conjugate as described herein can attenuate a T cell-mediated immune response that may occur against a transplanted hematopoietic stem cell graft. The invention is based in part on the discovery that antibodies, and antigen-binding fragments thereof, capable of binding CD5 can be administered to a patient in need of hematopoietic stem cell transplant therapy in order to promote the survival and engraftment potential of transplanted hematopoietic stem cells.

Engraftment of hematopoietic stem cell transplants due to the administration of anti-CD5 antibodies, or antigen-binding fragments thereof, can manifest in a variety of empirical measurements. For instance, engraftment of transplanted hematopoietic stem cells can be evaluated by assessing the quantity of competitive repopulating units (CRU) present within the bone marrow of a patient following administration of an antibody or antigen-binding fragment thereof capable of binding CD5 and subsequent administration of a hematopoietic stem cell transplant. Additionally, one can observe engraftment of a hematopoietic stem cell transplant by incorporating a reporter gene, such as an enzyme that catalyzes a chemical reaction yielding a fluorescent, chromophoric, or luminescent product, into a vector with which the donor hematopoietic stem cells have been transfected and subsequently monitoring the corresponding signal in a tissue into which the hematopoietic stem cells have homed, such as the bone marrow. One can also observe hematopoietic stem cell engraftment by evaluation of the quantity and survival of hematopoietic stem and progenitor cells, for instance, as determined by fluorescence activated cell sorting (FACS) analysis methods known in the art. Engraftment can also be determined by measuring white blood cell counts in peripheral blood during a post-transplant period, and/or by measuring recovery of marrow cells by donor cells in a bone marrow aspirate sample.

The sections that follow provide a description of antibodies, or antigen-binding fragments thereof, that can be administered to a patient in need of hematopoietic stem cell transplant therapy in order to promote engraftment of hematopoietic stem cell grafts, as well as methods of administering such therapeutics to a patient prior to hematopoietic stem cell transplantation.

Exemplary Antibodies

Compositions and methods described herein include an antibody, or fragment thereof, that specifically binds to human CD5. Human CD5 is also referred to as LEU1 or T1. Human CD5 is a type-I transmembrane glycoprotein found on the surface of thymocytes, T lymphocytes and a subset of B lymphocytes. Two isoforms of human CD5 have been identified. Isoform 1 contains 438 amino acids and is described in Jones. et al. (1988) Nature 323 (6086), 346-349 and below (NCBI Reference Sequence: NP_001333385.1):

(SEQ ID NO: 261)
MVCSQSWGRS SKQWEDPSQASKVCQRLNCG VPLSLGPFLV TYTPQSS

IICYGQLGSFSNCSHSRNDMCHS LGLTCLEPQKTTPPTTRPPPTTTPEP

TAPP RLQLVAQSGGQHCAGVVEFYSGSLGGTISY EAQDKTQDLE NFL

CNNLQCG SFLKHLPETE AGRAQDPGEPREHQPLPIQWKIQNSSCTSL

EHCFRKIKPQ KSGRVLALLC SGFQPKVQSR LVGGSSICEGTVEVRQG

AQWAALCDSSSAR SSLRWEEVCR EQQCGSVNSY RVLDAGDPTS RGL

FCPHQKLSQCHELWERNSYCKKVFVTCQDPNPAGLAAGTVASIILAL VL

LVVLLVVC GPLAYKKLVKKFRQKKQRQWIGPTGMNQNM SFHRNHTATV

RSHAENPTAS HVDNEYSQPP RNSHLSAYPALEGALHRSSMQPDNSSDS

DY DLHGAQRL

T cells have been shown to express CD5, which is a cell adhesion molecule and has been implicated both in the proliferative response of activated T cells and in T cell helper function. It has also been shown to function as a receptor, delivering co-stimulatory signals to T cells by interacting with CD72, a cell surface protein exclusive to B cells. Antibodies, or antigen-binding fragments thereof, that bind CD5 may suppress T cell activation and T cell-mediated immune responses against hematopoietic stem cell grafts, for example, by inhibiting the interaction between CD5 and CD72. Antibodies, and antigen-binding fragments thereof, that bind CD5 can also be used to kill CD5+ T cells directly, for instance, by conjugating the antibody, or antigen-binding fragment thereof, to a cytotoxin (such as a cytotoxin described herein or known in the art) or by using an unconjugated antibody, or antigen-binding fragment thereof, capable of recruiting complement proteins to the T cell.

Additionally, subsets of activated B cells have been shown to express CD5, and this expression pattern is particularly common among autoreactive B cells (Werner-Favre et al., European Journal of Immunology 19:1209-1231 (1989), the disclosure of which is incorporated herein by reference in its entirety). CD5 has also been shown to be expressed by subsets of NK cells; particularly among patients that have multiple myeloma have been shown to harbor populations of low density CD5+ (CD5 LOW+) NK cells, and this surface antigen has been implicated in NK cell activation (Ishiyama et al., Anticancer Research 14:725-730 (1994), the disclosure of which is incorporated herein by reference in its entirety). Antibodies, or antigen-binding fragments thereof, that specifically bind CD5 can thus be used to attenuate the activation of B cells and NK cells. Antibodies, or antigen-binding fragments thereof, that bind CD5 can also be used to kill CD5+ B cells and NK cells directly, for instance, by conjugating the antibody, or antigen-binding fragment thereof, to a cytotoxin (such as a cytotoxin described herein or known in the art) or by using an unconjugated antibody, or antigen-binding fragment thereof, capable of recruiting complement proteins to the B cell or NK cell.

The present invention encompasses antibodies, and antigen-binding fragments thereof, that specifically bind to a CD5 polypeptide, e.g., a human CD5 polypeptide, and uses thereof. In an exemplary embodiment, the antibody, or antigen-binding fragment thereof, that specifically binds to a CD5 polypeptide comprises a heavy chain variable region and a light chain variable region.

In one embodiment, the heavy chain variable region comprises one or more complementarity determining regions (CDRs). In one embodiment, the heavy chain variable region comprises a VH CDR1 comprising the amino acid sequence of SEQ ID NO: 17. In one embodiment, the heavy chain variable region comprises a VH CDR2 comprising the amino acid sequence of SEQ ID NO: 18. In one embodiment, the heavy chain variable region comprises a VH CDR3 comprising the amino acid sequence of SEQ ID NO: 19. In one embodiment, the heavy chain variable region comprises one or more VH CDRs selected from the group consisting of SEQ ID NO: 17, SEQ ID NO: 18, and SEQ ID NO: 19. In one embodiment, the heavy chain variable region comprises two or more VH CDRs selected from the group consisting of SEQ ID NO: 17, SEQ ID NO: 18, and SEQ ID NO: 19. In one embodiment, the heavy chain variable region comprises a VH CDR1 comprising SEQ ID NO: 17, a VH CDR2 comprising SEQ ID NO: 18, and a VH CDR3 comprising SEQ ID NO: 19.

In one embodiment, the light chain variable region comprises one or more complementarity determining regions (CDRs). In one embodiment, the light chain variable region comprises a VL CDR1 comprising the amino acid sequence of SEQ ID NO: 20. In one embodiment, the light chain variable region comprises a VL CDR2 comprising the amino acid sequence of SEQ ID NO: 21. In one embodiment, the light chain variable region comprises a VL CDR3 comprising the amino acid sequence of SEQ ID NO: 22. In one embodiment, the light chain variable region comprises one or more VL CDRs selected from the group consisting of SEQ ID NO: 20, SEQ ID NO: 21, and SEQ ID NO: 22. In one embodiment, the light chain variable region comprises two or more VL CDRs selected from the group consisting of SEQ ID NO: 20, SEQ ID NO: 21, and SEQ ID NO: 22. In one embodiment, the light chain variable region comprises a VL CDR1 comprising SEQ ID NO: 20, a VL CDR2 comprising SEQ ID NO: 21, and a VL CDR3 comprising SEQ ID NO: 22.

In an exemplary embodiment, the antibody, or antigen-binding fragment thereof, comprises a heavy chain variable region that comprises a VH CDR1 comprising SEQ ID NO: 17, a VH CDR2 comprising SEQ ID NO: 18, and a VH CDR3 comprising SEQ ID NO: 19, and a light chain variable region that comprises a VL CDR1 comprising SEQ ID NO: 20, a VL CDR2 comprising SEQ ID NO: 21, and a VL CDR3 comprising SEQ ID NO: 22.

In certain embodiments, one or more of the CDRs (i.e., one or more heavy chain CDRs having SEQ ID NOs: 17-19, and/or one or more light chain CDRs having SEQ ID NOs: 20-22) can comprise a conservative amino acid substitution (or 2, 3, 4, or 5 amino acid substitutions) while retaining the CD5 specificity of the antibody (i.e., specificity similar to an antibody, or antigen-binding fragment thereof, comprising heavy chain CDRs of SEQ ID NOs: 17 to 19, and light chain CDRs of SEQ ID NOs:20 to 22).

In certain embodiments, the anti-CD5 antibody, or antigen binding fragment thereof, is murine antibody 5D7, or a humanized version thereof. Murine antibody 5D7 binds to human CD5 and is described in US Patent Publication No. 20008/0245027, the contents of which relating to the antibody sequences disclosed therein are incorporated by reference herein. SEQ ID Nos: 29 to 34 described in Table 4 correspond to the CDRs of murine anti-CD5 antibody 5D7. A humanized version of anti-CD5 antibody 5D7 is described in SEQ ID NO: 257 (humanized heavy chain variable region) and SEQ ID NO: 258 (humanized light chain variable region). In one embodiment, the ADCs and uses thereof described herein include an antibody comprising the CDRs set forth in SEQ ID Nos: 29 to 34. In one embodiment, the ADCs and uses thereof described herein include an antibody comprising the heavy and light chain variable regions as set forth in SEQ ID Nos: 257 and 258, respectively.

In one embodiment, the antibody, or antigen-binding fragment thereof, comprises a heavy chain variable region that comprises the amino acid sequence set forth in SEQ ID NO: 257. In another embodiment, the antibody, or antigen-binding fragment thereof, comprises a heavy chain variable region that comprises an amino acid sequence having at least 95% identity to SEQ ID NO: 257, e.g., at least 95%, 96%, 97%, 98%, 99%, or 100% identity to SEQ ID NO: 257. In certain embodiments, an antibody comprises a modified heavy chain (HC) variable region comprising an HC variable domain comprising SEQ ID NO: 257, or a variant of SEQ ID NO: 257, which variant (i) differs from SEQ ID NO: 257 in 1, 2, 3, 4 or 5 amino acids substitutions, additions or deletions; (ii) differs from SEQ ID NO: 257 in at most 5, 4, 3, 2, or 1 amino acids substitutions, additions or deletions; (iii) differs from SEQ ID NO: 257 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 257, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of SEQ ID NO: 257, while retaining the CD5 binding specificity of the antibody, i.e. has a binding specificity similar to an antibody, or antigen-binding fragment thereof, comprising SEQ ID NO: 257.

In one embodiment, the antibody, or antigen-binding fragment thereof, comprises a light chain variable region that comprises the amino acid sequence set forth in SEQ ID NO: 258. In another embodiment, the antibody, or antigen-binding fragment thereof, comprises a light chain variable region that comprises an amino acid sequence having at least 95% identity to SEQ ID NO: 258, e.g., at least 95%, 96%, 97%, 98%, 99%, or 100% identity to SEQ ID NO: 258. In certain embodiments, an antibody comprises a modified light chain (LC) variable region comprising an LC variable domain comprising SEQ ID NO: 258, or a variant of SEQ ID NO: 258, which variant (i) differs from SEQ ID NO: 258 in 1, 2, 3, 4 or 5 amino acids substitutions, additions or deletions; (ii) differs from SEQ ID NO: 258 in at most 5, 4, 3, 2, or 1 amino acids substitutions, additions or deletions; (iii) differs from SEQ ID NO: 258 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 258, wherein in any of (i)-(iv), an amino acid substitution may be a conservative amino acid substitution or a non-conservative amino acid substitution; and wherein the modified light chain variable region can have an enhanced biological activity relative to the light chain variable region of SEQ ID NO: 258, while retaining the CD5 binding specificity of the antibody, i.e., has a binding specificity similar to an antibody, or antigen-binding fragment thereof, comprising SEQ ID NO: 258.

In an exemplary embodiment, the antibody, or antigen-binding fragment thereof, comprises a heavy chain variable region that comprises an amino acid sequence having at least 95% identity to SEQ ID NO: 257, e.g., at least 95%, 96%, 97%, 98%, 99%, or 100% identity to SEQ ID NO: 257, and a light chain variable region that comprises an amino acid sequence having at least 95% identity to SEQ ID NO: 258, e.g., at least 95%, 96%, 97%, 98%, 99%, or 100% identity to SEQ ID NO: 258. In one embodiment, the antibody, or antigen-binding fragment thereof, comprises a heavy chain variable region that comprises SEQ ID NO: 257, and a light chain variable region that comprises SEQ ID NO: 258.

In another embodiment, the anti-CD5 antibody, or antigen-binding fragment thereof, can contain a heavy chain variable region that comprises a VH CDR1 comprising the amino acid sequence of SEQ ID NO: 29. In one embodiment, the heavy chain variable region comprises a VH CDR2 comprising the amino acid sequence of SEQ ID NO: 30. In one embodiment, the heavy chain variable region comprises a VH CDR3 comprising the amino acid sequence of SEQ ID NO: 31. In one embodiment, the heavy chain variable region comprises one or more VH CDRs selected from the group consisting of SEQ ID NO: 29, SEQ ID NO: 30, and SEQ ID NO: 31. In one embodiment, the heavy chain variable region comprises two or more VH CDRs selected from the group consisting of SEQ ID NO: 29, SEQ ID NO: 30, and SEQ ID NO: 31. In one embodiment, the heavy chain variable region comprises a VH CDR1 comprising SEQ ID NO: 29, a VH CDR2 comprising SEQ ID NO: 30, and a VH CDR3 comprising SEQ ID NO: 31.

In one embodiment, the light chain variable region comprises one or more complementarity determining regions (CDRs). In one embodiment, the light chain variable region comprises a VL CDR1 comprising the amino acid sequence of SEQ ID NO: 32. In one embodiment, the light chain variable region comprises a VL CDR2 comprising the amino acid sequence of SEQ ID NO: 33. In one embodiment, the light chain variable region comprises a VL CDR3 comprising the amino acid sequence of SEQ ID NO: 34. In one embodiment, the light chain variable region comprises one or more VL CDRs selected from the group consisting of SEQ ID NO: 32, SEQ ID NO: 33, and SEQ ID NO: 34. In one embodiment, the light chain variable region comprises two or more VL CDRs selected from the group consisting of SEQ ID NO: 32, SEQ ID NO: 33, and SEQ ID NO: 34. In one embodiment, the light chain variable region comprises a VL CDR1 comprising SEQ ID NO: 32, a VL CDR2 comprising SEQ ID NO: 33, and a VL CDR3 comprising SEQ ID NO: 34.

In an exemplary embodiment, the antibody, or antigen-binding fragment thereof, comprises a heavy chain variable region that comprises a VH CDR1 comprising SEQ ID NO: 29, a VH CDR2 comprising SEQ ID NO: 30, and a VH CDR3 comprising SEQ ID NO: 31, and a light chain variable region that comprises a VL CDR1 comprising SEQ ID NO: 32, a VL CDR2 comprising SEQ ID NO: 33, and a VL CDR3 comprising SEQ ID NO: 34.

In certain embodiments, one or more of the CDRs (i.e., one or more heavy chain CDRs having SEQ ID NOs: 29-31, and/or one or more light chain CDRs having SEQ ID NOs: 32-34) can comprise a conservative amino acid substitution (or 2, 3, 4, or 5 amino acid substitutions) while retaining the CD5 specificity of the antibody (i.e., specificity similar to an antibody, or antigen-binding fragment thereof, comprising heavy chain CDRs of SEQ ID NOs: 29 to 31, and light chain CDRs of SEQ ID NOs:32 to 34).

Antibodies and antigen-binding fragments thereof capable of binding CD5 antigen can be identified using techniques known in the art and described herein, such as by immunization, computational modeling techniques, and in vitro selection methods, such as the phage display and cell-based display platforms described below.

Anti-CD5 antibodies that can be used in conjunction with the compositions and methods described herein include those that have one or both of the following variable regions, or an amino acid sequence having at least 85% sequence identity thereto (e.g., an amino acid sequence having 85%, 90%, 95%, 97%, 98%, 99%, or more, sequence identity thereto):

a $V_L$ having the amino acid sequence
(SEQ ID NO: 1)
DIQMTQSPSSMSASLGDRVTITCRASQDINSYLSWFQQKPGKSPKTLIYR

ANRLVDGVPSRFSGSGSGTDYTLTISSLQYEDFGIYYCQQYDESPWTFGG

GTKLEIK;
and a $V_H$ having the amino acid sequence
(SEQ ID NO: 2)
QIQLVQSGPGLKKPGGSVRISCAASGYTFTNYGMNWVKQAPGKGLRWMGW

INTHTGEPTYADDFKGRFTFSLDTSKSTAYLQINSLRAEDTATYFCTRRG

YDWYFDVWGQGTTVTVSS.

Antibodies and antigen-binding fragments thereof containing the foregoing $V_L$ and $V_H$ sequences are described, e.g., in U.S. Pat. No. 5,869,619, the disclosure of which is incorporated herein by reference as it pertains to anti-CD5 antibodies and antigen-binding fragments thereof, such as the he1 antibody. In some embodiments, the anti-CD5 antibody or antigen-binding fragment thereof includes the $V_L$ and $V_H$ chains of SEQ ID NO: 1 and SEQ ID NO: 2. In some embodiments, the anti-CD5 antibody or antigen-binding fragment thereof includes the CDRs contained in the $V_L$ and $V_H$ chains of SEQ ID NO: 1 and SEQ ID NO: 2. In some embodiments, the anti-CD5 antibody or antigen-binding fragment thereof includes the CDRs contained in the $V_L$ and $V_H$ chains of SEQ ID NO: 1 and SEQ ID NO: 2 and the remainder of the $V_L$ and $V_H$ sequences have at least 85% sequence identity (e.g., 85%, 90%, 95%, 97%, 98%, 99%, or greater sequence identity) to the $V_L$ and $V_H$ sequences of SEQ ID NO: 1 and SEQ ID NO: 2.

In some embodiments, the anti-CD5 antibody or antigen-binding fragment thereof includes the following CDRs:
a CDR-H1 having the amino acid sequence GYTFTNY (SEQ ID NO: 3);
a CDR-H2 having the amino acid sequence NTHTGE (SEQ ID NO: 4);
a CDR-H3 having the amino acid sequence RGYDWYFDV (SEQ ID NO: 5);
a CDR-L1 having the amino acid sequence RASQDIN-SYLS (SEQ ID NO: 6);
a CDR-L2 having the amino acid sequence RANRLVD (SEQ ID NO: 7); and
a CDR-L3 having the amino acid sequence QQYDESPWT (SEQ ID NO: 8).

Additional anti-CD5 antibodies that can be used in conjunction with the compositions and methods described herein include those that have one or both of the following variable regions, or an amino acid sequence having at least 85% sequence identity thereto (e.g., an amino acid sequence having 85%, 90%, 95%, 97%, 98%, 99%, or more, sequence identity thereto):

a V_L having the amino acid sequence
(SEQ ID NO: 9)
DIQMTQSPSSLSASVGDRVTITCRASQDINSYLSWFQQKPGKAPKTLIYR

ANRLESGVPSRFSGSGSGTDYTLTIS SLQYEDFGIYYCQQYDESPWTFG

GGTKLEIK;
and a V_H having the amino acid sequence
(SEQ ID NO: 10)
EIQLVQSGGGLVKPGGSVRISCAASGYTFTNYGMNWVRQAPGKGLEWMGW

INTHYGEPTYADSFKGTRTFSLDDSKNTAYLQINSLRAEDTAVYFCTRRG

YDWYFDVWGQGGTTVTVSS.

Antibodies and antigen-binding fragments thereof containing the foregoing $V_L$ and $V_H$ sequences are described, e.g., in U.S. Pat. No. 5,869,619, the disclosure of which is incorporated herein by reference as it pertains to anti-CD5 antibodies and antigen-binding fragments thereof, such as the he3 antibody. In some embodiments, the anti-CD5 antibody or antigen-binding fragment thereof includes the CDRs contained in the $V_L$ and $V_H$ chains of the antibody that includes the Wand $V_H$ chains of SEQ ID NO:3 and SEQ ID NO: 4. In some embodiments, the anti-CD5 antibody or antigen-binding fragment thereof includes the CDRs contained in the $V_L$ and $V_H$ chains of SEQ ID NO:3 and SEQ ID NO: 4 and the remainder of the $V_L$ and $V_H$ sequences have at least 85% sequence identity (e.g., 85%, 90%, 95%, 97%, 98%, 99%, or greater sequence identity) to the $V_L$ and $V_H$ sequences of SEQ ID NO:3 and SEQ ID NO: 4.

In some embodiments, the anti-CD5 antibody or antigen-binding fragment thereof includes the following CDRs:
  a CDR-H1 having the amino acid sequence GYTFTNY (SEQ ID NO: 11);
  a CDR-H2 having the amino acid sequence NTHYGE (SEQ ID NO: 12);
  a CDR-H3 having the amino acid sequence RRGYDWYFDV (SEQ ID NO: 13);
  a CDR-L1 having the amino acid sequence RASQDINSYLS (SEQ ID NO: 14);
  a CDR-L2 having the amino acid sequence RANRLES (SEQ ID NO: 15); and
  a CDR-L3 having the amino acid sequence QQYDESPWT (SEQ ID NO: 16).

Antibodies and antigen-binding fragments thereof containing the foregoing CDR sequences are described, e.g., in U.S. Pat. No. 5,869,619, the disclosure of which is incorporated herein by reference as it pertains to anti-CD5 antibodies and antigen-binding fragments thereof.

Other anti-CD5 antibodies that can be used in conjunction with the compositions and methods described herein include, for instance, anti-CD5 antibodies that are described in U.S. Pat. Nos. 5,821,123; 5,766,886; 5,770,196; 7,153,932; 5,621,083; 6,649,742; 6,146,631; 5,756,699; 5,744,580; 6,376,217; 5,837,491; and 6,146,850, the disclosures of each of which are incorporated herein by reference as they pertain to anti-CD5 antibodies and antigen-binding fragments thereof.

Other anti-CD5 antibodies that can be used in conjunction with the compositions and methods described herein include, for instance, those produced by the hybridoma cell line deposited as ATCC CRL 8000 (anti-CD5 murine antibody OKT1). Such antibodies are described in U.S. Pat. Nos. 4,515,894; 4,657,760; and 4,363,799, the disclosures of each of which are incorporated herein by reference as they pertains to anti-CD5 antibodies and antigen-binding fragments thereof.

Anti-CD5 antibodies that can be used in conjunction with the compositions and methods described herein include those that have one or more, or all, of the following CDRs:
  a CDR-H1 having the amino acid sequence GYSITSGYY (SEQ ID NO: 17);
  a CDR-H2 having the amino acid sequence ISYSGFT (SEQ ID NO: 18);
  a CDR-H3 having the amino acid sequence AGDRTGSWFAY (SEQ ID NO: 19);
  a CDR-L1 having the amino acid sequence QDISNY (SEQ ID NO: 20);
  a CDR-L2 having the amino acid sequence ATS (SEQ ID NO: 21); and
  a CDR-L3 having the amino acid sequence LQYASYPFT (SEQ ID NO: 22).

Antibodies and antigen-binding fragments thereof containing the foregoing CDR sequences are described, e.g., in U.S. Pat. No. 8,679,500, the disclosure of which is incorporated herein by reference as it pertains to anti-CD5 antibodies and antigen-binding fragments thereof.

Anti-CD5 antibodies that can be used in conjunction with the compositions and methods described herein include those that have one or more, or all, of the following CDRs:
  a CDR-H1 having the amino acid sequence GYIFTNYG (SEQ ID NO: 23);
  a CDR-H2 having the amino acid sequence INTYNGEP (SEQ ID NO: 24);
  a CDR-H3 having the amino acid sequence ARGDYYGYEDY (SEQ ID NO: 25);
  a CDR-L1 having the amino acid sequence QGISNY (SEQ ID NO: 26);
  a CDR-L2 having the amino acid sequence YTS (SEQ ID NO: 27); and
  a CDR-L3 having the amino acid sequence QQYSKLPWT (SEQ ID NO: 28).

Antibodies and antigen-binding fragments thereof containing the foregoing CDR sequences are described, e.g., in U.S. Pat. No. 8,679,500.

Anti-CD5 antibodies that can be used in conjunction with the compositions and methods described herein include those that have one or more, or all, of the following CDRs:
  a CDR-H1 having the amino acid sequence FSLSTSGMG (SEQ ID NO: 29);
  a CDR-H2 having the amino acid sequence WWDDD (SEQ ID NO: 30);
  a CDR-H3 having the amino acid sequence RRATGTGFDY (SEQ ID NO: 31);
  a CDR-L1 having the amino acid sequence QDVGTA (SEQ ID NO: 32);
  a CDR-L2 having the amino acid sequence WTSTRHT (SEQ ID NO: 33); and
  a CDR-L3 having the amino acid sequence YNSYNT (SEQ ID NO: 34).

Antibodies and antigen-binding fragments thereof containing the foregoing CDR sequences are described, e.g., in US Patent Application Publication No. 2008/0254027, the disclosure of which is incorporated herein by reference as it pertains to anti-CD5 antibodies and antigen-binding fragments thereof.

Other anti-CD5 antibodies that can be used in conjunction with the compositions and methods described herein include, for instance, anti-CD5 antibodies that are described in PCT Application Publication No. WO1992/014491, such as the anti-CD5 antibodies produced by hybridoma cell line deposited at the Institut Pasteur under No. 1-1025 on Jan. 10, 1991. The disclosure of PCT Application Publication No. WO1992/014491 is incorporated herein by reference as it pertains to anti-CD5 antibodies and antigen-binding fragments thereof.

Other anti-CD5 antibodies that can be used in conjunction with the compositions and methods described herein include, for instance, anti-CD5 antibodies that are described in U.S. Pat. Nos. 6,010,902 and 7,192,736, US Patent Application Publication Nos. 2011/0250203 and 2017/0129128, and PCT Application Publication Nos. WO2016/172606; WO1994/023747; and WO1996/041608; the disclosures of each of which are incorporated herein by reference as they pertain to anti-CD5 antibodies and antigen binding fragments thereof.

In some embodiments, the anti-CD5 antibodies that can be used in conjunction with the compositions and methods described herein include those that contain a combination of CDR-H1, CDR-H2, CDR-H3, CDR-L1, CDR-L2, and CDR-L3 regions set forth in Table 1, below.

TABLE 1

| Ab No. | Name | CDRH1 | SEQ ID NO: | CDRH2 | SEQ ID NO: | CDRH3 | SEQ ID NO: |
|---|---|---|---|---|---|---|---|
| 1 | 1D8 | SGYSFTGYTM | 35 | LINPYNGGTT | 36 | CARDYYGSSPDFDYW | 37 |
| 2 | 3I21 | SGYSFTDYTM | 38 | LINPYNGGTM | 39 | CARDNYGSSPDFDYW | 40 |
| 3 | 4H10 | SGYSFTGYTM | 41 | LINPYNGGTM | 42 | CARDNYGSSPYFDYW | 43 |
| 4 | 8J23 | SGYSFTGYTM | 44 | LINPYNGGTM | 45 | CARDNYGSSPYFDYW | 46 |
| 5 | 5O4 | SGYSFTGYTM | 47 | LINPYNGGTT | 48 | CARDYYGSSPDFDYW | 49 |
| 6 | 4H2 | SGFTFSNYAM | 50 | SISSGGNTF | 51 | CVRYYYGVTYWYFDVW | 52 |
| 7 | 5G2 | SGFTFSSYAM | 53 | SISSGGSTY | 54 | CVRYYYGIRYWYFDVW | 55 |
| 8 | 8G8 | SGYSFTAYNI | 56 | SIDPYYGDTK | 57 | CARRMITMGDWYFDVW | 58 |
| 9 | 6M4 | SGYSFTAYSM | 59 | SIDFACYGDTK | 60 | CARRMITTGDWYFDVW | 61 |
| 10 | 2E3 | SGYTFTNFAI | 62 | LISSNSGDVS | 63 | CARHYGAHNYFDYW | 64 |
| 11 | 4E24 | SGYTFTNFAI | 65 | LISTSSGDVS | 66 | CARHYGANNYFDYW | 67 |
| 12 | 4F10 | SGYTFTNFAI | 68 | LISSNSGDVS | 69 | CARHYGAHNYFDYW | 70 |
| 13 | 7J9 | SGYTFTNFAI | 71 | LISSNSGDVS | 72 | CARHYGAHNYFDYW | 73 |
| 14 | 7P9 | SGFNIKDTYM | 74 | RIDPANGNTK | 75 | CAREENYYGTYYFDYW | 76 |
| 15 | 8E24 | SGYSFTSYWM | 77 | MIHPSDSETR | 78 | CARWGDHDDAMDFW | 79 |
| 16 | 6L18 | SGFSLTNYDV | 80 | VIWSGGNTD | 81 | CARNHGDGYFNWYFDVW | 82 |
| 17 | 7H7 | SGFSLTNYDV | 83 | VIWSGGNTD | 84 | CARNHGDGYYNWYFDVW | 85 |
| 18 | 1E7 | SGFTFSNYGM | 86 | AINSNGDITY | 87 | CARGTAWFTYW | 88 |
| 19 | 8J21 | SGYSFTGYTM | 89 | LINPYNGGTR | 90 | CARDGDDGWDIDVW | 91 |
| 20 | 7I11 | SGYIFANYGM | 92 | WINTYTGEPT | 93 | CARRGTYWHFDVW | 94 |
| 21 | 8M9 | SGYNFTNYGM | 95 | WINTYTGEPT | 96 | CARRGSYWHFDVW | 97 |
| 22 | 1P21 | SGYTFTNYGM | 98 | WINTYTGEPT | 99 | CARRSTLVFDYW | 100 |
| 23 | 2H11 | SGYTFTDYYI | 101 | WIYPGGGNTR | 102 | CARNGYWYFDVW | 103 |
| 24 | 3M22 | SGYTFTDYYI | 104 | WIYPGGGNTR | 105 | CARNGYWYFDVW | 106 |
| 25 | 5M6 | SGNTFTNFYL | 107 | CIYPGNVKTK | 108 | CAKEGDYDGTAYFDYW | 109 |
| 26 | 5H8 | SGYTFTNYGM | 110 | WINTYTGEPT | 111 | CARRDGNFDYW | 112 |
| 27 | 7I19 | SEFTFSNYAM | 113 | TISSGGSYTY | 114 | CVRHGYFDVW | 115 |
| 28 | 1A20 | SGYTFTSYRM | 116 | RIDPYDSGTH | 117 | CAFYDGAYW | 118 |
| 29 | 8E15 | SGFNIKDTYM | 119 | RIDPANGNTK | 120 | CASYDPDYW | 121 |
| 30 | 8C10 | SGYSFTDYTM | 122 | LINPYNGGTR | 123 | CARDTTATYYFDYW | 124 |
| 31 | 3P16 | SGYMFTNHGM | 125 | WINTYTGEPT | 126 | CARRVATYFDVW | 127 |
| 32 | 4F3 | SGYMFTNYGM | 128 | WINTYTGEPT | 129 | CTRRSHITLDYW | 130 |

TABLE 1-continued

| Ab No. | Name | CDRH1 | SEQ ID NO: | CDRH2 | SEQ ID NO: | CDRH3 | SEQ ID NO: |
|---|---|---|---|---|---|---|---|
| 33 | 5M24 | SGYIFTNYGM | 131 | WINTYTGEPT | 132 | CARRRTTAFDYW | 133 |
| 34 | 5O24 | SGFNIKDYYI | 134 | WIDPENGRTE | 135 | CNNGNYVRHYYFDYW | 136 |
| 35 | 7B16 | SGYTFINYGM | 137 | WINTYTGEPT | 138 | CTRRREITFDYW | 139 |
| 36 | 1E8 | SGYTFTDYFI | 140 | EIYPGSSNTY | 141 | CARSGISPFTYW | 142 |
| 37 | 2H16 | SGYIFTGYNI | 143 | AVYPGNGDTS | 144 | CAKYDRFFASW | 145 |

| Ab No. | Name | CDRL1 | SEQ ID NO: | CDRL2 | SEQ ID NO: | CDRL3 | SEQ ID NO: |
|---|---|---|---|---|---|---|---|
| 1 | 1D8 | SQGISNHL | 146 | YFTSS | 147 | CQQYSNLPYTF | 148 |
| 2 | 3I21 | SQGIRNYL | 149 | YFTSS | 150 | CQQYSNLPYTF | 151 |
| 3 | 4H10 | SQGISNHL | 152 | YFTSS | 153 | CQQYSNLPYTF | 154 |
| 4 | 8J23 | SQGINNYL | 155 | YYTSS | 156 | CQQYSKIPYTC | 157 |
| 5 | 5O4 | SQGISNHL | 158 | YFTSS | 159 | CQQYSNLPYTF | 160 |
| 6 | 4H2 | SQSVDHDGDSYM | 161 | YAASN | 162 | CQQNYEDPTF | 163 |
| 7 | 5G2 | SQSVDYDGDSYM | 164 | YAASN | 165 | CQQSNEDPTF | 166 |
| 8 | 8G8 | SQDISNYL | 167 | YYTSR | 168 | CQQGDALPWTF | 169 |
| 9 | 6M4 | SQDISTYL | 170 | FYTSR | 171 | CQQGNSLPFTF | 172 |
| 10 | 2E3 | TSSISSSYL | 173 | YGTSN | 174 | CQQWSSRPPTF | 175 |
| 11 | 4E24 | NSSVSSSYL | 176 | YGTSN | 177 | CQQYSGYPLTF | 178 |
| 12 | 4F10 | TSSISSSYL | 179 | YGTSN | 180 | CQQYSDYPLTF | 181 |
| 13 | 7J9 | TSSISSSYL | 182 | YGTSN | 183 | CQQRSYFPFTF | 184 |
| 14 | 7P9 | SENIYYNL | 185 | YNANS | 186 | CKQVYDVPFTF | 187 |
| 15 | 8E24 | SENIYGYF | 188 | YNAKT | 189 | CQHHYGTPFTF | 190 |
| 16 | 6L18 | SQDINNYI | 191 | HYTST | 192 | CLQYDNLWTF | 193 |
| 17 | 7H7 | SQDINKY1 | 194 | HYTST | 195 | CLQYDNLVVIF | 196 |
| 18 | 1E7 | SENIYSYL | 197 | YNAKT | 198 | CQHHYGYPYTF | 199 |
| 19 | 8J21 | SQGIRNYL | 200 | YHTST | 201 | CQQYSNLPLTF | 202 |
| 20 | 7I11 | SQDVRTDV | 203 | YSASF | 204 | CQQHYTSPWTF | 205 |
| 21 | 8M9 | SQDVITAV | 206 | YSASY | 207 | CQQHYSTPWTF | 208 |
| 22 | 1P21 | SQSIGTSI | 209 | KSASE | 210 | CQQSNRWPLTF | 211 |
| 23 | 2H11 | SSQSLLNQKNYL | 212 | YWAST | 213 | CQNDYDYPYTF | 214 |
| 24 | 3M22 | SSSVSSSYL | 215 | YSTSN | 216 | CHQYHRSPLTF | 217 |
| 25 | 5M6 | SENIYYNL | 218 | YNANS | 219 | CQQTFDVPWTF | 220 |
| 26 | 5H8 | SQTIGTSI | 221 | KNASE | 222 | CQQSNSWPLTY | 223 |
| 27 | 7I19 | SQSLLYSSDQKNYL | 224 | YWAST | 225 | CQQYYNYPLTF | 226 |
| 28 | 1A20 | NSSVSYM | 227 | YDTSK | 228 | CQQWSSNPFTF | 229 |
| 29 | 8E15 | SENIYYNL | 230 | YNANS | 231 | CKQAYDVPWTF | 232 |
| 30 | 8C10 | SSSLSYM | 233 | YDTSN | 234 | CQQWSSFPPTF | 235 |
| 31 | 3P16 | SQRIGTSM | 236 | KSASE | 237 | CQQSNSWPLTF | 238 |
| 32 | 4F3 | SQSIGTSI | 239 | KSASE | 240 | CQQSNSWPLTF | 241 |
| 33 | 5M24 | SQNIGTSI | 242 | KDASE | 243 | CQQSDSWPLTF | 244 |
| 34 | 5O24 | ISSVSYM | 245 | YATSN | 246 | CQQWSSNPRTF | 247 |

TABLE 1-continued

| | | | | | | | |
|---|---|---|---|---|---|---|---|
| 35 | 7B16 | SQTIATSI | 248 | KNASE | 249 | CQQSNSWPLTF | 250 |
| 36 | 1E8 | SQSLVHSNGNTYL | 251 | YKVSN | 252 | CWQNTHFPQTF | 253 |
| 37 | 2H16 | NESVEYSGTSLM | 254 | SAASN | 255 | CQQSRQVPLTF | 256 |

Antibodies and antigen-binding fragments thereof containing the foregoing CDR sequences of Table 1 are described, e.g., in US Patent Application Publication No. 2011/0250203, the disclosure of which is incorporated herein by reference as it pertains to anti-CD5 antibodies and antigen binding fragments thereof.

Antibodies and fragments thereof for use in conjunction with the compositions and methods described herein include variants of those antibodies described above, such as antibody fragments that contain or lack an Fc domain, as well as humanized variants of non-human antibodies described herein and antibody-like protein scaffolds (e.g., $^{10}$Fn3 domains) containing one or more, or all, of the CDRs or equivalent regions thereof of an antibody, or an antibody fragment, described herein. Exemplary antigen-binding fragments of the foregoing antibodies include a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv, among others.

The foregoing anti-CD5 antibodies, or antigen-binding fragments thereof, can be used in various aspects of the invention set forth herein, including, for example, in methods for depletion of CD5+ cells in a human subject. The foregoing anti-CD5 antibodies, or antigen-binding fragments thereof, can also be conjugated to an agent, e.g., a cytotoxin, for example, an amatoxin, as described herein. Additional anti-CD5 antibodies that may be used in aspects of the instant invention are described in U.S. Pat. No. 8,679,500, U.S. Patent Application Publication No. US2011/0250203, and U.S. Patent Application Publication No. US2008/0254027, the entire contents of each of which are incorporated herein by reference. Additional anti-CD5 antibodies which may be used in aspects of the instant invention include, for example, monoclonal antibody T101 described by Dillman et al., J. Clin. Oncol. (1984), 2(8):881-891, and monoclonal antibody Leu-1 described by Miller et al., Blood (1983), 62(5):988-95.

In one embodiment, the anti-CD5 antibody or binding fragment thereof, comprises a modified Fc region, wherein said modified Fc region comprises at least one amino acid modification relative to a wild-type Fc region, such that said molecule has an altered affinity for or binding to an FcgammaR (FcγR). Certain amino acid positions within the Fc region are known through crystallography studies to make a direct contact with FcγR. Specifically amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). The antibodies described herein may comprise variant Fc regions comprising modification of at least one residue that makes a direct contact with an FcγR based on structural and crystallographic analysis. In one embodiment, the Fc region of the anti-CD5 antibody (or fragment thereof) comprises an amino acid substitution at amino acid 265 according to the EU index as in Kabat et al., Sequences of Proteins of Immunological Interest, 5th Ed. Public Health Service, NH1, MD (1991), expressly incorporated herein by references. The "EU index as in Kabat" refers to the numbering of the human IgG1 EU antibody. In one embodiment, the Fc region comprises a D265A mutation. In one embodiment, the Fc region comprises a D265C mutation. In some embodiments, the Fc region of the antibody (or fragment thereof) comprises an amino acid substitution at amino acid 234 according to the EU index as in Kabat. In one embodiment, the Fc region comprises a L234A mutation. In some embodiments, the Fc region of the anti-CD5 antibody (or fragment thereof) comprises an amino acid substitution at amino acid 235 according to the EU index as in Kabat. In one embodiment, the Fc region comprises a L235A mutation. In yet another embodiment, the Fc region comprises a L234A and L235A mutation. In a further embodiment, the Fc region comprises a D265C, L234A, and L235A mutation. In yet a further embodiment, the Fc region comprises a D265C, L234A, L235A, and H435A mutation. In a further embodiment, the Fc region comprises a D265C and H435A mutation.

The antibodies of the invention may be further engineered to further modulate antibody half-life by introducing additional Fc mutations, such as those described for example in (Dall'Acqua et al. (2006) J Biol Chem 281: 23514-24), (Zalevsky et al. (2010) Nat Biotechnol 28: 157-9), (Hinton et al. (2004) J Biol Chem 279: 6213-6), (Hinton et al. (2006) J Immunol 176: 346-56), (Shields et al. (2001) J Biol Chem 276: 6591-604), (Petkova et al. (2006) Int Immunol 18: 1759-69), (Datta-Mannan et al. (2007) Drug Metab Dispos 35: 86-94), (Vaccaro et al. (2005) Nat Biotechnol 23: 1283-8), (Yeung et al. (2010) Cancer Res 70: 3269-77) and (Kim et al. (1999) Eur J Immunol 29: 2819-25), and include positions 250, 252, 253, 254, 256, 257, 307, 376, 380, 428, 434 and 435. Exemplary mutations that may be made singularly or in combination are T250Q, M252Y, I253A, S254T, T256E, P257I, T307A, D376V, E380A, M428L, H433K, N434S, N434A, N434H, N434F, H435A and H435R mutations.

In some embodiments, the anti-CD5 antibody or antigen-binding fragment thereof is conjugated to a cytotoxin (e.g., amatoxin) by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265. In one embodiment, the Fc region of the anti-CD5 antibody (or fragment thereof) comprises an amino acid substitution at amino acid 265 according to the EU index as in Kabat. In one embodiment, the Fc region comprises a D265C mutation. In one embodiment, the Fc region comprises a D265C and a H435A mutation.

Thus, in one embodiment, the Fc region comprises a mutation resulting in a decrease in half life. An antibody having a short half life may be advantageous in certain instances where the antibody is expected to function as a short-lived therapeutic, e.g., the conditioning step described herein where the antibody is administered followed by HSCs. Ideally, the antibody would be substantially cleared prior to delivery of the HSCs, which may also generally express CD5 but are not the target of the anti-CD5 antibody, unlike the endogenous stem cells. In one embodiment, the Fc region comprises a mutation at position 435 (EU index according to Kabat). In one embodiment, the mutation is an H435A mutation.

The foregoing anti-CD5 antibodies, or antigen-binding fragments thereof, can be used in various aspects of the invention set forth herein, including, for example, in methods for depletion of CD5+ cells in a human subject. The foregoing anti-CD5 antibodies, or antigen-binding fragments thereof, can also be conjugated to an agent, e.g., a cytotoxin, for example, an amatoxin, as described herein.

Methods of Identifying Anti-CD5 Antibodies

Methods for high throughput screening of libraries of antibodies, or antibody fragments, for molecules that bind to CD5 can be used to identify and affinity mature agents useful for conditioning a patient (e.g., a human patient) in need of hematopoietic stem cell therapy and/or for directly treating a cancer or autoimmune disease as described herein. Such methods include in vitro display techniques known in the art, such as phage display, bacterial display, yeast display, mammalian cell display, ribosome display, mRNA display, and cDNA display, among others. The use of phage display to isolate antibodies, or antigen-binding fragments, that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty. Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348:552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). These techniques, among others, can be used to identify and improve the affinity of antibodies, or antibody fragments, that bind CD5 that can in turn be used to deplete CD5+ T cells, B cells, and/or NK cells in a patient (e.g., a human patient) in need of hematopoietic stem cell transplant therapy and/or suffering from cancer or an autoimmune disease described herein.

Additional techniques can be used to identify antibodies, and antigen-binding fragments thereof, that bind CD5 on the surface of a cell (e.g., a T cell, B cell, or NK cell) and that are internalized by the cell, for instance, by receptor-mediated endocytosis. For example, the in vitro display techniques described above can be adapted to screen for antibodies, and antigen-binding fragments thereof, that bind CD5 on the surface of a T cell, B cell, or NK cell and that are subsequently internalized. Phage display represents one such technique that can be used in conjunction with this screening paradigm. To identify anti-CD5 antibodies, and fragments thereof, that bind CD5 and are subsequently internalized by T cells, B cells, and/or NK cells, one of skill in the art can use the phage display techniques described in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or antibodies that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD5 antigen, for instance, by first incubating the phage library with blocking agents (such as, for instance, milk protein, bovine serum albumin, and/or IgG so as to remove phage encoding antibodies, or fragments thereof, that exhibit non-specific protein binding and phage that encode antibodies or fragments thereof that bind Fc domains, and then incubating the phage library with a population of T cells, B cells, or NK cells that are CD5+. The phage library can be incubated with the T cells, B cells, or NK cells for a time sufficient to allow CD5-specific antibodies, or antigen-binding fragments thereof, to bind cell-surface CD5 and to subsequently be internalized by the T cells, B cells, or NK cells (e.g., from 30 minutes to 6 hours at 4° C., such as 1 hour at 4° C.). Phage containing antibodies, or fragments thereof, that do not exhibit sufficient affinity for CD5 so as to permit binding to, and internalization by, T cells, B cells, or NK cells can subsequently be removed by washing the cells, for instance, with cold (4° C.) 0.1 M glycine buffer at pH 2.8. Phage bound to antibodies, or fragments thereof, that have been internalized by the T cells, B cells, and/or NK cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or fragments thereof, inserted within the phage genome. The encoded antibodies, or fragments thereof, can subsequently be prepared de novo by chemical synthesis (for instance, of antibody fragments, such as scFv fragments) or by recombinant expression (for instance, of full-length antibodies).

An exemplary method for in vitro evolution of anti-CD5 antibodies for use with the compositions and methods described herein is phage display. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains). The template antibody-encoding sequence into which these mutations are introduced may be, for example, a naive human germline sequence. These mutations can be performed using standard mutagenesis techniques known in the art. Each mutant sequence thus encodes an antibody corresponding to the template save for one or more amino acid variations. Retroviral and phage display vectors can be engineered using standard vector construction techniques known in the art. P3 phage display vectors along with compatible protein expression vectors can be used to generate phage display vectors for antibody diversification.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its overall molecular structure.

In a typical screen, a phage library may be contacted with and allowed to bind CD5 or an epitope thereof. To facilitate separation of binders and non-binders, it is convenient to immobilize the target on a solid support. Phage bearing a CD5-binding moiety can form a complex with the target on the solid support, whereas non-binding phage remain in solution and can be washed away with excess buffer. Bound phage can then liberated from the target by changing the buffer to an extreme pH (pH 2 or pH 10), changing the ionic strength of the buffer, adding denaturants, or other known means.

The recovered phage can then be amplified through infection of bacterial cells, and the screening process can be repeated with the new pool that is now depleted in non-binding antibodies and enriched for antibodies that bind CD5. The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof. An increase in the number of phage recovered at each round of selection is an indication that convergence of the library has occurred in a screen.

Another method for identifying anti-CD5 antibodies includes using humanizing non-human antibodies that bind CD5, for instance, according to the following procedure. Non-human antibodies that bind CD5 can be humanized, for instance, according to the following procedure. Consensus human antibody heavy chain and light chain sequences are known in the art (see e.g., the "VBASE" human germline sequence database: Kabat et al. Sequences of Proteins of Immunological Interest, Fifth Edition, U.S. Department of Health and Human Services. NIH Publication No. 91-3242, 1991; Tomlinson et al., J. Mol. Biol. 227:776-798, 1992; and Cox et al., Eur. J. Immunol. 24:827-836, 1994, the disclosures of each of which are incorporated herein by reference as they pertain to consensus human antibody heavy chain and light chain sequences. Using established procedures, one of skill in the art can identify the variable domain framework residues and CDRs of a consensus antibody sequence (e.g., by sequence alignment). One can substitute one or more CDRs of the heavy chain and/or light chain variable domains of consensus human antibody with one or more corresponding CDRs of a non-human antibody that binds CD5 in order to produce a humanized antibody. This CDR exchange can be performed using gene editing techniques described herein or known in the art.

One example of a variable domain of a consensus human antibody contains the heavy chain variable domain EVQLVESGGGLVQPGGSLRLSCAASGFTFSDYAMSWVRQAPGKGLEWVAVISENGSDTYYADSVKGRFTISRDDSKNTLYLQMNSLRAEDTAVYYCARDRGGAVSYFDVWGQGTLVTVSS (SEQ ID NO: 259) and the light chain variable domain DIQMTQSPSSLSASVGDRVTITCRASQDVSSYLAWYQQKPGKAPKLLIYAASSLESGVPSRFSGSGSGTDFTLTISSLQPEDFATYYCQQYNSLPYTFGQGTKVEIKRT (SEQ ID NO: 260), identified in U.S. Pat. No. 6,054,297, the disclosure of which is incorporated herein by reference as it pertains to human antibody consensus sequences. The CDRs in the above sequences are shown in bold.

To produce humanized antibodies, one can recombinantly express a polynucleotide encoding the above consensus sequence in which one or more variable region CDRs have been replaced with one or more variable region CDR sequences of a non-human antibody that binds CD5. As the affinity of the antibody for CD5 is determined primarily by the CDR sequences, the resulting humanized antibody is expected to exhibit an affinity for CD5 that is about the same as that of the non-human antibody from which the humanized antibody was derived. Methods of determining the affinity of an antibody for a target antigen include, for instance, ELISA-based techniques described herein and known in the art, as well as surface plasmon resonance, fluorescence anisotropy, and isothermal titration calorimetry, among others.

The internalizing capacity of the prepared antibodies, or fragments thereof, can be assessed, for instance, using radionuclide internalization assays known in the art. For example, anti-CD5 antibodies, or fragments thereof, identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{189}$Yb, $^{186}$Re, $^{64}$Cu, $^{67}$Cu, $^{177}$Lu, $^{77}$As, $^{72}$As, $^{88}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, or fragments thereof, using beads, such as polystyrene beads, containing electrophilic halogen reagents (e.g., Iodination Beads, Thermo Fisher Scientific. Inc., Cambridge, MA). Radiolabeled antibodies, or fragments thereof, can be incubated with T cells, B cells, and/or NK cells for a time sufficient to permit internalization (e.g., from 30 minutes to 6 hours at 4° C., such as 1 hour at 4° C.). The cells can then be washed to remove non-internalized antibodies, or fragments thereof, (e.g., using cold (4° C.) 0.1 M glycine buffer at pH 2.8). Internalized antibodies, or fragments thereof, can be identified by detecting the emitted radiation (e.g., γ-radiation) of the resulting T cells, B cells, and/or NK cells in comparison with the emitted radiation (e.g., γ-radiation) of the recovered wash buffer.

For recombinant production of an anti-CD5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Chariton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003). In one embodiment, the host cell is eukaryotic, e.g. a Chinese Hamster Ovary (CHO) cell or lymphoid cell (e.g., Y0, NS0, Sp20 cell).

Antibody-Drug Conjugates (ADCs)

Cytotoxins

Antibodies, and antigen-binding fragments thereof, described herein (e.g., antibodies, antigen-binding fragments, that recognize and bind CD5) can be conjugated to a cytotoxin, such as *Pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof, or another cytotoxic compound described herein or known in the art in order to (i) directly treat a cancer or autoimmune disease described herein or (ii) deplete endogenous immune cells so as to prevent or reduce the likelihood of rejection of hematopoietic stem cells upon transplantation into a patient (e.g., a human patient) in need of hematopoietic stem cell transplant therapy. In some embodiments, the cytotoxic molecule is conjugated to an internalizing antibody, or antigen-binding fragment thereof, such that following the cellular uptake of the antibody, or antigen-binding fragment, the cytotoxin may access its intracellular target and kill endogenous T cells, B cells, and/or NK cells. Suitable cytotoxins suitable for use with the compositions and methods described herein include DNA-intercalating agents, (e.g., anthracyclines), agents capable of disrupting the mitotic spindle apparatus (e.g., *vinca* alkaloids, maytansine, maytansinoids, and derivatives thereof), RNA polymerase inhibitors (e.g., an amatoxin, such as α-amanitin, and derivatives thereof), agents capable of disrupting protein biosynthesis (e.g., agents that exhibit rRNA N-glycosidase activity, such as saporin and ricin A-chain), among others known in the art.

In some embodiments, the cytotoxin of the antibody-drug conjugate is an RNA polymerase inhibitor. In some embodiments, the RNA polymerase inhibitor is an amatoxin or derivative thereof.

In some embodiments, the cytotoxin is an amatoxin or derivative thereof, such as α-amanitin, β-amanitin, γ-amanitin, ε-amanitin, amanin, amaninamide, amanullin, amanullinic acid, and proamanullin. Structures of the various naturally occurring amatoxins are represented by formula III, and are disclosed in, e.g., Zanotti et al., Int. J. Peptide Protein Res. 30, 1987, 450-459.

In one embodiment, the cytotoxin is an amanitin. For instance, the antibodies, or antigen-binding fragments, described herein may be bound to an amatoxin so as to form a conjugate represented by the formula Ab-Z-L-Am, wherein Ab is the antibody, or antigen-binding fragment thereof, L is a linker, Z is a chemical moiety and Am is an amatoxin. Many positions on amatoxins or derivatives thereof can serve as the position to covalently bond the linking moiety L, and, hence the antibodies or antigen-binding fragments thereof. For instance, the antibodies, and antigen-binding fragments, described herein may be bound to an amatoxin so as to form a conjugate represented by the formula Ab-Z-L-Am, wherein Ab is the antibody, or antigen-binding fragment thereof, Z is a chemical moiety, L is a linker, and Am is an amatoxin. In some embodiments, Am-L-Z is represented by formula (I)

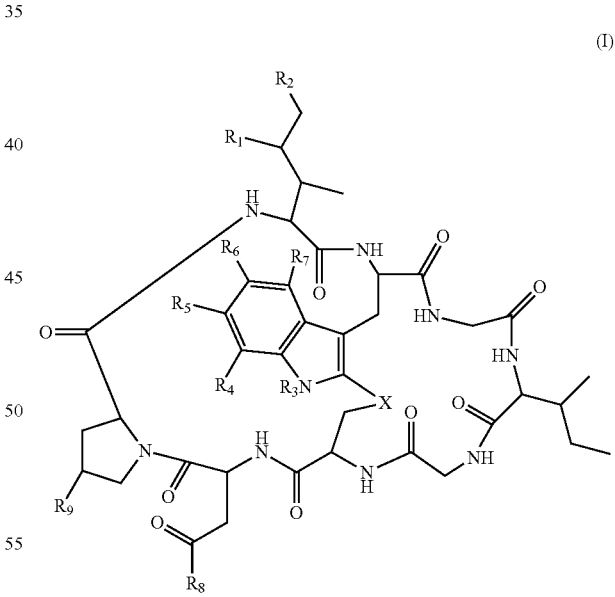

(I)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocyclolalkyl group:
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;

R₇ is H, OH, OR_C, OR_D, R_C, or R_D;
R₈ is OH, NH₂, OR_C, OR_D, NHR_C, or NR_CR_D;
R₉ is H, OH, OR_C, or OR_D;
X is —S—, —S(O)—, or —SO₂—:
R_C is -L-Z;
R_D is optionally substituted alkyl (e.g., C₁-C₆ alkyl), optionally substituted heteroalkyl (e.g., C₁-C₆ heteroalkyl), optionally substituted alkenyl (e.g., C₂-C₆ alkenyl), optionally substituted heteroalkenyl (e.g., C₂-C₆ heteroalkenyl), optionally substituted alkynyl (e.g., C₂-C₆ alkynyl), optionally substituted heteroalkynyl (e.g., C₂-C₆ heteroalkynyl), optionally substituted cycloalkyl, optionally substituted heterocycloalkyl, optionally substituted aryl, or optionally substituted heteroaryl;
L is a linker, such as optionally substituted alkylene (e.g., C₁-C₆ alkylene), optionally substituted heteroalkylene (C₁-C₆ heteroalkylene), optionally substituted alkenylene (e.g., C₂-C₆ alkenylene), optionally substituted heteroalkenylene (e.g., C₂-C₆ heteroakenylene), optionally substituted alkynylene (e.g., C₂-C₆ alkynylene), optionally substituted heteroalkynylene (e.g., C₂-C₆ heteroalkynylene), optionally substituted cycloalkylene, optionally substituted heterocycloalkylene, optionally substituted arylene, optionally substituted heteroarylene, a dipeptide, —C(=O)—, a peptide, or a combination thereof; and
Z is a chemical moiety formed from a coupling reaction between a reactive substituent present on L and a reactive substituent present within an antibody, or antigen-binding fragment thereof, that binds CD5.

In some embodiments, Am contains exactly one R_C substituent.

In some embodiments, the linker comprises a —(C_H)_{2n}— unit, where n is an integer from 2-6. In some embodiments, the linker includes —((CH₂)_n where n is 6. In some embodiments, L-Z is

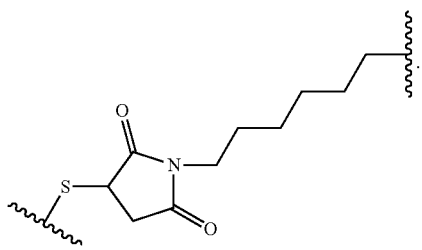

where S is a sulfur atom which represents the reactive substituent present within an antibody, or antigen-binding fragment thereof, that binds CD117 (e.g., from the —SH group of a cysteine residue).

In some embodiments, L-Z is

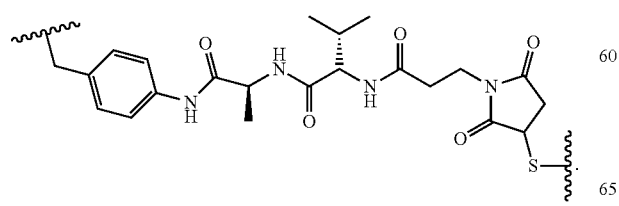

In some embodiments, Am-L-Z-Ab is

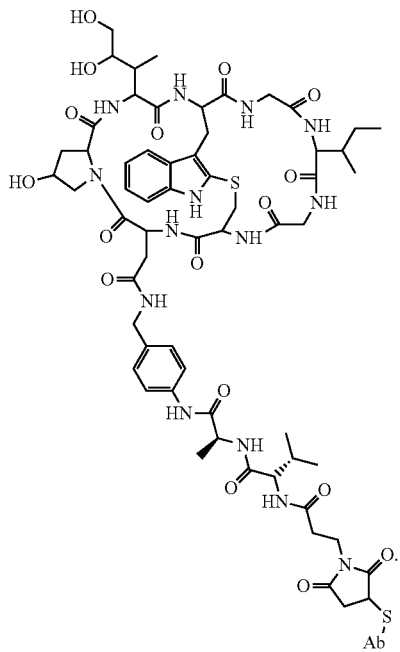

In some embodiments, Am-L-Z-Ab is

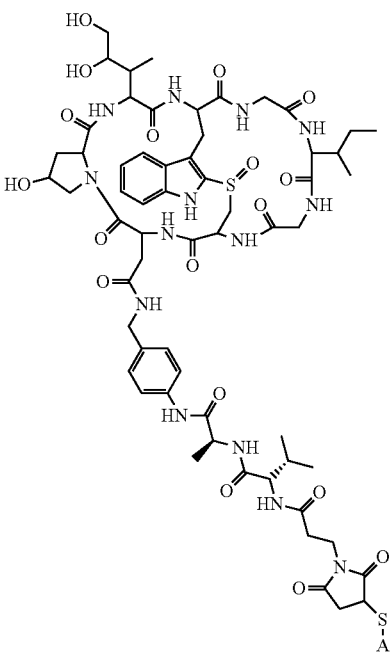

In some embodiments, Am-L-Z is represented by formula (IA)

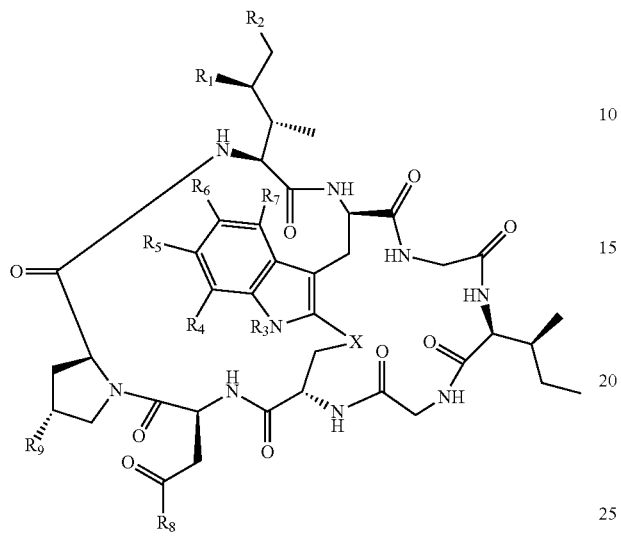
(IA)

wherein $R_1$ is H, OH, $OR_A$, or $OR_C$;
$R_2$ is H, OH, $OR_B$, or $OR_C$;
$R_A$ and $R_B$, When present, together With the oxygen atoms to which they are bound, combine to form an optionally substituted 5-membered heterocyclolalkyl group:
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—:
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_8$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —C(=O)—, a peptide, or a combination thereof:
Z is a chemical moiety formed from a coupling reaction between a reactive substituent present on L and a reactive substituent present within an antibody, or antigen-binding fragment thereof, that binds CD5; and
wherein Am contains exactly one $R_C$ substituent.

In some embodiments, the linker includes —$((CH_2)_n$ where n is 6. In some embodiments, L-Z is

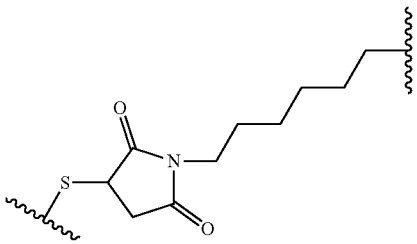

In some embodiments, L-Z is

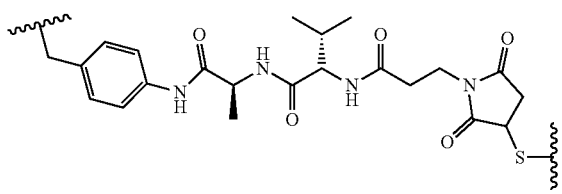

In some embodiments, Am-L-Z-Ab is

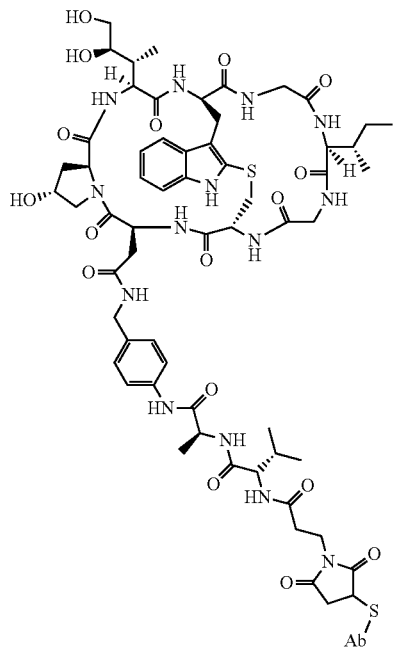

In some embodiments, Am-L-Z-Ab is

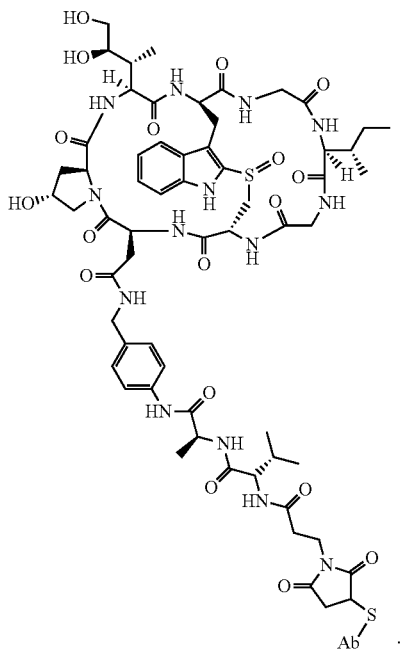

In some embodiments, Am-L-Z is represented by formula (IB)

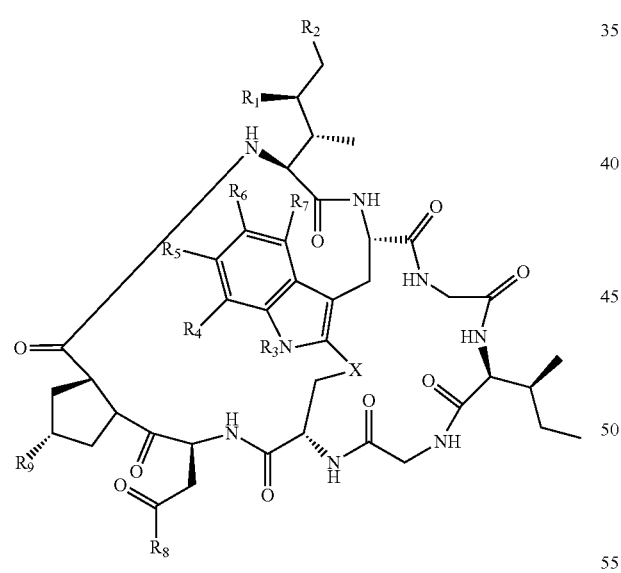

wherein $R_1$ is H, OH, $OR_A$, or $OR_C$;
$R_2$ is H, OH, $OR_B$, or $OR_C$;
$R_A$ and $R_B$, When present, together with the oxygen atoms to which they are bound, combine to form an optionally substituted 5-membered heterocyclolalkyl group:
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;

$R_9$ is H, OH, $OR_C$, or $OR_D$;
X is —S—, —S(O)—, or —SO$_2$—:
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, optionally substituted heteroarylene, a dipeptide, —C(=O)—, a peptide, or a combination thereof;

Z is a chemical moiety formed from a coupling reaction between a reactive substituent present on L and a reactive substituent present within an antibody, or antigen-binding fragment thereof, that binds CD5; and wherein Am contains exactly one $R_C$ substituent.

In some embodiments, the linker L and the chemical moiety Z, taken together as L-Z, is

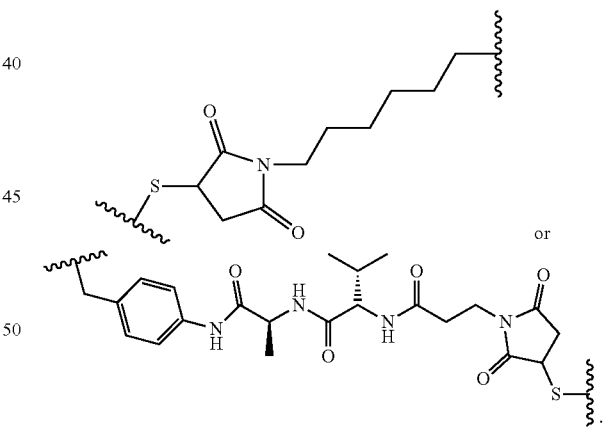

In some embodiments, L-Z is

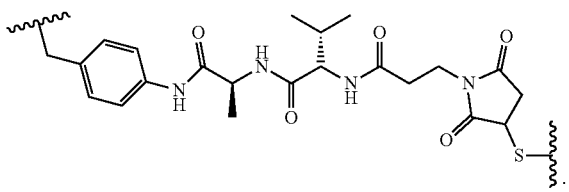

In some embodiments, Am-L-Z-Ab is

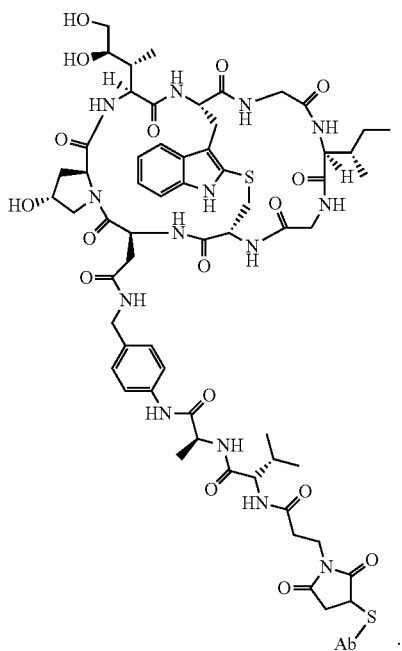

In some embodiments, Am-L-Z-Ab is

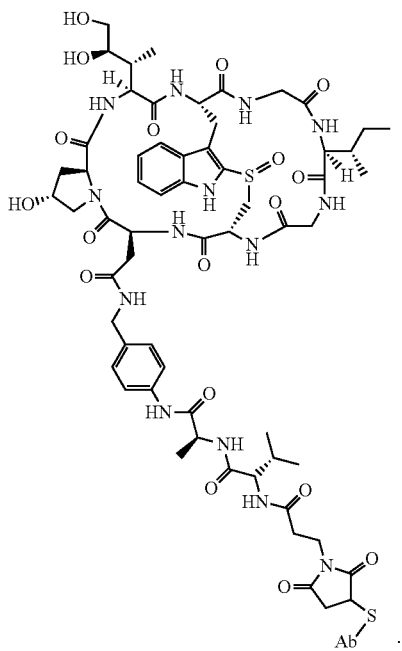

In some embodiments, $R_A$ and $R_B$, together with the oxygen atoms to which they are bound, combine to form a 5-membered heterocycloalkyl group of formula:

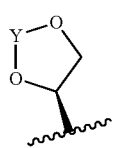

wherein Y is —C(=O)—, —C(=S)—, —C(=NR$_E$)—, or —C(R$_E$R$_{E'}$)—; and $R_E$ and $R_{E'}$ are each independently optionally substituted $C_1$-$C_6$ alkylene-R$_C$, optionally substituted $C_1$-$C_6$ heteroalkylene-R$_C$, optionally substituted $C_2$-$C_6$ alkenylene-R$_C$, optionally substituted $C_2$-$C_6$ heteroalkenylene-R$_C$, optionally substituted $C_2$-$C_6$ alkynylene-R$_C$, optionally substituted $C_2$-$C_6$ heteroalkynylene-R$_C$, optionally substituted cycloalkylene-R$_C$, optionally substituted heterocycloalkylene-R$_C$, optionally substituted arylene-R$_C$, or optionally substituted heteroarylene-R$_C$.

In some embodiments, Am-L-Z is represented by formula (IA) or formula (IB), wherein $R_1$ is H, OH, OR$_A$, or OR$_C$;

$R_2$ is H, OH, OR$_B$, or OR$_C$;

$R_A$ and $R_B$, together with the oxygen atoms to which they are bound, combine to form:

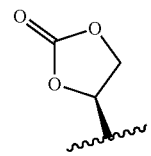 [SMILES: *[C@@H]1COC(=O)O1]

$R_3$ is H or R$_C$;

$R_4$ is H, OH, OR$_C$, OR$_D$, R$_C$, or R$_D$;

$R_5$ is H, OH, OR$_C$, OR$_D$, R$_C$, or R$_D$;

$R_6$ is H, OH, OR$_C$, OR$_D$, R$_C$, or R$_D$;

$R_7$ is H, OH, OR$_C$, OR$_D$, R$_C$, or R$_D$;

$R_8$ is OH, NH$_2$, OR$_C$, or NHR$_C$;

$R_9$ is H or OH; and wherein $R_C$ and $R_D$ are each as defined above.

In some embodiments, Am-L-Z is represented by formula (IA) or formula (IB), wherein $R_1$ is H, OH, OR$_A$, or OR$_C$;

$R_2$ is H, OH, O$_B$, or OR$_C$;

$R_A$ and $R_B$, together with the oxygen atoms to which they are bound, combine to form:

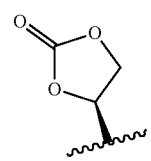 [SMILES: *[C@@H]1COC(=O)O1]

$R_3$ is H or R$_C$;

$R_4$ and $R_5$ are each independently H, OH, OR$_C$, R$_C$, or OR$_D$;

$R_6$ and $R_7$ are each H;

$R_8$ is OH, NH$_2$, OR$_C$, or NHR$_C$;

$R_9$ is H or OH; and wherein X and R$_C$ are as defined above.

In some embodiments, Am-L-Z is represented by formula (IA) or formula (IB), wherein $R_1$ is H, OH, or OR$_A$;

$R_2$ is H, OH, or OR$_B$;

$R_A$ and $R_B$, together with the oxygen atoms to which they are bound, combine to form:

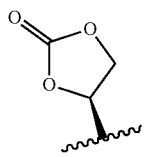 [SMILES: *[C@@H]1COC(=O)O1]

$R_3$, $R_4$, $R_6$, and $R_7$ are each H;

$R_5$ is $OR_C$;

$R_8$ is OH or $NH_2$;

$R_9$ is H or OH; and wherein X and $R_C$ areas defined above. Such amatoxin conjugates are described, for example, in US Patent Application Publication No. 2016/0002298, the disclosure of which is incorporated herein by reference in its entirety.

In some embodiments, Am-L-Z is represented by formula (IA) or formula (IB), wherein $R_1$ and $R_2$ are each independently H or OH;

$R_3$ is $R_C$;

$R_4$, $R_6$, and $R_7$ are each H;

$R_5$ is H, OH, or $OC_1$-$C_6$ alkyl;

$R_8$ is OH or $NH_2$;

$R_9$ is H or OH; and wherein $R_C$ is as defined above. Such amatoxin conjugates are described, for example, in US Patent Application Publication No. 2014/0294865, the disclosure of which is incorporated herein by reference in its entirety.

In some embodiments, Am-L-Z is represented by formula (IA) or formula (IB), wherein $R_1$ and $R_2$ are each independently H or OH;

$R_3$, $R_6$, and $R_7$ are each H;

$R_4$ and $R_5$ are each independently H, OH, $OR_C$, or $R_C$;

$R_8$ is OH or $NH_2$;

$R_9$ is H or OH; and wherein $R_C$ is as defined above. Such amatoxin conjugates are described, for example, in US Patent Application Publication No. 2015/0218220, the disclosure of which is incorporated herein by reference in its entirety.

In some embodiments, Am-L-Z is represented by formula (IA) or formula (IB), wherein $R_1$ and $R_2$ are each independently H or OH;

$R_3$, $R_6$, and $R_7$ are each H;

$R_4$ and $R_5$ are each independently H or OH;

$R_8$ is OH, $NH_2$, $OR_C$, or $NHR_C$;

$R_9$ is H or OH; and wherein X and $R_C$ are as defined above. Such amatoxin conjugates are described, for example, in U.S. Pat. Nos. 9,233,173 and 9,399,681, as well as in US 2016/0089450, the disclosures of each of which are incorporated herein by reference in their entirety.

Additional amatoxins that may be used for conjugation to an antibody, or antigen-binding fragment thereof, in accordance with the compositions and methods described herein are described, for example, in WO 2016/142049; WO 2016/071856; and WO 2017/046658, the disclosures of each of which are incorporated herein by reference in their entirety.

In some embodiments, Am-L-Z is represented by formula (II), formula (IIA), or formula (IIB)

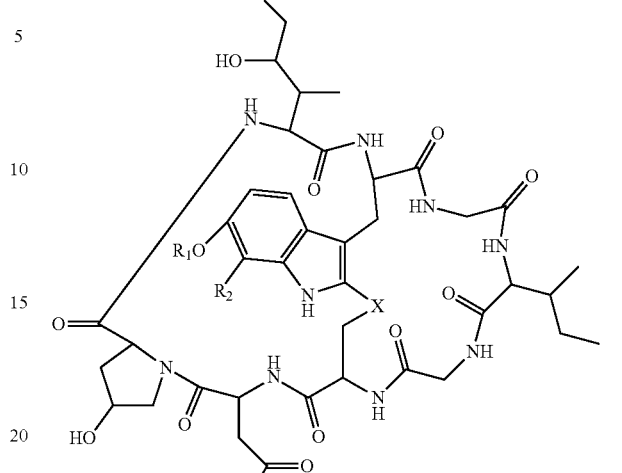

(II)

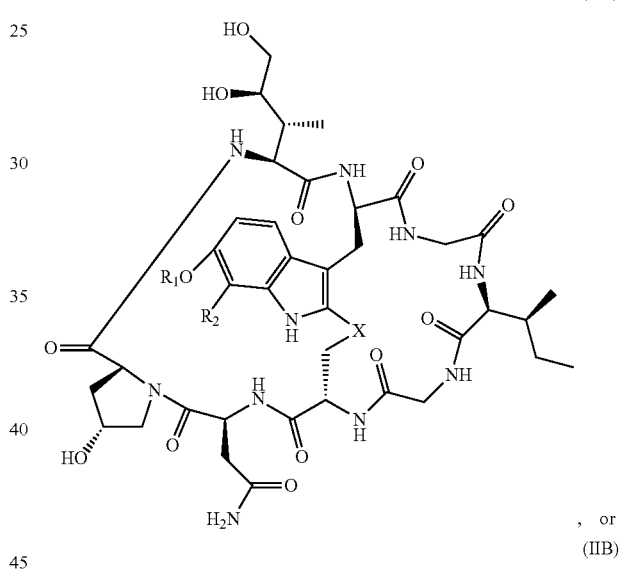

(IIA)

, or

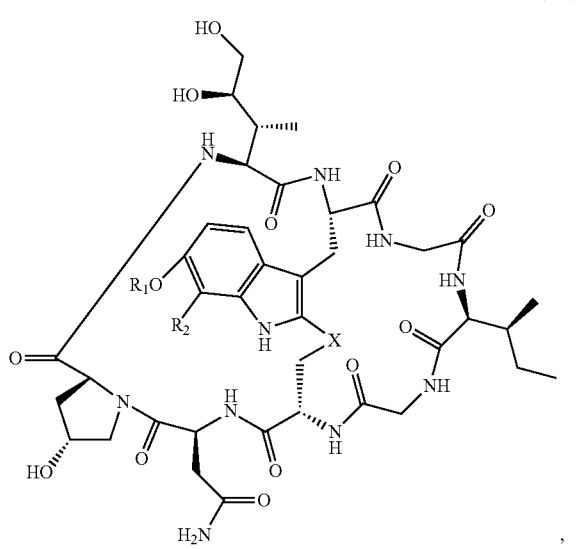

(IIB)

, wherein X is S, SO, or SO$_2$; R$_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and R$_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; wherein when R$_1$ is H, R$_2$ is the linker, and when R$_2$ is H, R$_1$ is the linker.

In some embodiments, the linker includes a —(CH$_2$)$_n$— unit, where n is an integer from 2-6. In some embodiments, R$_1$ is the linker and R$_2$ is H, and the linker and chemical moiety, together as L-Z, is

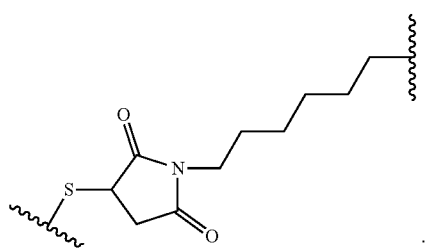 [SMILES: *CCCCCCN1C(=O)CC(S*)C1=O]

In some embodiments, Am-L-Z-Ab is one of:

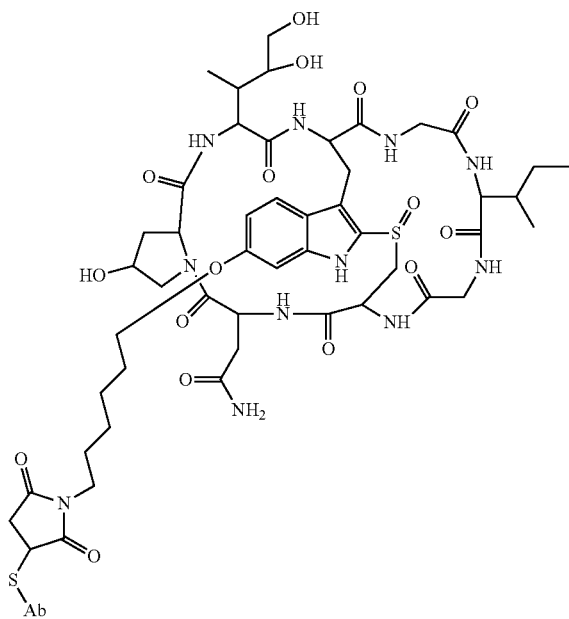

-continued

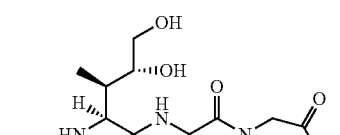

In some embodiments, the cytotoxin is an α-amanitin. In some embodiments, the α-amanitin is a compound of formula III. In some embodiments, the α-amanitin of formula III is attached to an antibody, or antigen-binding fragment thereof, that binds CD5 via a linker L. The linker L may be attached to the α-amanitin of formula III at any one of several possible positions (e.g., any of R$^1$-R$^9$) to provide an α-amanitin-linker conjugate of formula I, IA, IB, II, IIA, or IIB. In some embodiments, the linker is attached at position R$^1$. In some embodiments, the linker is attached at position R$^2$. In some embodiments, the linker is attached at position R$^3$. In some embodiments, the linker is attached at position R$^4$. In some embodiments, the linker is attached at position R$^5$. In some embodiments, the linker is attached at position R$^9$. In some embodiments, the linker is attached at position R$^7$. In some embodiments, the linker is attached at position R$^8$. In some embodiments, the linker is attached at position R$^9$. In some embodiments, the linker includes a hydrazine, a disulfide, a thioether or a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6

In some embodiments, the linker includes a —(CH$_2$)$_n$— unit, where n is an integer from 2-6. In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker L and the chemical moiety Z, taken together as L-Z, is

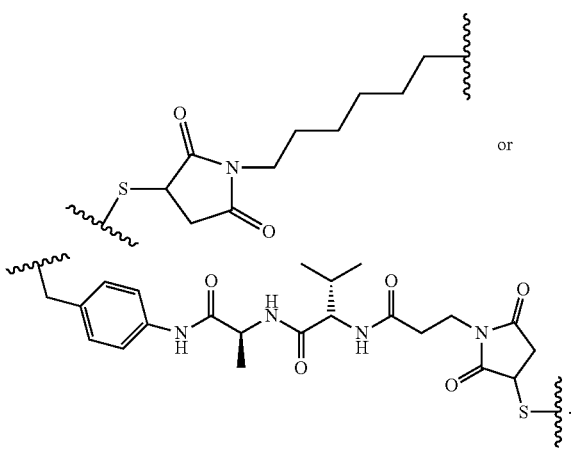

Antibodies, and antigen-binding fragments, for use with the compositions and methods described herein can be conjugated to an amatoxin, such as α-amanitin or a variant thereof, using conjugation techniques known in the art or described herein. For instance, antibodies, and antigen-binding fragments thereof, that recognize and bind CD5 can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation. Synthetic methods of making amatoxins are described in, for example, U.S. Pat. No. 9,676,702, which is incorporated by reference herein with respect to the synthetic methods disclosed therein.

Antibodies, or antigen-binding fragments, for use with the compositions and methods described herein can be conjugated to an amatoxin, such as α-amanitin or a variant thereof, using conjugation techniques known in the art or described herein. For instance, antibodies, or antigen-binding fragments thereof, that recognize and bind CD5 can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Exemplary antibody-drug conjugates useful in conjunction with the methods described herein may be formed by the reaction of an antibody, or an antigen-binding fragment thereof, with an amatoxin that is conjugated to a linker containing a substituent suitable for reaction with a reactive residue on the antibody, or the antigen-binding fragment thereof. Amatoxins that are conjugated to a linker containing a substituent suitable for reaction with a reactive residue on the antibody, or antigen-binding fragment thereof, described herein include, without limitation, 7'C-(4-(6-(maleimido)hexanoyl)piperazin-1-yl)-amatoxin: 7'C-(4-(6-(maleimido)hexanamido)piperidin-1-yl)-amatoxin: 7'C-(4-(6-(6-(maleimido)hexanamido)hexanoyl)piperazin-1-yl)-amatoxin; 7'C-(4-(4-((maleimido)methyl)cyclohexanecarbonyl)piperazin-1-yl)-amatoxin; 7'C-(4-(6-(4-((maleimido)methyl)cyclohexanecarboxamido)hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido)ethyl)piperidin-1-yl)-amatoxin; 7'C-(4-(2-(4-((maleimido)methylcyclohexanecarboxamido)ethyl)piperidin-1-yl)-amatoxin; 7'C-(4-(2-(6-(4-((maleimido)methyl)cyclohexanecarboxamido)hexanamido)ethy)piperidin-1-yl)-amatoxin; 7'C-(4-(2-(3-carboxypropanamido)ethyl)piperidin-1-yl)-amatoxin; 7'C-(4-(2-(2-bromoacetamido)ethyl)piperidin-1-yl)-amatoxin; 7'C-(4-(2-(3-(pyridin-2-yldisulfanyl)propanamido)ethyl)piperdin-1-yl)-amatoxin; 7'C-(4-(2-(4-(maleimido)butanamido)ethyl)piperidin-1-yl)-amatoxin; 7C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl)cyclohexanecarboxamido)hexanamido)ethyl)piperidin-1-yl)-amatoxin; 7'C-(3-((6-(maleimido)hexanamido)methyl)pyrrolidin-1-yl)-amatoxin; 7'C-(3-((6-(6-(maleimido)hexanamido)hexanamido)methyl)pyrrolidin-1-yl)-amatoxin: 7C-(3-((4-((maleimido)methyl)cyclohexanecarboxamido)methy)pyrrolidin-1-yl)-amatoxin; 7'C-(3-((6-((4-(maleimido)methyl)cyclohexanecarboxamido)hexanamido)methyl)pyrrolidin-1-yl)-amatoxin; 7'C-(4-(2-(6-(2-(aminooxy)acetamido)hexanamido)ethyl)piperidin-1-yl)-amatoxin; 7'C-(4-(2-(4-(2-(aminooxy)acetamido)butanamido)ethyl)piperdin-1-yl)-amatoxin; 7'C-(4-(4-(2-(aminooxy)acetamido)butanoyl)piperazin-1-yl)-amatoxin; 7C-(4-(6-(2-(aminooxy)acetamido)hexanoyl)piperazin-1-yl)-amatoxin; 7'C-((4-(6-(maleimido)hexanamido)piperdin-1-yl)methyl)-amatoxin; 7'C-((4-(2-(6-(maleimido)hexanamido)ethyl)piperidin-1-yl)methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methy)pyrrolidin-1-yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methylcyclohexanecarboxamido)ethyl)piperazin-1-yl)methyl)-amatoxin; 7C-((4-(2-(6-(4-((maleimido)methyl)cyclohexanecarboxamido)hexanamido)ethy)piperazin-1-yl)methy)-amatoxin; 7'C-((3-((6-(6-(maleimido)hexanamido)hexanamido)-S-methyl)pyrrolidin-1-yl)methyl)-amatoxin; 7C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methy)-amatoxin; 7'C-((3-((6-(4-((maleimido)methyl)cyclohexanecarboxamido)hexanamido)methyl)pyrroidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(4-((maleimido)methyl)cyclohexanecarboxamido)hexanoyl)piperazin-1-yl)methyl)-amatoxin; 7'C-((4-(2-(maleimido)acetyl)piperazin-1-yl)

methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methy)-amatoxin; 7'C-((4-(2-(4-(maleimido)butanamido)ethyl)piperidin-1-yl)methyl)-amatoxin; 7'C-((4-(2-(6-(4-((maleimido)methyl)cyclohexanecarboxamido)hexanamido)ethyl)piperdin-1-yl)methyl)-amatoxin; 7'C-((3-((6-(maleimido)hexanamido)methy)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-1-yl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((4-(2-(6-(2-(aminooxy)acetamido)hexanamido)ethyl)piperidin-1-yl)methyl)-amatoxin; 7'C-((4-(2-(2-(2-(aminooxy)acetamido)acetamido)ethyl)piperdin-1-yl)methyl)-amatoxin; 7'C-((4-(2-(4-(2-(aminooxy)acetamido)butanamido)ethyl)piperidin-1-yl)methyl)-amatoxin; 7C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methylhexanamido)butyl)(methyl)amino)methyl)-amatoxin; 7'C-((3-((6-(4-((maleimido)methyl)cyclohexanecarboxamido)hexanamido)methyl)pyrrolidin-1-yl)-S-methyl)-amatoxin; TC-((3-((6-(4-((maleimido)methylcyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl)piperidin-1-yl)methyl)-amatoxin; 7'C-((4-(2-(3-(pyridine-2-yldisulfanyl)propanamido)ethyl)piperdin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido)ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin.

The foregoing linkers, among others useful in conjunction with the compositions and methods described herein, are described, for example, in US Patent Application Publication No. 2015/0218220, the disclosure of which is incorporated herein by reference in its entirety.

Additional cytotoxins that can be conjugated to antibodies, and antigen-binding fragments thereof, that recognize and bind CD5 for use in directly treating a cancer, autommine condition, or for conditioning a patient (e.g., a human patient) in preparation for hematopoietic stem cell transplant therapy include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, fllgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaftine, vorozole, zeniplatin, and zilascorb, among others.

In some embodiments, the cytotoxin is a pyrrolobenzodiazepine dimer represented by formula (IV):

antigen-binding fragment thereof. Such conjugation reactions are described further herein below.

In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will; (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/

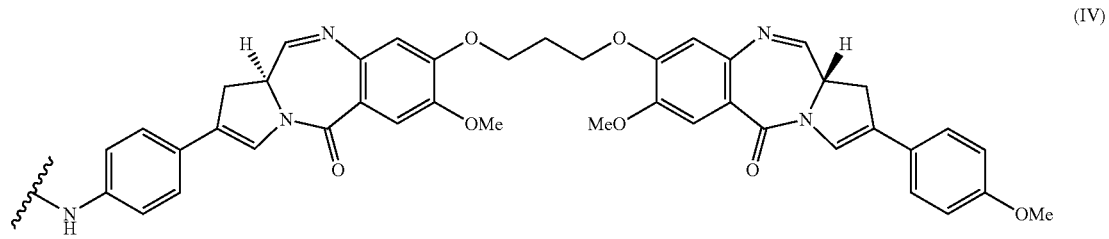 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

(IV)

A variety of linkers can be used to conjugate antibodies, and antigen-binding fragments, described herein (e.g., antibodies, antigen-binding fragments thereof, that recognize and bind CD5 with a cytotoxic molecule.

The term "Linker" as used herein means a divalent chemical moiety comprising a covalent bond or a chain of atoms that covalently attaches an antibody or fragment thereof (Ab) to a drug moiety (D) to form antibody-drug conjugates of the present disclosure (ADCs; Ab-Z-L-D, where D is a cytotoxin). Suitable linkers have two reactive termini, one for conjugation to an antibody and the other for conjugation to a cytotoxin. The antibody conjugation reactive terminus of the linker (reactive moiety, Z) is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. When the term "linker" is used in describing the linker in conjugated form, one or both of the reactive termini will be absent (such as reactive moiety Z, having been converted to chemical moiety Z) or incomplete (such as being only the carbonyl of the carboxylic acid) because of the formation of the bonds between the linker and/or the cytotoxin, and between the linker and/or the antibody or analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation).

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Examples of linkers useful for the synthesis of drug-antibody conjugates include those that contain electrophiles, such as Michael acceptors (e.g., maleimides), activated esters, electron-deficient carbonyl compounds, and aldehydes, among others, suitable for reaction with nucleophilic substituents present within antibodies or antigen-binding fragments, such as amine and thiol moieties. For instance, linkers suitable for the synthesis of drug-antibody conjugates include, without limitation, succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are particularly useful for the conjugation of microtubule-disrupting agents such as auristatins, are described by Doronina et al., Bioconjugate Chem. 17:14-24, 2006, the disclosure of which is incorporated herein by reference as it pertains to linkers for chemical conjugation. Additional linkers suitable for the synthesis of drug-antibody conjugates as described herein include those capable of releasing a cytotoxin by a 1,6-elimination process, (a "self-immolative" group), such as p-aminobenzyl alcohol (PABC), 6-maleimidohexanoic acid, pH-sensitive carbonates, and other reagents described in Jain et al., Pharm. Res. 32:3526-3540, 2015, the disclosure of which is incorporated herein by reference in its entirety. In some embodiments, the linker includes a self-immolative group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743: U.S. Pat. No. 6,759,509; US20040052793: U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 68:8815-8830; and U.S. Pat. No. 7,223,837.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker includes a dipeptide selected from Val-Ala and Val-Cit. In some embodiments, a dipeptide is used in combination with a self-immolative linker.

Linkers suitable for use herein further may include one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted. Non-limiting examples of such groups include $(CH_2)_n$, $(CH_2CH_2O)_n$, and —(C=O)$(CH_2)_n$— units, wherein n is an integer from 1-6, independently selected for each occasion.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, acyl, —C(=O)—, or —$(CH_2CH_2O)_n$— group, wherein n is an integer from 1-6. One of skill in the art will recognize that one or more of the groups listed may be present in the form of a bivalent (diradical) species, e.g., $C_1$-$C_6$ alkylene and the like.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, —$(CH_2)_n$—, —$(CH_2CH_2O)_n$—, PAB, Val-Cit-PAB, Val- Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a —(C=O)(CH$_2$)$_n$— unit, wherein n is an integer from 1-6.

In some embodiments, the linker comprises a —(CH$_2$)$_n$— unit, wherein n is an integer from 2 to 6.

In certain embodiments, the linker of the ADC is N-beta-maleimidopropyl-Val-Ala-para-aminobenzyl (BMP-Val-Ala-PAB).

Linkers that can be used to conjugate an antibody, or an antigen-binding fragment thereof, to a cytotoxic agent include those that are covalently bound to the cytotoxic agent on one end of the linker and, on the other end of the linker, contain a chemical moiety formed from a coupling reaction between a reactive substituent present on the linker and a reactive substituent present within the antibody, or an antigen-binding fragment thereof, that binds CD5. Reactive substituents that may be present within an antibody, or an antigen-binding fragment thereof, that binds CD5 include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids.

Examples of linkers useful for the synthesis of drug-antibody conjugates conjugates include those that contain electrophiles, such as Michael acceptors (e.g., maleimides), activated esters, electron-deficient carbonyl compounds, and aldehydes, among others, suitable for reaction with nucleophilic substituents present within antibodies or antigen-binding fragments, such as amine and thiol moieties. For instance, linkers suitable for the synthesis of drug-antibody conjugates include, without limitation, succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are particularly useful for the conjugation of microtubule-disrupting agents such as auristatins, are described by Doronina et al., Bioconjugate Chem. 17:14-24, 2006, the disclosure of which is incorporated herein by reference as it pertains to linkers for chemical conjugation.

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

Linkers useful in conjunction with the antibody-drug conjugates described herein include, without limitation, linkers containing chemical moieties formed by coupling reactions as depicted in Table 2, below. Curved lines designate points of attachment to the antibody, or antigen-binding fragment, and the cytotoxic molecule, respectively.

TABLE 2

Exemplary chemical moieties formed by coupling reactions in the formation of antibody-drug conjugates

| Exemplary Coupling Reactions | Chemical Moiety Z Formed by Coupling Reactions |
|---|---|
| [3 + 2] Cycloaddition | |
| [3 + 2] Cycloaddition | |
| [3 + 2] Cycloaddition, Esterification | |

TABLE 2-continued

Exemplary chemical moieties formed by coupling reactions in the formation of antibody-drug conjugates

| Exemplary Coupling Reactions | Chemical Moiety Z Formed by Coupling Reactions |
|---|---|
| [3 + 2] Cycloaddition, Esterification | 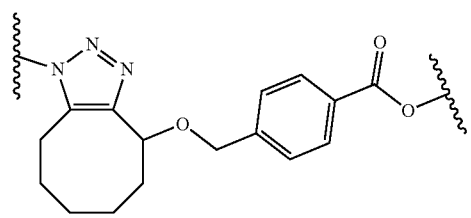 [SMILES: *OC(=O)c1ccc(COC2CCCCCc3c2nnn3*)cc1] |
| [3 + 2] Cycloaddition, Esterification | 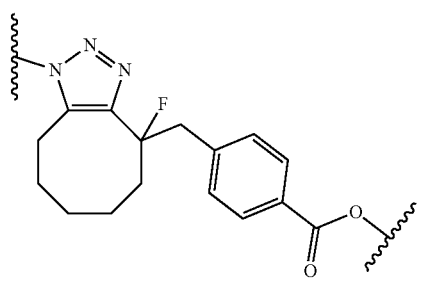 [SMILES: *OC(=O)c1ccc(CC2(F)CCCCCc3c2nnn3*)cc1] |
| [3 + 2] Cycloaddition, Esterification | 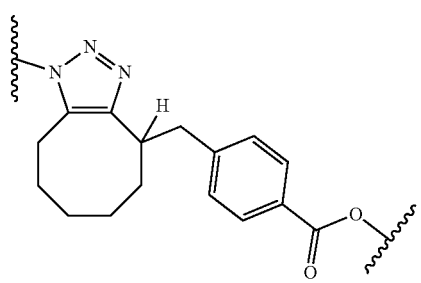 [SMILES: *OC(=O)c1ccc(CC2CCCCCc3c2nnn3*)cc1] |
| [3 + 2] Cycloaddition, Esterification | 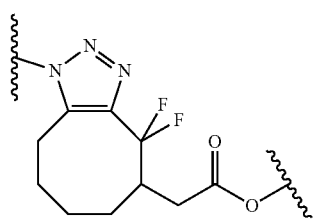 [SMILES: *OC(=O)CC1CCCCc2c(nnn2*)C1(F)F] |
| [3 + 2] Cycloaddition, Esterification | 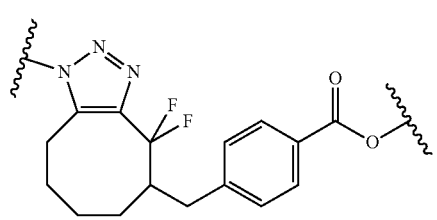 [SMILES: *OC(=O)c1ccc(CC2CCCCc3c(nnn3*)C2(F)F)cc1] |

TABLE 2-continued
Exemplary chemical moieties formed by coupling reactions in the formation of antibody-drug conjugates
| Exemplary Coupling Reactions | Chemical Moiety Z Formed by Coupling Reactions |
|---|---|
| [3 + 2] Cycloaddition, Esterification | 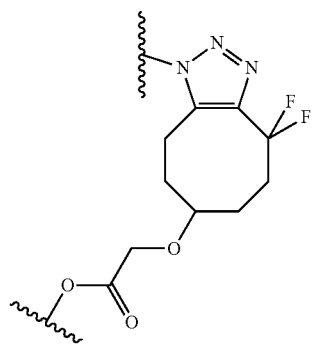 [SMILES: *OC(=O)COC1CCc2c(nnn2*)C(F)(F)CC1] |
| [3 + 2] Cycloaddition, Esterification | 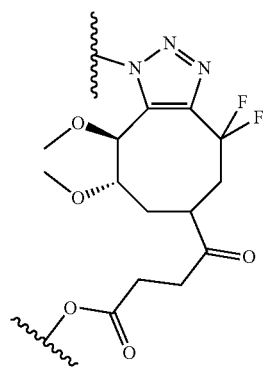 [SMILES: *OC(=O)CCC(=O)C1C[C@H](OC)[C@@H](OC)c2c(nnn2*)C(F)(F)C1] |
| [3 + 2] Cycloaddition, Esterification | 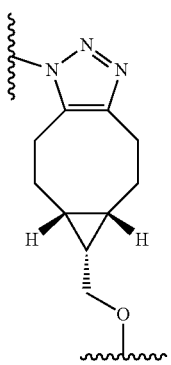 [SMILES: *OC[C@@H]1[C@@H]2CCc3c(nnn3*)CC[C@@H]21] |
| [3 + 2] Cycloaddition, Esterification | 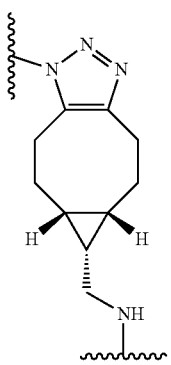 [SMILES: *NC[C@@H]1[C@@H]2CCc3c(nnn3*)CC[C@@H]21] |

TABLE 2-continued

Exemplary chemical moieties formed by coupling reactions in the formation of antibody-drug conjugates

| Exemplary Coupling Reactions | Chemical Moiety Z Formed by Coupling Reactions |
|---|---|
| [3 + 2] Cycloaddition, Esterification | (structure: triazole fused to dibenzocyclooctene with O-linker) |
| [3 + 2] Cycloaddition, Esterification | (structure: triazole fused to butyl-substituted dibenzocyclooctene with O-linker) |
| [3 + 2] Cycloaddition | (structure: triazole fused to dibenzazacyclooctene) |
| Michael addition | (structure: thiosuccinimide) |
| Michael addition | (structure: methoxy-substituted thiosuccinimide derivative) |
| Imine condensation, Amidation | (structure: oxime-O-CH2-C(=O)-NH-) |
| Imine condensation | (structure: oxime C=N-O-) |

TABLE 2-continued

Exemplary chemical moieties formed by coupling reactions in the formation of antibody-drug conjugates

| Exemplary Coupling Reactions | Chemical Moiety Z Formed by Coupling Reactions |
|---|---|
| Disulfide formation | [structure: S–S disulfide linkage] |
| Thiol alkylation | [structure: S–CH2–C(=O)– linkage] |
| Condensation, Michael addition | [structure showing amidine NH/NH linked via propyl chain to thioether-substituted succinimide N] |

One of skill in the art will recognize that a reactive substituent Z attached to the linker and a reactive substituent on the antibody or antigen-binding fragment thereof, are engaged in the covalent coupling reaction to produce the chemical moiety Z, and will recognize the reactive substituent Z. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z, suitable for reaction with a reactive substituent on the antibody, or antigen-binding fragment thereof, to form the chemical moiety Z.

As depicted in Table 3, examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substitutents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i)N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of seine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z. For instance, Z may be a Michael acceptor (e.g., maleimide), activated ester, electron-deficient carbonyl compound, or an aldehyde, among others.

In some embodiments, the ADC comprises an anti-CD5 antibody conjugated to an amatoxin of any of formulae I, IA, IB, II, IIA, or IIB as disclosed herein via a linker and a chemical moiety Z. In some embodiments, the linker includes a a dipeptide. In some embodiments, the linker includes a dipeptide selected from Val-Ala and Val-Cit. In some embodiments, the linker includes a para-aminobenzyl group (PAB). In some embodiments, the linker includes the moiety PAB-Cit-Val. In some embodiments, the linker includes the moiety PAB-Ala-Val. In some embodiments, the linker includes a —((C=O)(CH$_2$)$_n$— unit, wherein n is an integer from 1-6. In some embodiments, the linker is -PAB-Cit-Val-((C=O)(CH$_2$)$_n$—.

In some embodiments, the linker includes a —(CH$_2$)$_n$— unit, where n is an integer from 2-6.

In some embodiments, the linker is -PAB-Cit-Val-((C=O)(CH$_2$)$_n$—. In some embodiments, the linker is -PAB-Ala-Val-((C=O)(CH$_2$)$_n$—. In some embodiments, the linker is —(CH$_2$)$_n$—. In some embodiments, the linker is —((CH$_2$)$_n$—, wherein n is 6.

In some embodiments, the chemical moiety Z is selected from Table 1. In some embodiments, the chemical moiety Z is

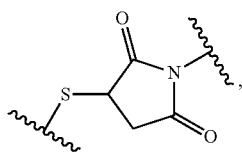

where S is a sulfur atom which represents the reactive substituent present within an antibody, or antigen-binding fragment thereof, that binds CD5 (e.g., from the —SH group of a cysteine residue).

In some embodiments, the linker L and the chemical moiety Z, taken together as L-Z, is

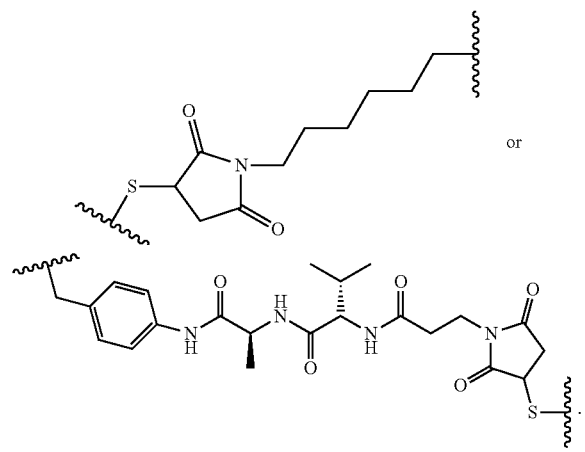

One of skill in the art will recognize the linker-reactive substituent group structure, prior to conjugation with the antibody or antigen binding fragment thereof, includes a maleimide as the group Z. The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

In some embodiments, the linker-reactive substituent group structure, prior to conjugation with the antibody or antigen binding fragment thereof, is:

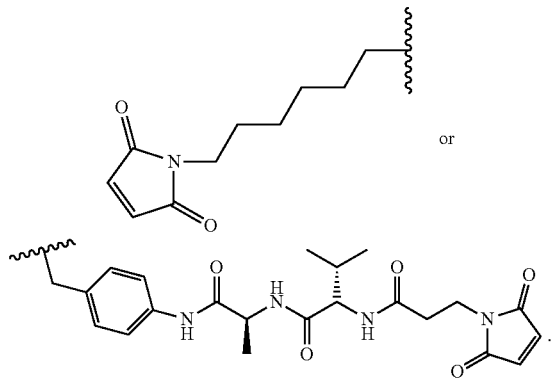

Preparation of Antibody-Drug Conjugates

In the ADCs of formula I as disclosed herein, an antibody or antigen binding fragment thereof is conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z, followed by reaction with a reactive substituent of an antibody or antigen binding fragment thereof as described herein above to form an ADC of formula D-L-Z-Ab, such as Am-Z-L-Ab. Additional methods for preparing ADC are described herein.

In another aspect, the antibody or antigen binding fragment thereof has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the antibody or antigen binding fragment thereof can have one or more carbohydrate groups that can be chemically modified to have one or more sulfhydryl groups. The ADC is then formed by conjugation through the sulfhydryl group's sulfur atom as described herein above.

In yet another aspect, the antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

Methods of Treatment

As described herein, hematopoietic stem cell transplant therapy can be administered to a subject in need of treatment so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo, thereby treating the pathology associated with the defect or depletion in the endogenous blood cell population. The compositions and methods described herein can thus be used to treat a non-malignant hemoglobinopathy (e.g., a hemoglobinopathy selected from the group consisting of sickle cell anemia, thalassemia, Fanconi anemia, aplastic anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses. Gaucher's Disease, Hurlers Disease, sphingolipidoses, and metachromatic leukodystrophy).

Additionally or alternatively, the compositions and methods described herein can be used to treat a malignancy or proliferative disorder, such as a hematologic cancer, myeloproliferative disease. In the case of cancer treatment, the compositions and methods described herein may be administered to a patient prior to hematopoietic stem cell transplantation therapy in order to deplete a population of immune cells that cross-react with, and mount an immune response against, non-self hematopoietic stem cells, such as those expressing one or more non-self MHC antigens. This serves to prevent or reduce the likelihood of rejection of the transplanted hematopoietic stem cell grafts, allowing the transplanted hematopoietic stem cells to home to a stem cell niche and establish productive hematopoiesis. This, in turn, can re-constitute a population of cells depleted during cancer cell eradication, such as during systemic chemotherapy. Exemplary hematological cancers that can be treated using the compositions and methods described herein include, without limitation, acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated with the compositions and methods described herein include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

The antibodies, or antigen-binding fragments thereof, and conjugates described herein may be used to induce solid organ transplant tolerance. For instance, the compositions and methods described herein may be used to deplete or ablate a population of immune cells prior to hematopoietic stem cell transplantation. Following such depletion of cells from the target tissues, a population of stem or progenitor cells from an organ donor (e.g., hematopoietic stem cells from the organ donor) may be administered to the transplant recipient, and following the engraftment of such stem or progenitor cells, a temporary or stable mixed chimerism may be achieved, thereby enabling long-term transplant organ tolerance without the need for further immunosuppressive agents. The likelihood of rejection of the transplanted graft can be reduced, or rejection may be prevented altogether, by administration of the anti-CD5 antibody, or antigen-binding fragment thereof. In this way, the compositions and methods described herein may be used to induce transplant tolerance in a solid organ transplant recipient (e.g., a kidney transplant, lung transplant, liver transplant, and heart transplant, among others). The compositions and methods described herein are well-suited for use in connection the induction of solid organ transplant tolerance, for instance, because a low percentage temporary or stable donor engraftment is sufficient to induce long-term tolerance of the transplanted organ.

In addition, the compositions and methods described herein can be used to treat cancers directly, such as cancers characterized by cells that are CD5+. For instance, the compositions and methods described herein can be used to treat leukemia, particularly in patients that exhibit CD5+ leukemic cells. By depleting CD5+ cancerous cells, such as leukemic cells, the compositions and methods described herein can be used to treat various cancers directly. Exemplary cancers that may be treated in this fashion include hematological cancers, such as acute myeloid leukemia, acute lymphoid leukemia, chronic myeloid leukemia, chronic lymphoid leukemia, multiple myeloma, diffuse large B-cell lymphoma, and non-Hodgkin's lymphoma, In addition, the compositions and methods described herein can be used to treat autoimmune disorders. For instance, an antibody, or antigen-binding fragment thereof, can be administered to a subject, such as a human patient suffering from an autoimmune disorder, so as to kill a CD5+ immune cell. The CD5+ immune cell may be an autoreactive lymphocyte, such as a T-cell that expresses a T-cell receptor that specifically binds, and mounts an immune response against, a self antigen. By depleting self-reactive, CD5+ cells, the compositions and methods described herein can be used to treat autoimmune pathologies, such as those described below. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during autoimmune cell eradication.

Autoimmune diseases that can be treated using the compositions and methods described herein include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

For instance, using the compositions and methods described herein, one of skill in the art can administer to a subject suffering from an autoimmune disorder an anti-CD5 antibody, or antigen-binding fragment thereof, in a quantity sufficient to treat the autoimmune pathology. For instance, the subject may be suffering from scleroderma, multiple sclerosis, ulcerative colitis, Chrohn's disease, and/or Type 1 diabetes. To ameliorate one or more of these conditions, a physician of skill in the art can prescribe and administer to the subject an anti-CD5 antibody, or fragment thereof, such as an antibody, or fragment thereof, that is bound to a cytotoxic agent. The antibody, or fragment thereof, may be conjugated to a cytotoxic agent using conjugation techniques and linkers detailed above. A variety of cytotoxic agents can be conjugated to an anti-CD5 antibody, or antigen-binding fragment thereof, in order to deplete a population of endogenous, autoreactive CD5+ T cells, B cells, or NK cells in a subject. For instance, the antibody or antigen-binding fragment thereof may be conjugated to an amatoxin or another cytotoxin moiety described herein.

In preparation for therapy, the physician may assess the quantity or concentration of autoreactive T cells, B cells, and/or NK cells in a sample isolated from a subject. This may be done, for instance, using FACS analysis techniques known in the art. One of skill in the art may then administer to the subject an antibody, or fragment thereof, either alone or conjugated to a cytotoxin, so as to deplete the population of autoreactive T cells, B cells, and/or NK cells. To evaluate the efficacy of the therapy, the physician may determine the quantity or concentration of autoreactive T cells, B cells, and/or NK cells in a sample isolated from the patient at a time subsequent to the administration of the anti-CD5 antibody, or fragment thereof. A determination that the quantity or concentration of autoreactive T cells, B cells, and/or NK cells in a sample isolated from the subject following therapy relative to the quantity or concentration of T cells, B cells, or NK cells prior to therapy provides an indication that the patient is responding to the anti-CD5 antibody, or fragment thereof.

Antibody drug conjugates comprising anti-CD5 antibodies, or antigen-binding fragments thereof, can also be used in combination with CAR T therapy. Specifically, an effective amount of an anti-CD5 antibody drug conjugate can be administered to a patient in need thereof prior to CAR T treatment in order to deplete native T cells. Depletion of native T cells expressing CD5 using the methods and compositions described herein can provide for more effective transfer of engineered T cells used in CAR T therapy.

Routes of Administration and Dosing

Antibodies, or antigen-binding fragments thereof, described herein can be administered to a patient (e.g., a human patient in need of hematopoietic stem cell transplant therapy) in a variety of dosage forms. For instance, antibodies, or antigen-binding fragments thereof, described herein can be administered to a patient in need of hematopoietic stem cell transplant therapy and/or suffering from cancer or an autoimmune disease in the form of an aqueous solution, such as an aqueous solution containing one or more pharmaceutically acceptable excipients. Exemplary pharmaceutically acceptable excipients for use with the compositions and methods described herein are viscosity-modifying agents. The aqueous solution may be sterilized using techniques known in the art.

The antibodies, and antigen-binding fragments, described herein may be administered by a variety of routes, such as orally, transdermally, subcutaneously, intranasally, intravenously, intramuscularly, intraocularty, or parenterally. The most suitable route for administration in any given case will depend on the particular antibody or antigen-binding fragment administered, the patient, pharmaceutical formulation methods, administration methods (e.g., administration time and administration route), the patient's age, body weight, sex, severity of the diseases being treated, the patient's diet, and the patient's excretion rate.

The effective dose of an antibody, or an antigen-binding fragment thereof, described herein can range, for example from about 0.001 to about 100 mg/kg (e.g., about 0.001 mg/kg to about 0.01 mg/kg, about 0.01 mg/kg to about 0.1 mg/kg, about 0.1 mg/kg to about 1 mg/kg, about 1 mg/kg to about 10 mg/kg, about 10 mg/kg to about 100 mg/kg) of body weight per single (e.g., bolus) administration, multiple administrations, or continuous administration, or to achieve an optimal serum concentration (e.g., a serum concentration of about 0.0001-about 5000 µg/mL (e.g., about 0.0001-0.001 µg/mL, about 0.001-0.01 µg/mL, about 0.01-0.1 µg/mL, about 0.1-1 µg/mL, about 1-10 µg/mL, about 10-100 µg/mL, about 100-1000 µg/mL, about 1000-2000 µg/mL, about 2000-3000 µg/mL, or about 3000-5000 µg/mL) of the antibody, or an antigen-binding fragment thereof. The dose may be administered one or more times (e.g., 2-10 times) per day, week, or month to a subject (e.g., a human) undergoing conditioning therapy in preparation for receipt of a hematopoietic stem cell transplant. The antibody or antigen-binding fragment thereof can be administered to the patient at a time that optimally promotes engraftment of the exogenous hematopoietic stem cells, for instance, at a time that optimally depletes CD5+ T cells, B cells, or NK cells that cross-react with a non-self hematopoietic stem cell antigen, such as a non-self MHC antigen, prior to hematopoietic stem cell transplantation. For example, anti-CD5 antibodies, and antigen-binding fragments thereof, may be administered to a patient undergoing hematopoietic stem cell transplant therapy from about 1 hour to about 1 week (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, or about 7 days) or more prior to administration of the exogenous hematopoietic stem cell transplant. The half-life of the antibody may be between about 1 hour and about 24 hours (e.g., about 1 hour, about 2 hours, about 3 hours, about 4 hours, about 5 hours, about 6 hours, about 7 hours, about 8 hours, about 9 hours, about 10 hours, about 11, hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours).

In one embodiment, an anti-CD5 antibody (or Fc containing fragment thereof) has a reduced half life (compared to a wild type Fc region) where the Fc region of the antibody comprises an H435A mutation (numbering according to the EU index).

According to the methods disclosed herein, a physician of skill in the art can condition a patient, such as a human patient, so as to promote the engraftment of exogenous hematopoietic stem cell grafts prior to hematopoietic stem cell transplant therapy. To this end, a physician of skill in the art can administer to the human patient an antibody, or antigen-binding fragment thereof, capable of binding CD5, such as an anti-CD5 antibody described herein. The antibody, or fragment thereof, may be covalently conjugated to a toxin, such as a cytotoxic molecule described herein or known in the art, or an Fc domain. For instance, an anti-CD5 antibody, or antigen-binding fragment thereof, can be covalently conjugated to a cytotoxin, such as *Pseudomonas* exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof. This conjugation can be performed using covalent bond-forming techniques described herein or known in the art. The antibody, antigen-binding fragment thereof, or antibody-drug conjugate, can subsequently be administered to the patient, for example, by intravenous administration, prior to transplantation of exogenous hematopoietic stem cells (such as autologous, syngeneic, or allogeneic hematopoietic stem cells) to the patient.

The anti-CD5 antibody, antigen-binding fragment thereof, or antibody-drug conjugate, can be administered in an amount sufficient to reduce the quantity of endogenous T cells, B cells, and/or NK cells, such as bone marrow resident T cells, for example, by about 10%, about 20%, about 30%, about 40%, about 50%, about 60%, about 70%, about 80%, about 90%, about 95%, or more prior to hematopoietic stem cell transplant therapy. For example, the anti-CD5 antibody, antigen-binding fragment thereof, or antibody-drug conjugate, can be administered in an amount sufficient to reduce the quantity of endogenous T cells, B cells, and/or NK cells, such as bone marrow resident T cells, for example, by about 10%-20%, by about 20-30%, by about 30-40%, by about 40-50%, by about 50-60%, by about 60-70%, by about 70%-80%, by about 80%-90%, by about 90%-95%, or more prior to hematopoietic stem cell transplant therapy. For example, the anti-CD5 antibody, antigen-binding fragment thereof, or antibody-drug conjugate, can be administered in an amount sufficient to reduce the quantity of endogenous T cells, B cells, and/or NK cells, such as bone marrow resident T cells, for example, by at least about 10%, by at least about 20%, by at least about 30%, by at least about 40%, by at least about 50%, by at least about 60%, by at least about 70%, by at least about 80%, by at least about 90%, by at least about 95%, or more prior to hematopoietic stem cell transplant therapy. The reduction in T cell count can be monitored using conventional techniques known in the art, such as by FACS analysis of cells expressing characteristic T cell surface antigens in a blood sample withdrawn from the patient at varying intervals during conditioning therapy. For instance, a physician of skill in the art can withdraw a bone marrow sample from the patient at various time points during conditioning therapy and determine the extent of endogenous T cell reduction by conducting a FACS analysis to elucidate the relative concentrations of T cells in the sample using antibodies that bind to T cell marker antigens. According to some embodiments, when the concentration of T cells has reached a minimum value in response to conditioning therapy with an anti-CD5 antibody, antigen-binding fragment thereof, or antibody-drug conjugate, the physician may conclude the conditioning therapy, and may begin preparing the patient for hematopoietic stem cell transplant therapy.

The anti-CD5 antibody, antigen-binding fragment thereof, or antibody-drug conjugate, can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, or antibody-drug conjugate, can be administered to the patient at a dosage of, for example, from about 0.001 mg/kg to about 100 mg/kg prior (e.g., about 0.001 mg/kg to about 0.01 mg/kg, about 0.01 mg/kg to about 0.1 mg/kg, about 0.1 mg/kg to about 1 mg/kg, about 1 mg/kg to about 10 mg/kg, about 10 mg/kg to about 100 mg/kg) to administration of a hematopoietic stem cell graft to the patient. The antibody, antigen-binding fragment thereof, or antibody-drug conjugate, can be administered to the patient at a time that optimally promotes engraftment of the exogenous hematopoietic stem cells, for instance, from about 1 hour to about 1 week (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, or about 7 days) or more prior to administration of the exogenous hematopoietic stem cell transplant.

Following the conclusion of conditioning therapy, the patient may then receive an infusion (e.g., an intravenous infusion) of exogenous hematopoietic stem cells, such as from the same physician that performed the conditioning therapy or from a different physician. The physician may administer the patient an infusion of autologous, syngeneic, or allogeneic hematopoietic stem cells, for instance, at a dosage of from about $1 \times 10^3$ to about $1 \times 10^9$ hematopoietic stem cells/kg (about $1 \times 10^3$ hematopoeitic stem cells to about $1 \times 10^4$, about $1 \times 10^4$ hematopoeitic stem cells to about $1 \times 10^5$, about $1 \times 10^5$ hematopoeitic stem cells to about $1 \times 10^8$, about $1 \times 10^8$ hematopoeitic stem cells to about $1 \times 10^7$, or about $1 \times 10^8$ hematopoeitic stem cells to about $1 \times 10^9$). The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T lymphocytes, and B lymphocytes) following administration of the transplant. This analysis may be conducted, for example, from about 1 hour to about 6 months, or more, following hematopoietic stem cell transplant therapy (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, or more). A finding that the concentration of hematopoietic stem cells or cells of the hematopoietic lineage has increased (e.g., by about 1%, about 2%, about 3%, about 4%, about 5%, about 6%, about 7%, about 8%, about 9%, about 10%, about 20%, about 30%, about 40%, about 50%, about 60%, about 70%, about 80%, about 90%, about 100%, about 200%, about 500%, or more) following the transplant therapy relative to the concentration of the corresponding cell type prior to transplant therapy provides one indication that treatment with the anti-CD5 antibody, antigen-binding fragment thereof, or antibody-drug conjugate, has successfully promoted engraftment of the transplanted hematopoietic stem cell graft.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: In Vitro Binding Analysis of Anti-CD5 Antibodies

To determine the binding characteristics of anti-CD5 antibody 5D7 hIgG1, antibody binding studies were performed at 25 degrees celsius in 1×PBS supplemented with 0.1% w/v bovine serum albumin with a Pall ForteBio Octet Red96 using biolayer interferometry (BLI). The purified human anti-CD5 antibody (5D7) was immobilized onto anti-human Fc biosensors (AHC; Pall ForteBio 18-5063) and incubated with 50 nM of purified human CD5 ectodomain). The binding characteristics of anti-CD5 antibody 5D7 are shown in Table 3. Anti-human CD5 antibody 5D7 as used in Examples 1 to 5 is a humanized version of murine antibody 5D7 (see US 2008/0254027). The sequences of antibody 5D7 as used herein are described in SEQ ID Nos: 257 and 258 (heavy and light chain variable region amino acid sequences) and SEQ ID Nos: 29 to 34 (heavy and light chain CDRs).

TABLE 3

| Binding kinetics of 5D7 to human CD5 ectodomain | | | | | | |
|---|---|---|---|---|---|---|
| Antibody | Conc. (nM) | Response (nm) | $K_D$ (M) | $K_{ON}$ (1/Ms) | $K_{DIS}$ (1/s) | Full $R^2$ |
| 5D7 | 50 | 0.6696 | 1.41E−10 | 2.39E+05 | 3.36E−05 | 0.9996 |

Example 2: In Vitro Cell Line Binding Analysis of Anti-CD5 Antibodies

MOLT-4 cells (i.e., an immortalized human T lymphoblast cell line) were plated at 20.000 cells/well and stained with a titration of the indicated murine anti-CD5 antibodies (i.e., L17F12, UCHT2, 205919, and CRIS-1) for 2 hours at 4° C. Secondary anti-mouse AF488 stain, at a constant amount, was added for 30 minutes at 4° C. After washing, plates were run on a flow cytometer and binding of the indicated antibody (and the negative control, i.e., mIgG1) was determined based on geometric mean fluorescence intensity in the AF488 channel. Results from these assays are provided in FIG. 1.

As shown in FIG. 1, the murine anti-CD5 antibodies L17F12 (Thermo Fisher), UCHT2 (BioLegend), 205919 (Novus Biologicals), and CRIS-1 (Novus Biologicals) bound to human T lymphoblast cells (i.e. MOLT-4 cells), with an $EC_{50}$=207 pM (L17), 354 pM (UCH), 1350 pM (205), and 43 pM (CRIS).

Example 3: In Vitro Primary Cell Binding Analysis of Anti-CD5 Antibodies

Primary human T-cells were plated at $8 \times 10^4$ cells/well and stained with a titration of the human anti-CD5 antibody 5D7 for 2 hours at 37° C. Secondary anti-mouse AF488 stain, at a constant amount, was added for 30 minutes at 4° C. After washing, plates were run on a flow cytometer and binding of the anti-CD5 5D7 antibody (and the negative control, i.e., hIgG1) was determined based on geometric mean fluorescence intensity in the AF488 channel. Results from these assays are provided in FIG. 2.

Figure 2:
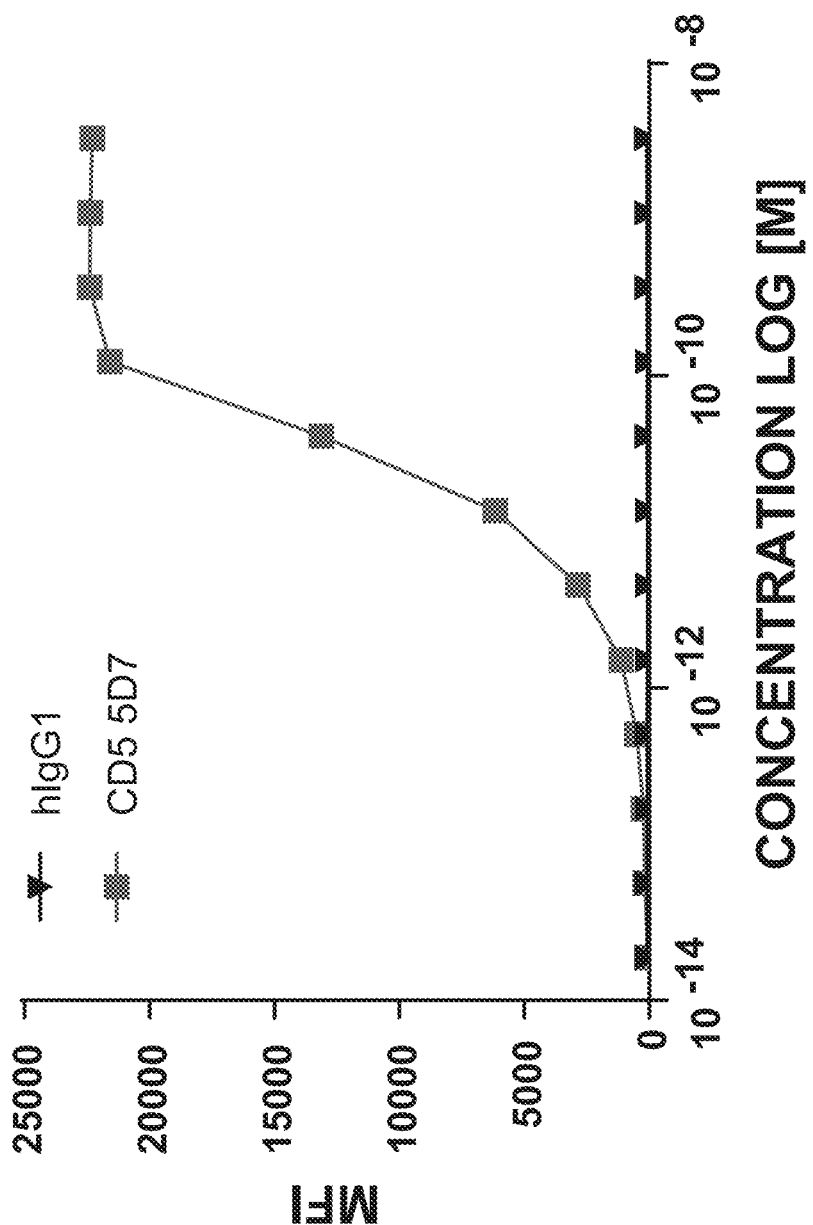
FIG. 2 graphically depicts the results of an in vitro primary cell binding assay in which each of the indicated anti-CD5 antibodies or a negative control (i.e., hIgG1) was incubated with primary human T-cells followed by incubation of a fluorophore-conjugated anti-IgG antibody. Signal was detected through flow cytometry and is indicated as the geometric mean fluorescence intensity (y-axis) as a function of anti-CD5 antibody concentration (x-axis).

As shown in FIG. 2, the anti-CD5 antibody 5D7 bound to primary human T-cells with an $EC_{50}=3.0$ pM.

Example 4. In Vitro Analysis of an Anti-CD5-Amatoxin Antibody Drug Conjugate (ADC) Using an In Vitro T-Cell Killing Assay The anti-CD5 antibody 5D7 was conjugated to an amatoxin (amanitin) with a cleavable linker to form an anti-CD5 5D7ADC. Anti-CD5 5D7-ADCs having a drug to antibody ratio (DAR) of about 6 (interchain DAR6) were tested, as well as anti-CD5 5D7-ADCs having a DAR of about 2 (prepared using site-specific conjugation via a D265C mutation). Further, a fast half-life variant of the anti-CD5 5D7-ADC was generated through the introduction of an H435A mutation within the Fc region.

Each anti-CD5 5D7-ADC was assessed using an in vitro human T-cell killing assay. Cryopreserved negatively-selected primary human T cells were thawed and stimulated with anti-CD3 antibodies and IL-2. At the start of the assay, $2 \times 10^4$ T cells were seeded per well of a 384 well plate and the indicated ADCs or non-conjugated anti-CD5 antibody were added to the wells at various concentrations between 0.003 nm and 30 nm before being placed in an incubator with 37° C. and 5% $CO_2$. Following five days of culture, cells were analyzed by flow cytometry. Cells were stained with a viability marker 7-AAD and run on a volumetric flow cytometer.

Numbers of viable T-cells (FIGS. 3A and 3B) were determined by FSC vs SSC and 7-AAD. A non-conjugated anti-CD5 5D7 antibody served as a comparator (FIG. 3A).

Figure 3A:
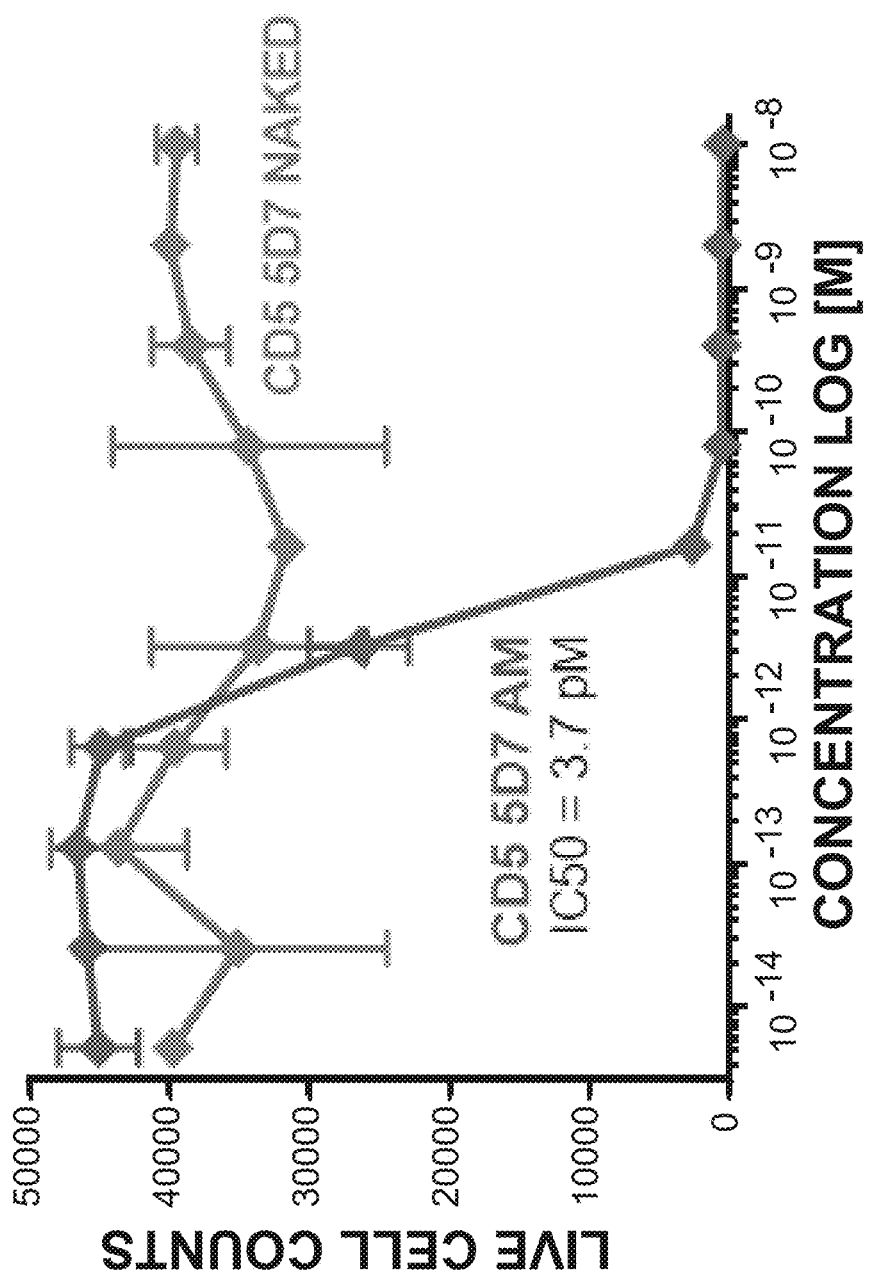
FIGS. 3A and 3B graphically depict results of an in vitro T cell killing assay including an anti-CD5-amanitin ADC (i.e., 5D7-AM or "CD5 AM") having an interchain conjugated amanitin with an average drug-to-antibody ratio (DAR) of 6 (FIG. 3A) or a site-specific conjugated amanitin DAR of 2 (FIG. 3B).
Figure 3B:
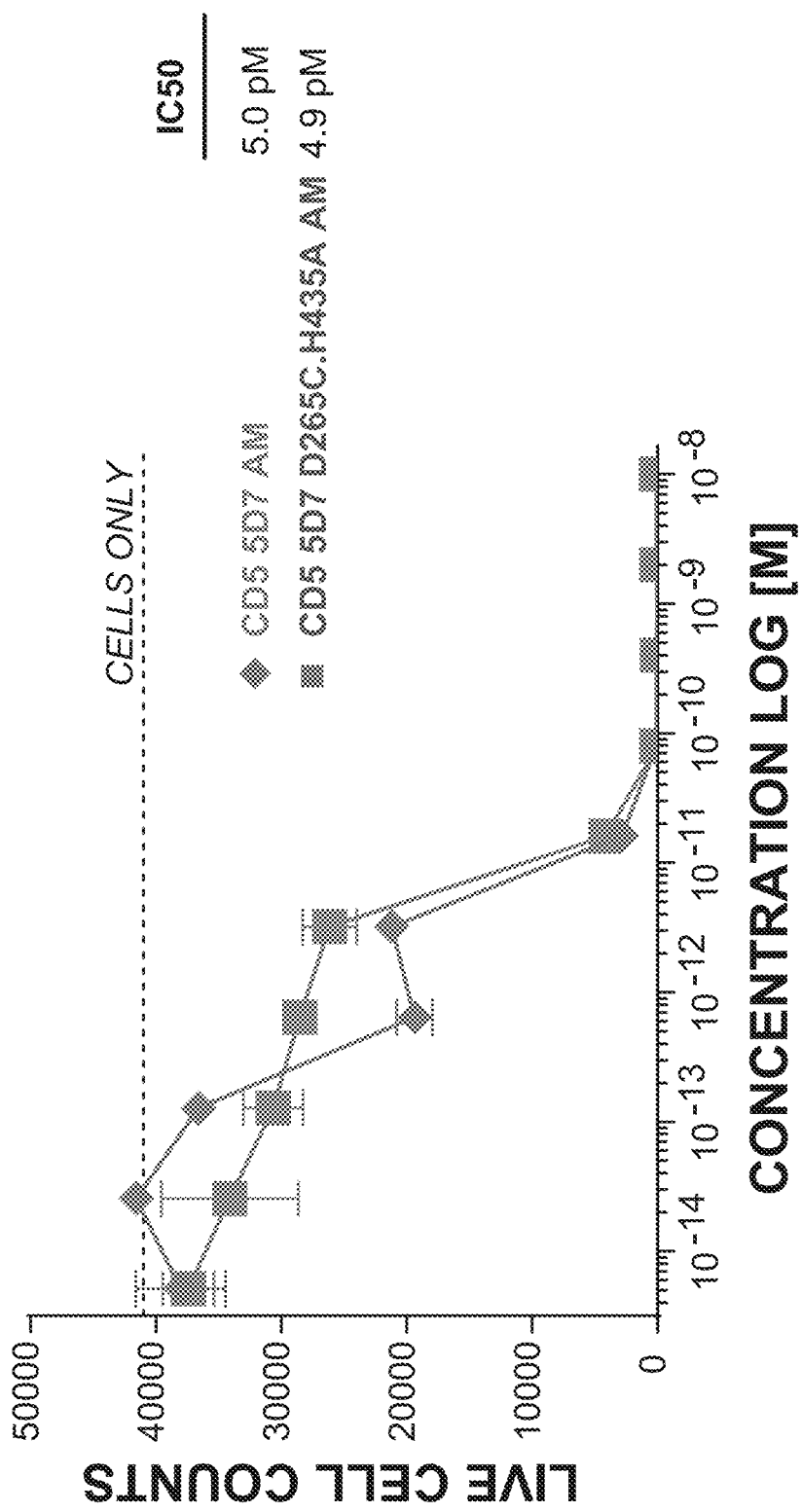

As shown in FIG. 3A, anti-CD5 5D7-ADCs having a DAR of about 6 exhibited potent and specific killing of human T cells (IC50=3.7 pm) whereas T cells remained viable in the presence of non-conjugated ("naked") anti-CD5 5D7 antibodies. As shown in FIG. 3B, ADCs having a site-specific (D265C) DAR of about 2 retained a potent level of T-cell killing (IC50=5.0 pm) similar to that of the DAR 6 ADCs. The fast-half life variant of the anti-CD5 5D7-ADC (H435A) exhibited a similar level of T-cell killing (IC50=4.9 pm; FIG. 3B).

Example 5. Analysis of T-Cell Depletion Using a hNSG Mouse Model

In vivo T-cell depletion assays were conducted using humanized NSG mice (Jackson Laboratories). Anti-CD5 antibody 5D7 was conjugated to amatoxin (amanitin) with a cleavable linker to form an anti-CD5 5D7-ADC. Anti-CD5 5D7-ADCs were prepared either as a DAR of about 6 or aDAR of about 2, as described above. Each anti-CD5 5D7ADC (DAR6 or DAR2) was administered as a single intravenous injection (0.3 mg/kg, 1 mg/kg, or 3 mg/kg for DAR6 ADCs, or 1 mg/kg or 3 mg/kg for DAR2 ADCs) to the humanized mouse. Peripheral blood cells, bone marrow, or thymic samples were collected on Day 7 and the absolute number of CD3+ T-cells was determined by flow cytometry (see FIGS. 4A-4C for DAR2 ADCs, and 5A-5C for DAR6 ADCs).

Figure 4A:
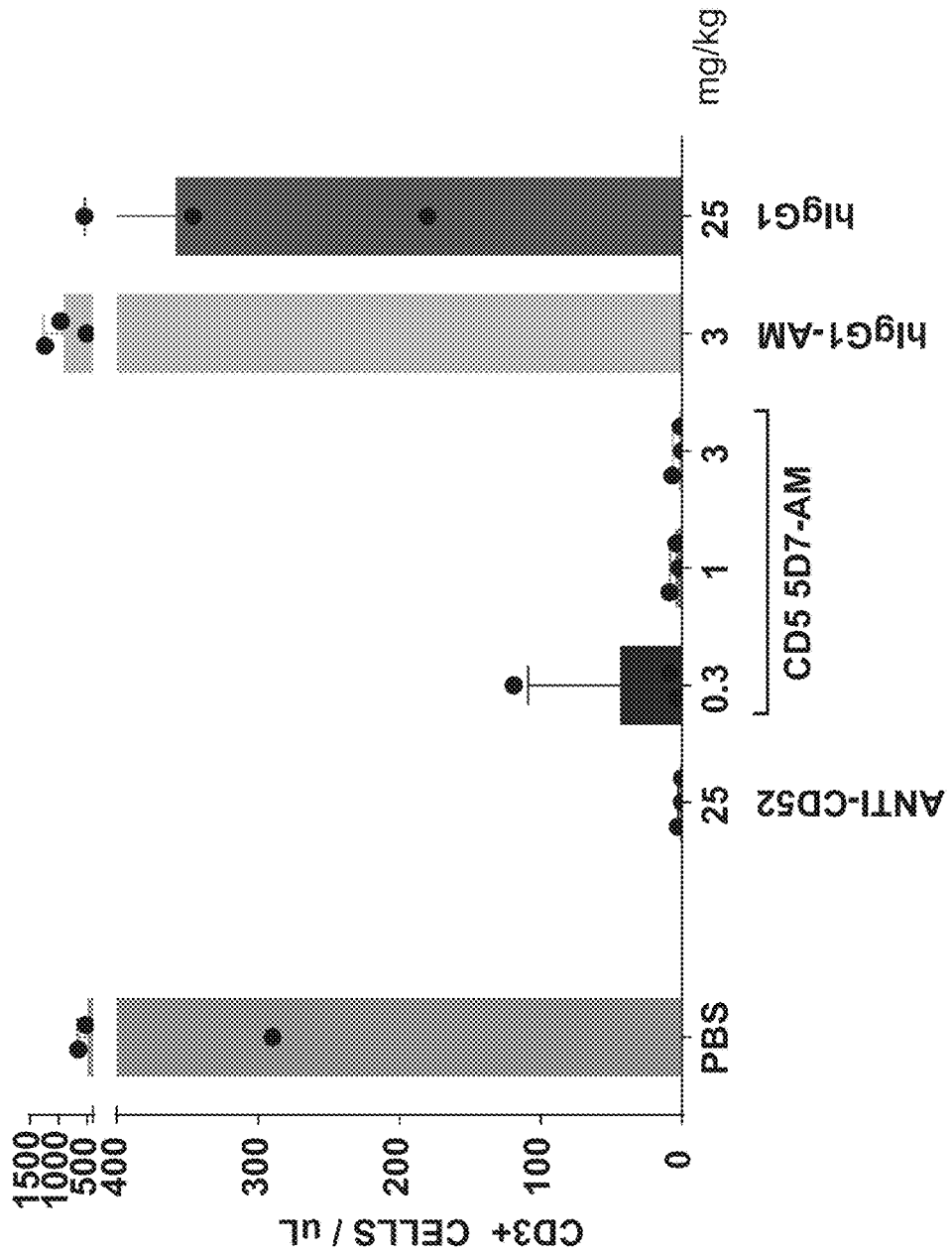
FIGS. 4A-4B graphically depict the results of an in vivo T-cell depletion assay showing the absolute levels of T-cells (CD3+ cells; y-axis) in the peripheral blood (FIG. 4A) and bone marrow (FIG. 4B) of humanized NSG mice 7 days after a single administration of 0.3 mg/kg, 1 mg/kg, or 3 mg/kg of an anti-CD5 5D7 amanitin ADC (i.e., CD5 5D7-AM) having an interchain DAR of 6. For comparison, FIGS. 4A-4B also show the level of T-cell depletion following treatment of humanized NSG mice with the indicated controls (i.e., 25 mg/kg anti-CD52 antibody; 3 mg/kg hIgG1-amanitin ADC (i.e., hIgG1-AM), 25 mg/kg hIgG1, or PBS).
Figure 4B:
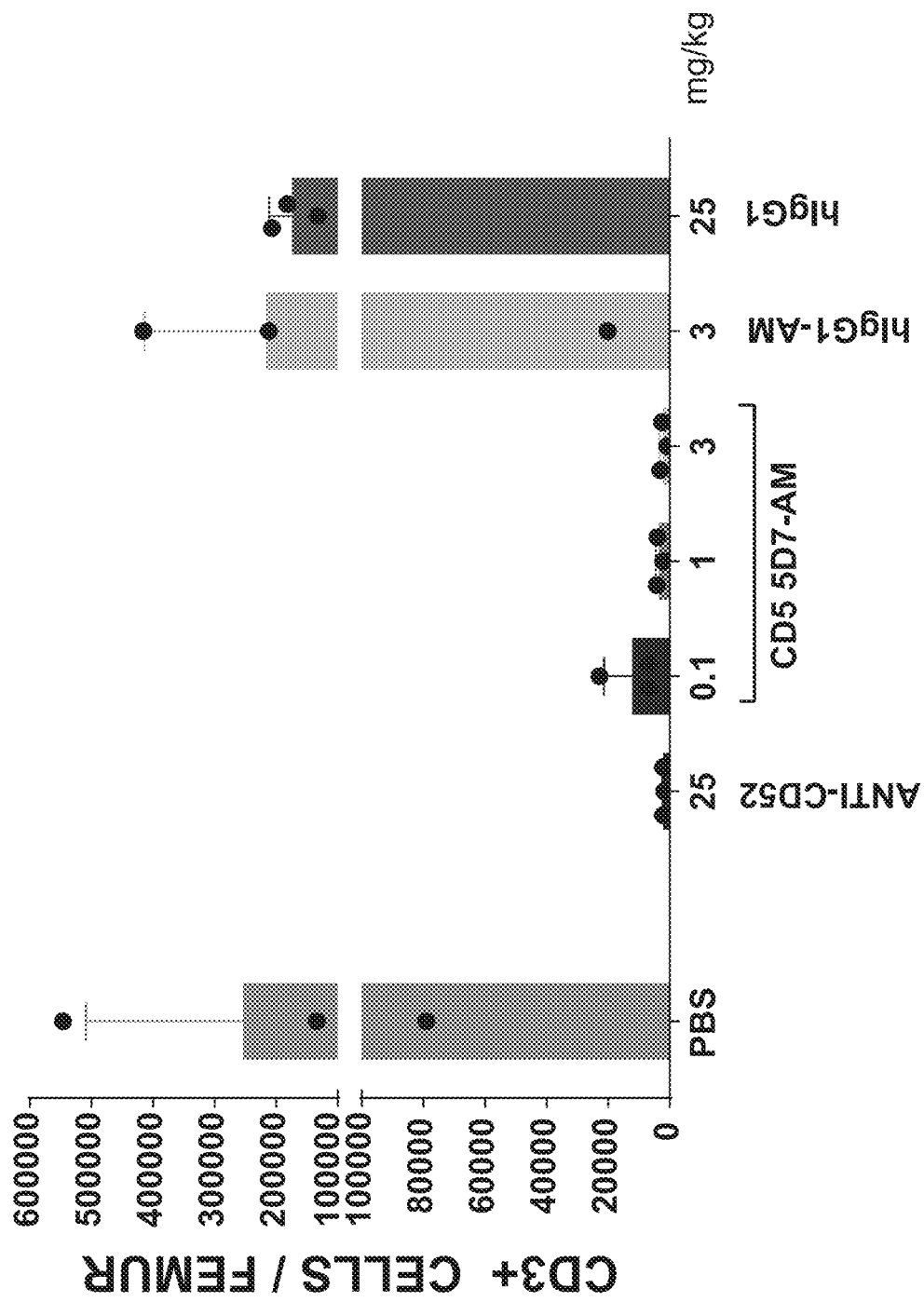

As shown in, FIGS. 4A-4B, humanized NSG mice treated with 0.3 mg/kg, 1 mg/kg, or 3 mg/kg DAR6 anti-CD5 5D7-ADCs exhibited potent T-cell depletion in peripheral blood or bone morrow while thymic T-cells were depleted following treatment with 1 mg/kg or 3 mg/kg of DAR6 anti-CD5 5D7-ADCs. Negative controls used in this in vivo experiment included a human IgG1 not specific to CD5 (as a naked antibody (huIgG1) and conjugated to an amatoxin (huIgG1-AM). As described in FIGS. 4A to 4B, the huIgG1 naked and conjugated controls had no impact on T cell depletion in peripheral blood (FIG. 4A) and bone marrow (FIG. 4B) as these controls were comparable to the PBS control. An anti-CD52 antibody (antibody YTH34.5) was used as a control as well, and was also able to deplete peripheral and bone marrow T cells at a dose of 25 mg/kg.

Figure 5A:
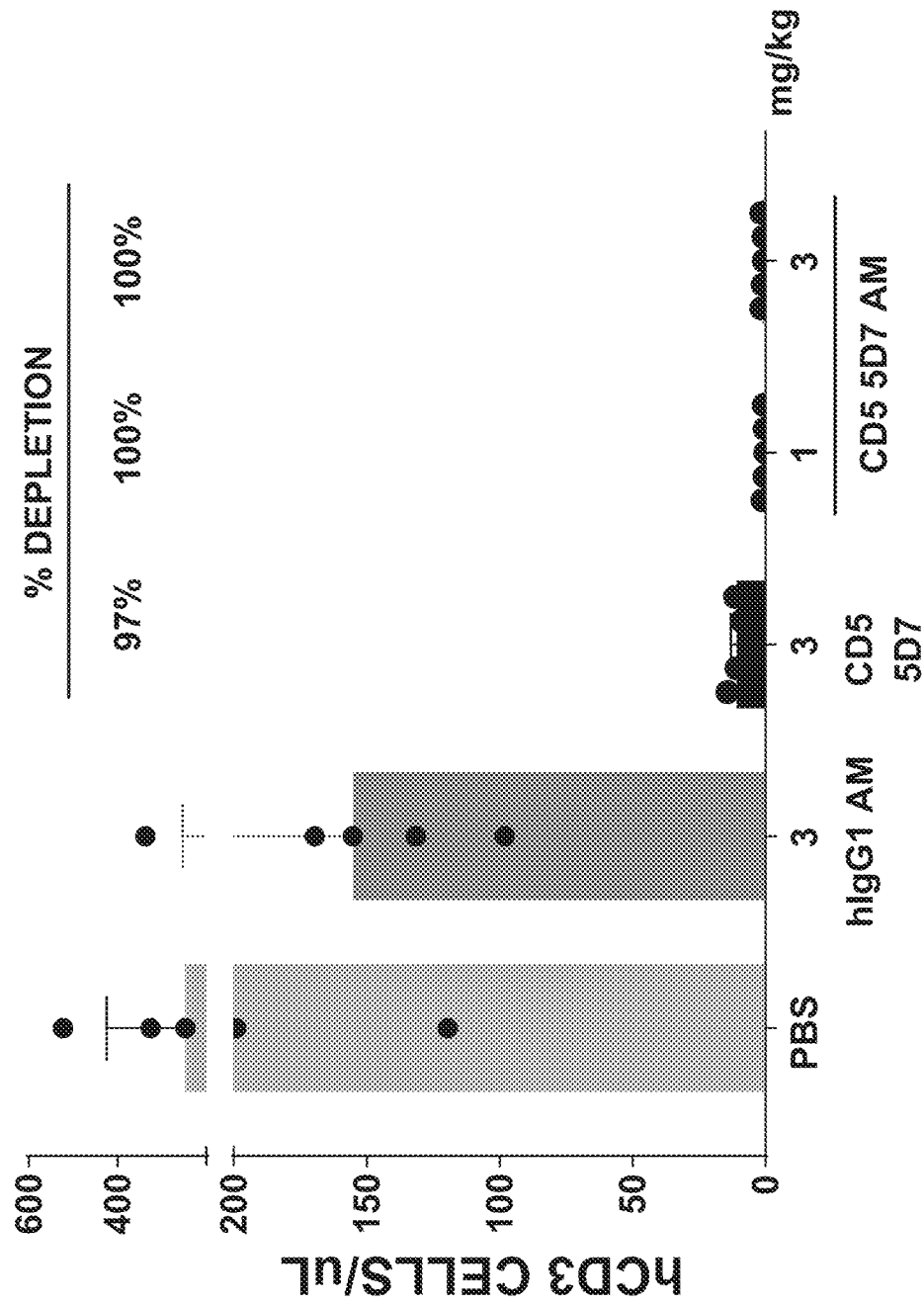
FIGS. 5A-5C graphically depict the results of an in vivo T-cell depletion assay showing the absolute levels of T-cells (CD3+ cells; y-axis) in the peripheral blood (FIG. 5A), bone marrow (FIG. 5B), and thymus (FIG. 5C) of humanized NSG mice 7 days after a single administration of 1 mg/kg or 3 mg/kg of an anti-CD5 5D7-amanitin ADC (i.e., 5D7-AM) having a site-specific DAR of 2. For comparison.
Figure 5B:
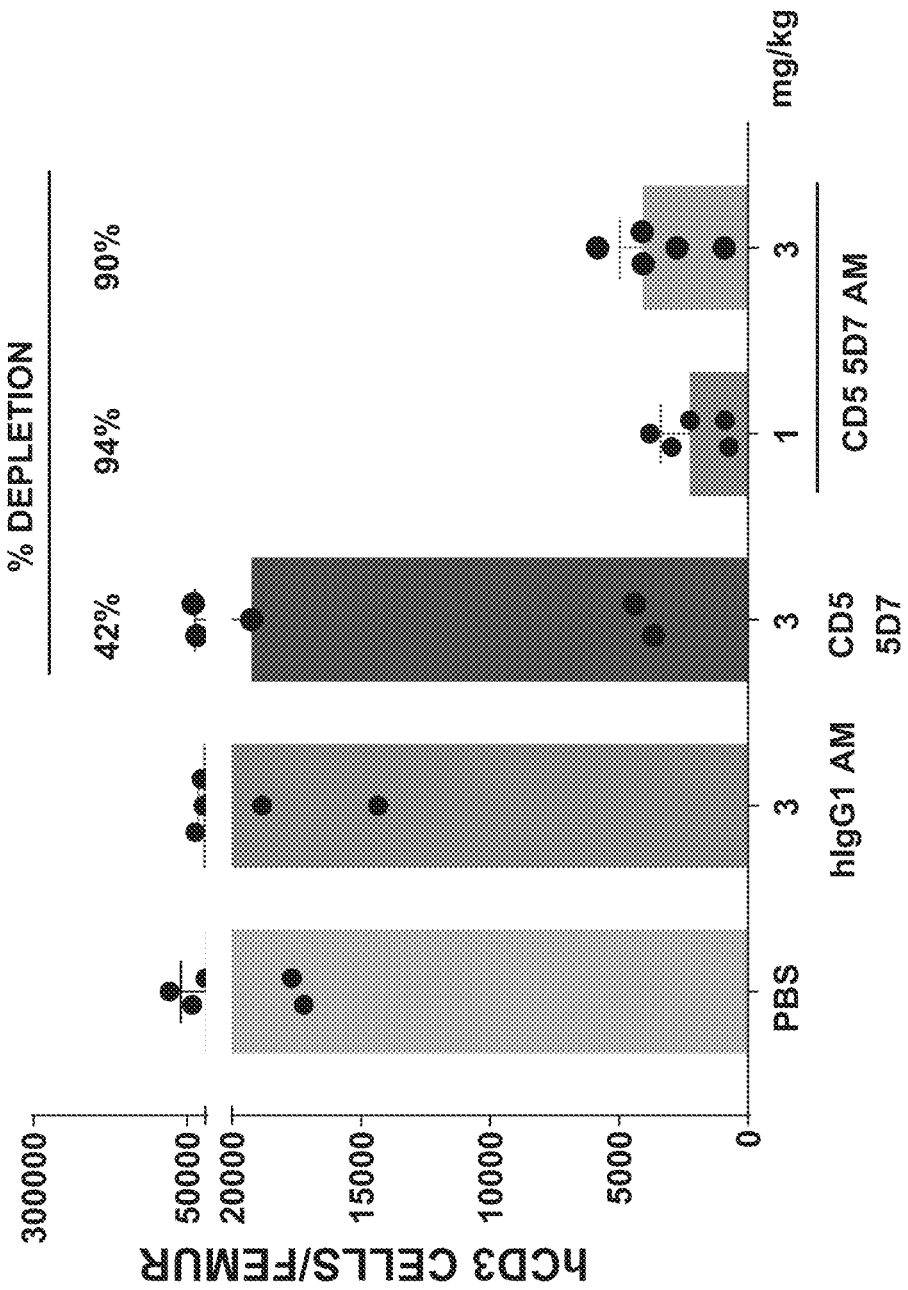
Figure 5C:
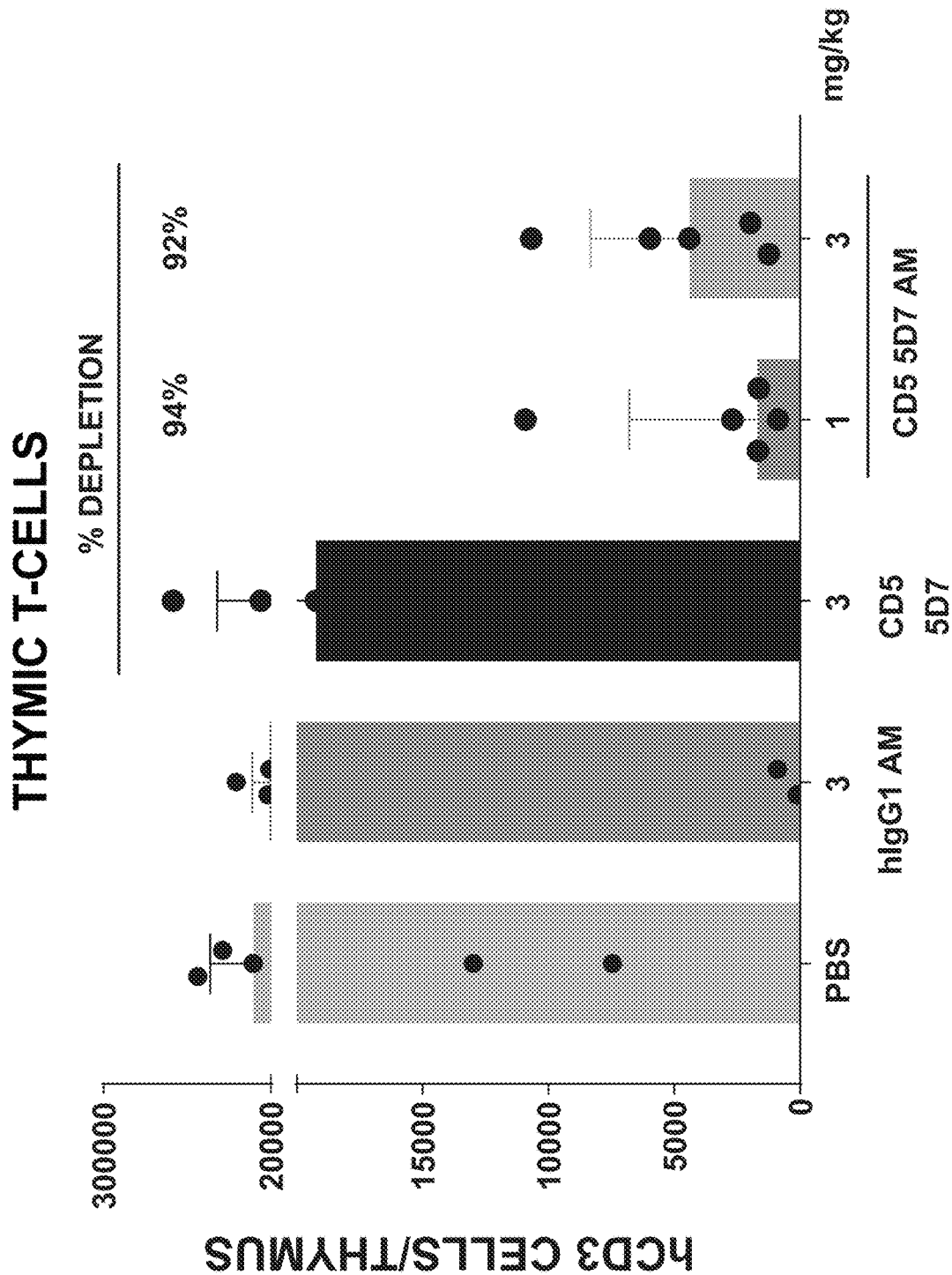

As shown in, FIGS. 5A-5C, humanized NSG mice treated with 1 mg/kg site or 3 mg/kg site-specific DAR2 anti-CD5 5D7-ADC exhibited potent T-cell depletion in peripheral blood, bone morrow, and thymic T-cells. In each of FIGS. 5A to 5C, naked antibody 5D7 was also used as a control. Antibody 5D7 was able to deplete peripheral T cells (relative to a non-specific human IgG1 control or PBS) as described in FIG. 5A, but was unable to deplete either marrow T cells or thymic T cells whereas the 5D7-AM ADC was effective at depleting both marrow and thymic as described in FIGS. 5B and 5C.

TABLE 4

Sequence Summary

| Sequence Identifier | Description | Sequence |
|---|---|---|
| SEQ ID NO: 1 | Light chain variable region | DIQMTQSPSSMSASLGDRVTITCRASQDINSYLS WFQQKPGKSPKTLIYRANRLVDGVPSRFSGSGS GTDYTLTISSLQYEDFGIYYCQQYDESPWITGGG TKLEIK |
| SEQ ID NO: 2 | Heavy chain variable region | QIQLVQSGPGLKKPGGSVRISCAASGYTFTNYGM NWVKQAPGKGLRWMGWINTHTGEPTYADDFKG RFTFSLDTSKSTAYLQINSLRAEDTATYFCTRRGY DWY FDVWGQGTTVTVSS |
| SEQ ID NO: 3 | CDR-H1 | GYTFTNY |
| SEQ ID NO: 4 | CDR-H2 | NTHTGE |
| SEQ ID NO: 5 | CDR-H3 | RGYDWYFDV |
| SEQ ID NO: 6 | CDR-L1 | RASQDINSYLS |
| SEQ ID NO: 7 | CDR-L2 | RANRLVD |
| SEQ ID NO: 8 | CDR-L3 | QQYDESPWT |

TABLE 4-continued

Sequence Summary

| Sequence Identifier | Description | Sequence |
|---|---|---|
| SEQ ID NO: 9 | Light chain variable region | DIQMTQSPSSLSASVGDRVTITCRASQDINSYLSWFQQKPGKAPKTLIYRANRLESGVPSRFSGSGSGTDYTLTISSLQYEDFGIYYCQQYDESPWTFGGGTKLEIK |
| SEQ ID NO: 10 | Heavy chain variable region | EIQLVQSGGGLVKPGGSVRISCAASGYTFTNYGMNWVRQAPGKGLEWMGWINTHYGEPTYADSFKGTRTFSLDDSKNTAYLQINSLRAEDTAVYFCTRRGYDWYFDVWGQGGTTVTVSS |
| SEQ ID NO: 11 | CDR-H1 | GYTFTNY |
| SEQ ID NO: 12 | CDR-H2 | NTHYGE |
| SEQ ID NO: 13 | CDR-H3 | RRGYDWYFDV |
| SEQ ID NO: 14 | CDR-L1 | RASQDINSYLS |
| SEQ ID NO: 15 | CDR-L2 | RANRLES |
| SEQ ID NO: 16 | CDR-L3 | QQYDESPWT |
| SEQ ID NO: 17 | CDR-H1 | GYSITSGYY |
| SEQ ID NO: 18 | CDR-H2 | ISYSGFT |
| SEQ ID NO: 19 | CDR-H3 | AGDRTGSWFAY |
| SEQ ID NO: 20 | CDR-L1 | QDISNY |
| SEQ ID NO: 21 | CDR-L2 | ATS |
| SEQ ID NO: 22 | CDR-L3 | LQYASYPFT |
| SEQ ID NO: 23 | CDR-H1 | GYIFTNYG |
| SEQ ID NO: 24 | CDR-H2 | INTYNGEP |
| SEQ ID NO: 25 | CDR-H3 | ARGDYYGYEDY |
| SEQ ID NO: 26 | CDR-L1 | QGISNY |
| SEQ ID NO: 27 | CDR-L2 | YTS |
| SEQ ID NO: 28 | CDR-L3 | QQYSKLPWT |
| SEQ ID NO: 29 | 5D7 CDR-H1 | FSLSTSGMG |
| SEQ ID NO: 30 | 5D7 CDR-H2 | WWDDD |
| SEQ ID NO: 31 | 5D7 CDR-H3 | RRATGTGFDY |
| SEQ ID NO: 32 | 5D7 CDR-L1 | QDVGTA |
| SEQ ID NO: 33 | 5D7 CDR-L2 | WTSTRHT |
| SEQ ID NO: 34 | 5D7 CDR-L3 | YNSYNT |
| SEQ ID NOs: 35-256 | | See Table 1 for summary of SEQ ID NOs: 35-256 |
| SEQ ID NO: 257 | Humanized 5D7 Heavy chain variable region (CDRs in bold) | QVTLKESGPVLVKPTETLTLTCTFSGFSLSTSGMGVGWIRQAPGKGLEWVAHIWWDDDVYYNPSLKSRLTITKDASKDQVSLKLSSVTAADTAVYYCVRRRATGTGFDYWGQGTLVTVSS |
| SEQ ID NO: 258 | Humanized 5D7 Light chain variable region (CDRs in bold) | NIVMTQSPSSLSASVGDRVTITCQASQDVGTAVAWYQQKPDQSPKLLIYWTSTRHTGVPDRFTGSGSGTDFTLTISSLQPEDIATYFCHQYNSYNTFGSGTKLEIK |

TABLE 4-continued

Sequence Summary

| Sequence Identifier | Description | Sequence |
|---|---|---|
| SEQ ID NO: 259 | Consensus human Heavy chain variable domain (CDRs in bold) | EVQLVESGGGLVQPGGSLRLSCAASGFTFSDYA MSWVRQAPGKGLEWVAVISENGSDTYYADSVKG RFTISRDDSKNTLYLQMNSLRAEDTAVYYCARDR GGAVSYFDVWGQGTLVTVSS |
| SEQ ID NO: 260 | Consensus human Light chain variable domain (CDRs in bold) | DIQMTQSFSSLSASVGDRVTITCRASQDVSSYLA WYQQKPGKAPKLLIYAASSLESGVPSRFSGSGS GTDFTLTISSLQPEDFATYYCQQYNSLPYTFGQG TKVEIKRT |
| SEQ ID NO: 261 | Human CD5 amino acid sequence | MVCSQSWGRS SKQWEDPSQA SKVCQRLNCG VPLSLGPFLV TYTPQSSIIC YGQLGSFSNCSHSRNDMCHS LGLTCLEPQK TTPPTTRPPP TTTPEPTAPP RLQLVAQSGG QHCAGVVEFYSGSLGGTISY EAQDKTQDLE NFLCNNLQCG SFLKHLPETE AGRAQDPGEP REHQPLPIQWKIQNSSCTSL EHCFRKIKPQ KSGRVLALLC SGFQPKVQSR LVGGSSICEG TVEVRQGAQWAALCDSSSAR SSLRWEEVCR EQQCGSVNSY RVLDAGDPTS RGLFCPHQKL SQCHELWERNSYCKKVFVTC QDPNPAGLAA GTVASIILAL VLLVVLLVVC GPLAYKKLVK KFRQKKQRQWIGPTGMNQNM SFHRNHTATV RSHAENPTAS HVDNEYSQPP RNSHLSAYPA LEGALHRSSMQPDNSSDSDY DLHGAQRL |

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method of depleting a population of CD5+ cells in a human patient, the method comprising:
    administering to the human patient an effective amount of an anti-CD5 antibody 5D7 or antigen-binding fragment thereof,
    wherein the antibody, or antigen-binding fragment thereof, is conjugated to a cytotoxin, to form an anti-CD5 antibody 5D7 antibody drug conjugate,
    wherein the cytotoxin is an amatoxin,
    wherein the anti-CD5 antibody 5D7 antibody drug conjugate has a drug to antibody ratio of about 6 or 2, wherein the conjugation is site-specific via a D265C mutation, and
    wherein the antibody or antigen-binding fragment thereof conjugated to a cytotoxin is represented by the formula Ab-Z-L-Am, wherein Ab is the antibody or antigen-binding fragment thereof, L is a linker, Z is a chemical moiety, and Am is an amatoxin represented by formula (I)

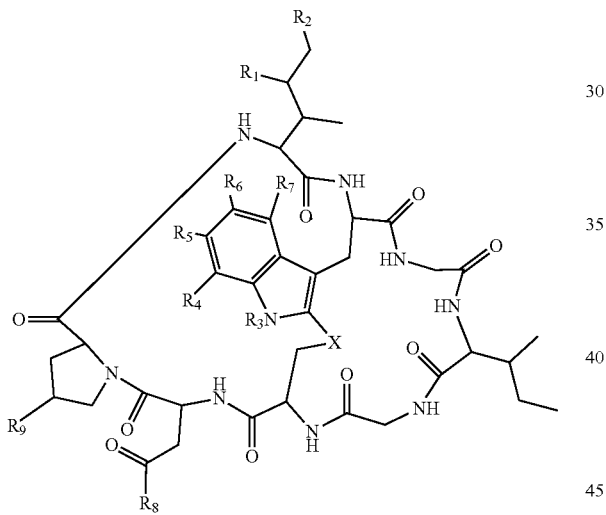

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl;
L is $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, cycloalkylene, heterocycloalkylene, arylene, heteroarylene; a dipeptide, —C(=O)—, a peptide, or a combination thereof; and Z is a chemical moiety formed from a coupling reaction between a reactive substituent present on L and a reactive substituent present within the antibody or antigen-binding fragment thereof, wherein Am comprises exactly one $R_C$ substituent, and wherein said antibody or antigen-binding fragment thereof comprises the following complementarity determining regions (CDRs):
    a. a CDR-H1 having the amino acid sequence GYTFTNY (SEQ ID NO: 3);
    b. a CDR-H2 having the amino acid sequence NTHTGE (SEQ ID NO: 4);
    c. a CDR-H3 having the amino acid sequence RGYDWYFDV (SEQ ID NO: 5);
    d. a CDR-L1 having the amino acid sequence RASQDINSYLS (SEQ ID NO: 6);
    e. a CDR-L2 having the amino acid sequence RANRLVD (SEQ ID NO: 7); and
    f. a CDR-L3 having the amino acid sequence QQYDESPWT (SEQ ID NO: 8); or
    a. a CDR-H1 having the amino acid sequence FSLSTSGMG (SEQ ID NO: 29);
    b. a CDR-H2 having the amino acid sequence WWDDD (SEQ ID NO: 30);
    c. a CDR-H3 having the amino acid sequence RRATGTGFDY (SEQ ID NO: 31);
    d. a CDR-L1 having the amino acid sequence QDVGTA (SEQ ID NO: 32);
    e. a CDR-L2 having the amino acid sequence WTSTRHT (SEQ ID NO: 33);
    f. a CDR-L3 having the amino acid sequence YNSYNT (SEQ ID NO: 34).

2. A method of preventing rejection of a hematopoietic stem cell graft in a human patient in need of a hematopoietic stem cell transplant, the method comprising:
    administering to the human patient an effective amount of an anti-CD5 antibody 5D7, or antigen-binding fragment thereof, prior to the human patient receiving a transplant comprising hematopoietic stem cells,
    wherein the antibody, or antigen-binding fragment thereof, is conjugated to a cytotoxin, to form an anti-CD5 antibody 5D7 antibody drug conjugate,
    wherein the cytotoxin is an amatoxin, and
    wherein the anti-CD5 antibody 5D7 antibody drug conjugate has a drug to antibody ratio of about 6 or 2, wherein the conjugation is site-specific via a D265C mutation, and
    wherein the antibody or antigen-binding fragment thereof conjugated to a cytotoxin is represented by the formula Ab-Z-L-Am, wherein Ab is the antibody or antigen-binding fragment thereof, L is a linker, Z is a chemical moiety, and Am is an amatoxin represented by formula (I)

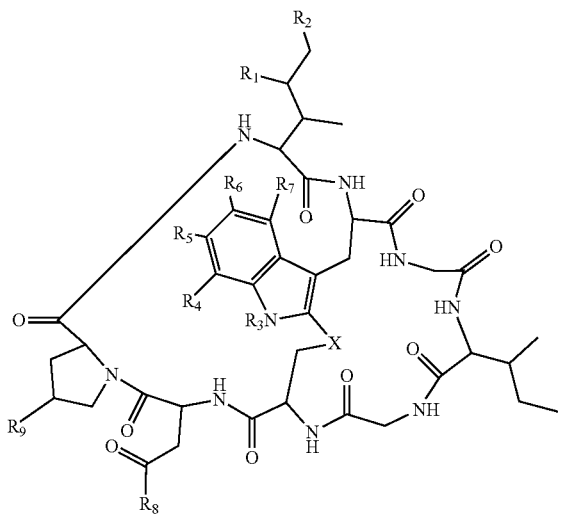

(I)

wherein R₁ is H, OH, OR$_A$, or OR$_C$;
R₂ is H, OH, OR$_B$, or OR$_C$;
R$_A$ and R$_B$, when present, together with the oxygen atoms to which they are bound, combine to form an 5-membered heterocycloalkyl group;
R₃ is H, R$_C$, or R$_D$;
R₄, R₅, R₆, and R₇ are each independently H, OH, OR$_C$, OR$_D$, R$_C$, or R$_D$;
R₈ is OH, NH₂, OR$_C$, OR$_D$, NHR$_C$, or NR$_C$R$_D$;
R₉ is H, OH, OR$_C$, or OR$_D$;
X is —S—, —S(O)—, or —SO₂—;
R$_C$ is -L-Z;
R$_D$ is C₁-C₆ alkyl, C₁-C₆ heteroalkyl, C₂-C₆ alkenyl, C₂-C₆ heteroalkenyl, C₂-C₆ alkynyl, C₂-C₆ heteroalkynyl, cycloalkyl, heterocycloalkyl, aryl, or heteroaryl;
L is C₁-C₆ alkylene, C₁-C₆ heteroalkylene, C₂-C₆ alkenylene, C₂-C₆ heteroalkenylene, C₂-C₆ alkynylene, C₂-C₆ heteroalkynylene, cycloalkylene, heterocycloalkylene, arylene, heteroarylene; a dipeptide, —C(=O)—, a peptide, or a combination thereof; and
Z is a chemical moiety formed from a coupling reaction between a reactive substituent present on L and a reactive substituent present within the antibody or antigen-binding fragment thereof,
wherein Am comprises exactly one R$_C$ substituent, and wherein said antibody or antigen-binding fragment thereof comprises the following complementarity determining regions (CDRs):
 a. a CDR-H1 having the amino acid sequence GYTFTNY (SEQ ID NO: 3);
 b. a CDR-H2 having the amino acid sequence NTHTGE (SEQ ID NO: 4);
 c. a CDR-H3 having the amino acid sequence RGYDWYFDV (SEQ ID NO: 5);
 d. a CDR-L1 having the amino acid sequence RASQDINSYLS (SEQ ID NO: 6);
 e. a CDR-L2 having the amino acid sequence RANRLVD (SEQ ID NO: 7); and
 f. a CDR-L3 having the amino acid sequence QQYDESPWT (SEQ ID NO: 8); or
 a. a CDR-H1 having the amino acid sequence FSLSTSGMG (SEQ ID NO: 29);
 b. a CDR-H2 having the amino acid sequence WWDDD (SEQ ID NO: 30);
 c. a CDR-H3 having the amino acid sequence RRATGTGFDY (SEQ ID NO: 31);
 d. a CDR-L1 having the amino acid sequence QDVGTA (SEQ ID NO: 32);
 e. a CDR-L2 having the amino acid sequence WTSTRHT (SEQ ID NO: 33);
 f. a CDR-L3 having the amino acid sequence YNSYNT (SEQ ID NO: 34).

3. The method of claim 1, comprising administering a transplant comprising hematopoietic stem cells to the human patient.

4. The method of claim 1, wherein the antibody or antigen-binding fragment thereof,
comprises a V$_L$ having the amino acid sequence DIQMTQSPSSMSASLGDRVTITCRASQDINSYLSWFQQKPGKSPKTLIYRANRL VDGVPSRFSGSGSGTDYTLTISSLQYEDFGIYYCQQYDESPWTFGGGTKLEIK (SEQ ID NO: 1); and a V$_H$ having the amino acid sequence QIQLVQSGPGLKKPGGSVRISCAASGYTFTNYGMNWVKQAPGKGLRWMGWI NTHTGEPTYADDFKGRFTFSLDTSKSTAYLQINSLRAEDTATYFCTRRGYDWYFDVWGQGTTVTVSS (SEQ ID NO: 2); or
comprises a V$_L$ having the amino acid sequence NIVMTQSPSSLSASVGDRVTITCQASQDVGTAVAWYQQKPDQSPKLLIYWTSTRHTGVP DRFTGSGS GTDFTLTISSLQPEDIATYFCHQYNSYNTFGSGTKLEIK (SEQ ID NO: 258); and a V$_H$ having the amino acid sequence QVTLKESGPVLVKPTETLTLTCTFSGFSLSTSGMGVGWIRQAPGKGLEWVAHIWWDDDVYYNPSLKSRLTITKDASKDQVSLKLSSVTAADTAVYYCVRRRATGTGFDYWGQGTLV TVSS (SEQ ID NO: 257).

5. The method of claim 1, wherein R$_A$ and R$_B$, together with the oxygen atoms to which they are bound, combine to form a 5 membered heterocycloalkyl group of formula:

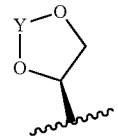

wherein Y is —C(=O)—, —C(=S)—, —C(=NR$_E$)—, or —C(R$_E$R$_{E'}$)—; and
R$_E$ and R$_{E'}$ are each independently C₁-C₆ alkylene-R$_C$, C₁-C₆ heteroalkylene-R$_C$, C₂-C₆ alkenylene-R$_C$, C₂-C₆ heteroalkenylene-R$_C$, C₂-C₆ alkynylene-R$_C$, C₂-C₆ heteroalkynylene-R$_C$, cycloalkylene-R$_C$, heterocycloalkylene-R$_C$, arylene-R$_C$, or heteroarylene-R$_C$.

6. The method of claim 1, wherein:
(a) R₁ is H, OH, or OR$_A$;
R₂ is H, OH, or OR$_B$;
R$_A$ and R$_B$, together with the oxygen atoms to which they are bound, combine to form:

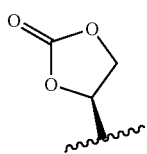 [SMILES: *[C@@H]1COC(=O)O1]

$R_3$, $R_4$, $R_6$, and $R_7$ are each H;
$R_5$ is $OR_C$;
$R_8$ is OH or $NH_2$; and
$R_9$ is H or OH;
(b) R and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$; and
$R_9$ is H or OH;
(c) $R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$; and
$R_9$ is H or OH;
or
(d) $R_1$ and $R_2$ are each independently H or OH;
$R_3$, $R_6$, and $R_7$ are each H;
$R_4$ and $R_5$ are each independently H or OH;
$R_8$ is $OR_C$ or $NHR_C$; and
$R_9$ is H or OH.

7. The method of claim 1, wherein the antibody or antigen-binding fragment thereof conjugated to a cytotoxin is represented by the formula Ab-L-Z-Am, wherein Ab is the antibody or antigen-binding fragment thereof, Z is a chemical moiety, L is a linker, and Am is an amatoxin, and the amatoxin-linker conjugate Am-L-Z is represented by formula (IIB)

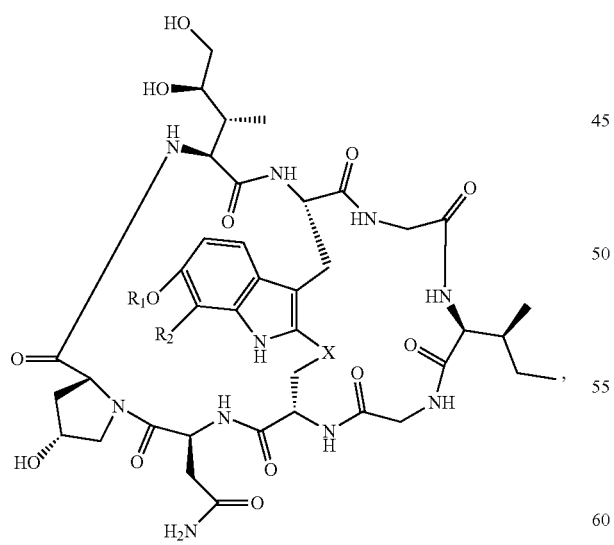

wherein X is S, SO, or $SO_2$;
$R_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and $R_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof;
wherein when $R_1$ is H, $R_2$ is the linker, and when $R_2$ is H, $R_1$ is the linker.

8. The method of claim 2, wherein the hematopoietic stem cells or progeny thereof are capable of localizing to hematopoietic tissue and/or reestablishing hematopoiesis following transplantation of the hematopoietic stem cells into the patient.

9. The method of claim 7, wherein the linker includes a —$(CH_2)_n$— unit, wherein n is an integer from 2-6, or wherein the linker includes a dipeptide selected from Val-Ala and Val-Cit.

10. The method of claim 7, wherein Am-L-Z-Ab is one of:

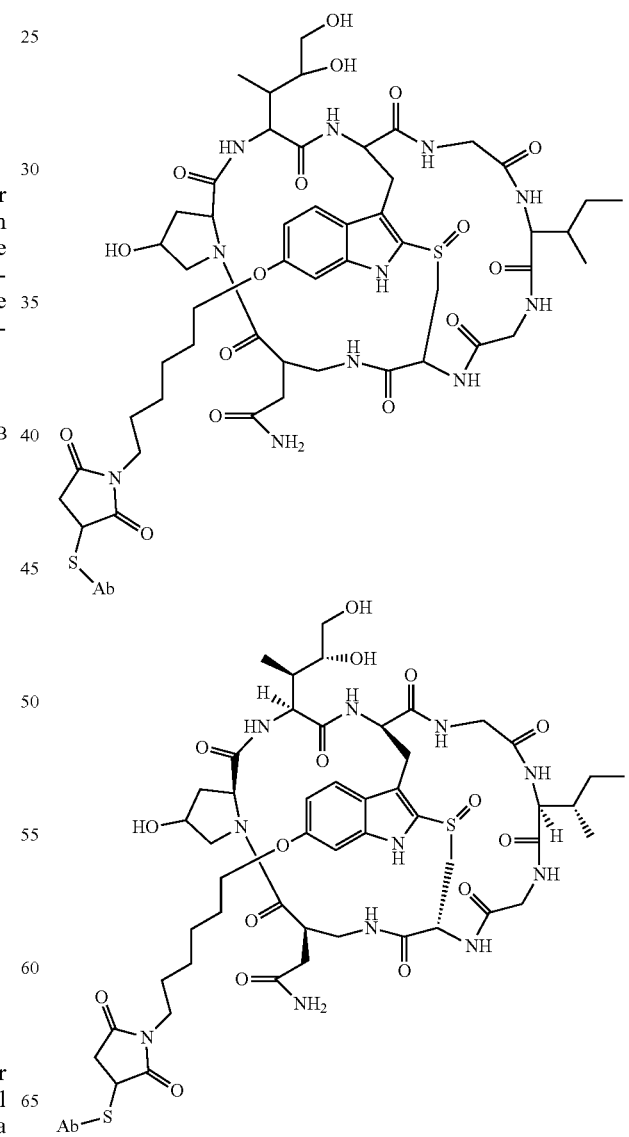

-continued

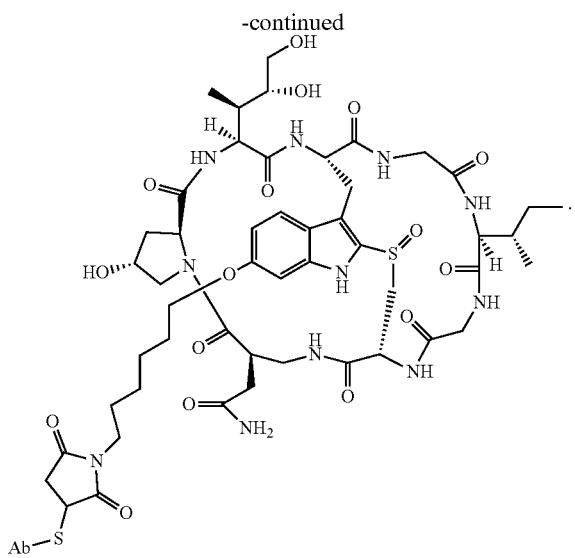

11. The method of claim 3, wherein the antibody or antigen-binding fragment thereof,
comprises a $V_L$ having the amino acid sequence DIQMTQSPSSMSASLGDRVTITCRASQDIN-SYLSWFQQKPGKSPKTLIYRANRL VDGVPSR-FSGSGSGTDYTLTISSLQYEDFGIYYCQQYDESP-WTFGGGTKLEIK (SEQ ID NO: 1); and a $V_H$ having the amino acid sequence QIQLVQSGP-GLKKPGGSVRISCAASGYTFTNYGMNWVKQA-PGKGLRWMGWI NTHTGEPTYADDFKGRFTFS-LDTSKSTAYLQINSLRAEDTATYFCTRRGYDWY FDVWGQGTTVTVSS (SEQ ID NO: 2); or
comprises a $V_L$ having the amino acid sequence NIVMTQSPSSLSASVGDRVTITCQASQDVGTA-VAWYQQKPDQSPKLLIYWTSTRHTGVP DRFTGSGS GTDFTLTISSLQPEDIATYFCHQYN-SYNTFGSGTKLEIK (SEQ ID NO: 258); and a $V_H$ having the amino acid sequence QVTL-KESGPVLVKPTETLTLTCTFSGFSLST-SGMGVGWIRQAPGKGLEWVAHIWWDDD VYYNPSLKSRLTITKDASKDQVSLKLSSVTAAD-TAVYYCVRRRATGTGFDYWGQGTLV TVSS (SEQ ID NO: 257).

12. The method of claim 2, wherein $R_A$ and $R_B$, together with the oxygen atoms to which they are bound, combine to form a 5 membered heterocycloalkyl group of formula:

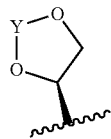

wherein Y is —C(═O)—, —C(═S)—, —C(═NR$_E$)—, or —C(R$_E$R$_{E'}$)—; and
R$_E$ and R$_{E'}$ are each independently C$_1$-C$_6$ alkylene-R$_C$, C$_1$-C$_6$ heteroalkylene-R$_C$, C$_2$-C$_6$ alkenylene-R$_C$, C$_2$-C$_6$ heteroalkenylene-R$_C$, C$_2$-C$_6$ alkynylene-R$_C$, C$_2$-C$_6$ heteroalkynylene-R$_C$, cycloalkylene-R$_C$, heterocycloalkylene-R$_C$, arylene-R$_C$, or heteroarylene-R$_C$.

13. The method of claim 2, wherein the antibody or antigen-binding fragment thereof conjugated to a cytotoxin is represented by the formula Ab-L-Z-Am, wherein Ab is the antibody or antigen-binding fragment thereof, Z is a chemical moiety, L is a linker, and Am is an amatoxin, and the amatoxin-linker conjugate Am-L-Z is represented by formula (IIB)

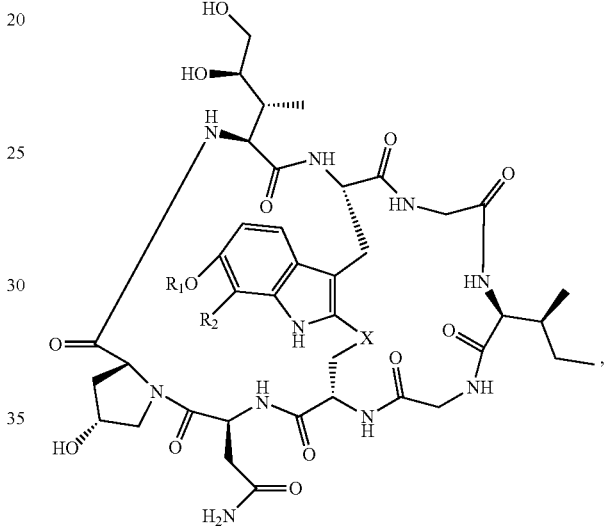

IIB wherein X is S, SO, or SO$_2$;
R$_1$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof; and
R$_2$ is H or a linker covalently bound to the antibody or antigen-binding fragment thereof through a chemical moiety Z, formed from a coupling reaction between a reactive substituent present on the linker and a reactive substituent present within an antibody, or antigen-binding fragment thereof;
wherein when R$_1$ is H, R$_2$ is the linker, and when R$_2$ is H, R$_1$ is the linker.

* * * * *

SEQUENCE LISTING

```
<160> NUMBER OF SEQ ID NOS: 261

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Met Ser Ala Ser Leu Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95
```

```
Thr Phe Gly Gly Gly Thr Lys Leu Glu Ile Lys
            100                 105

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ile Gln Leu Val Gln Ser Gly Pro Gly Leu Lys Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Lys Gln Ala Pro Gly Lys Gly Leu Arg Trp Met
        35                  40                  45

Gly Trp Ile Asn Thr His Thr Gly Glu Pro Thr Tyr Ala Asp Asp Phe
    50                  55                  60

Lys Gly Arg Phe Thr Phe Ser Leu Asp Thr Ser Lys Ser Thr Ala Tyr
65                  70                  75                  80

Leu Gln Ile Asn Ser Leu Arg Ala Glu Asp Thr Ala Thr Tyr Phe Cys
                85                  90                  95

Thr Arg Arg Gly Tyr Asp Trp Tyr Phe Asp Val Trp Gly Gln Gly Thr
            100                 105                 110

Thr Val Thr Val Ser Ser
        115

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Thr Phe Thr Asn Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Thr His Thr Gly Glu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gly Tyr Asp Trp Tyr Phe Asp Val
1               5
```

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Asp Ile Asn Ser Tyr Leu Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Asn Arg Leu Val Asp
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Asp Glu Ser Pro Trp Thr
1               5

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105

<210> SEQ ID NO 10
<211> LENGTH: 119
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Tyr Gly Glu Pro Thr Tyr Ala Asp Ser Phe
    50                  55                  60

Lys Gly Thr Arg Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Gly
            100                 105                 110

Thr Thr Val Thr Val Ser Ser
        115

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Tyr Thr Phe Thr Asn Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Thr His Tyr Gly Glu
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Gly Tyr Asp Trp Tyr Phe Asp Val
1               5                   10

<210> SEQ ID NO 14
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 14

Arg Ala Ser Gln Asp Ile Asn Ser Tyr Leu Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Asn Arg Leu Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Tyr Asp Glu Ser Pro Trp Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Tyr Ser Ile Thr Ser Gly Tyr Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Ser Tyr Ser Gly Phe Thr
1               5

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gly Asp Arg Thr Gly Ser Trp Phe Ala Tyr
1               5                   10
```

```
<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Asp Ile Ser Asn Tyr
1               5

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Thr Ser
1

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gln Tyr Ala Ser Tyr Pro Phe Thr
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Ile Phe Thr Asn Tyr Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Asn Thr Tyr Asn Gly Glu Pro
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25
```

```
Ala Arg Gly Asp Tyr Tyr Gly Tyr Glu Asp Tyr
1               5                   10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gly Ile Ser Asn Tyr
1               5

<210> SEQ ID NO 27
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Thr Ser
1

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gln Tyr Ser Lys Leu Pro Trp Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Ser Leu Ser Thr Ser Gly Met Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Trp Asp Asp Asp
1               5

<210> SEQ ID NO 31
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 31

Arg Arg Ala Thr Gly Thr Gly Phe Asp Tyr
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Asp Val Gly Thr Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Thr Ser Thr Arg His Thr
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Tyr Asn Ser Tyr Asn Thr
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Gly Tyr Ser Phe Thr Gly Tyr Thr Met
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Ile Asn Pro Tyr Asn Gly Gly Thr Thr
1               5                   10
```

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Ala Arg Asp Tyr Tyr Gly Ser Ser Pro Asp Phe Asp Tyr Trp
1               5                   10                  15

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Gly Tyr Ser Phe Thr Asp Tyr Thr Met
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Ile Asn Pro Tyr Asn Gly Gly Thr Met
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Ala Arg Asp Asn Tyr Gly Ser Ser Pro Asp Phe Asp Tyr Trp
1               5                   10                  15

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Gly Tyr Ser Phe Thr Gly Tyr Thr Met
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 42

Leu Ile Asn Pro Tyr Asn Gly Gly Thr Met
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Ala Arg Asp Asn Tyr Gly Ser Ser Pro Tyr Phe Asp Tyr Trp
1               5                   10                  15

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Gly Tyr Ser Phe Thr Gly Tyr Thr Met
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Ile Asn Pro Tyr Asn Gly Gly Thr Met
1               5                   10

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Ala Arg Asp Asn Tyr Gly Ser Ser Pro Tyr Phe Asp Tyr Trp
1               5                   10                  15

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gly Tyr Ser Phe Thr Gly Tyr Thr Met
1               5                   10

<210> SEQ ID NO 48
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 48

Leu Ile Asn Pro Tyr Asn Gly Gly Thr Thr
1               5                   10

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Ala Arg Asp Tyr Tyr Gly Ser Ser Pro Asp Phe Asp Tyr Trp
1               5                   10                  15

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Gly Phe Thr Phe Ser Asn Tyr Ala Met
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Ile Ser Ser Gly Gly Asn Thr Phe
1               5

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Val Arg Tyr Tyr Tyr Gly Val Thr Tyr Trp Tyr Phe Asp Val Trp
1               5                   10                  15

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Gly Phe Thr Phe Ser Ser Tyr Ala Met
1               5                   10
```

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Ile Ser Ser Gly Gly Ser Thr Tyr
1               5

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Val Arg Tyr Tyr Tyr Gly Ile Arg Tyr Trp Tyr Phe Asp Val Trp
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Gly Tyr Ser Phe Thr Ala Tyr Asn Ile
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Ile Asp Pro Tyr Tyr Gly Asp Thr Lys
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys Ala Arg Arg Met Ile Thr Met Gly Asp Trp Tyr Phe Asp Val Trp
1               5                   10                  15

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 59

Ser Gly Tyr Ser Phe Thr Ala Tyr Ser Met
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ser Ile Asp Pro Tyr Tyr Gly Asp Thr Lys
1               5                   10

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Ala Arg Arg Met Ile Thr Thr Gly Asp Trp Tyr Phe Asp Val Trp
1               5                   10                  15

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Gly Tyr Thr Phe Thr Asn Phe Ala Ile
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ile Ser Ser Asn Ser Gly Asp Val Ser
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Ala Arg His Tyr Gly Ala His Asn Tyr Phe Asp Tyr Trp
1               5                   10

<210> SEQ ID NO 65
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Gly Tyr Thr Phe Thr Asn Phe Ala Ile
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Ile Ser Thr Ser Ser Gly Asp Val Ser
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Ala Arg His Tyr Gly Ala Asn Asn Tyr Phe Asp Tyr Trp
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Gly Tyr Thr Phe Thr Asn Phe Ala Ile
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ile Ser Ser Asn Ser Gly Asp Val Ser
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Ala Arg His Tyr Gly Ala His Asn Tyr Phe Asp Tyr Trp
```

```
1               5                  10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Gly Tyr Thr Phe Thr Asn Phe Ala Ile
1               5                  10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Ile Ser Ser Asn Ser Gly Asp Val Ser
1               5                  10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Ala Arg His Tyr Gly Ala His Asn Tyr Phe Asp Tyr Trp
1               5                  10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Gly Phe Asn Ile Lys Asp Thr Tyr Met
1               5                  10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ile Asp Pro Ala Asn Gly Asn Thr Lys
1               5                  10

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 76

Cys Ala Arg Glu Glu Asn Tyr Tyr Gly Thr Tyr Tyr Phe Asp Tyr Trp
1               5                   10                  15

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Gly Tyr Ser Phe Thr Ser Tyr Trp Met
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Ile His Pro Ser Asp Ser Glu Thr Arg
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Cys Ala Arg Trp Gly Asp His Asp Asp Ala Met Asp Phe Trp
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Gly Phe Ser Leu Thr Asn Tyr Asp Val
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Ile Trp Ser Gly Gly Asn Thr Asp
1               5

<210> SEQ ID NO 82

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Cys Ala Arg Asn His Gly Asp Gly Tyr Phe Asn Trp Tyr Phe Asp Val
1               5                   10                  15

Trp

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ser Gly Phe Ser Leu Thr Asn Tyr Asp Val
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Val Ile Trp Ser Gly Gly Asn Thr Asp
1               5

<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Cys Ala Arg Asn His Gly Asp Gly Tyr Tyr Asn Trp Tyr Phe Asp Val
1               5                   10                  15

Trp

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Gly Phe Thr Phe Ser Asn Tyr Gly Met
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Ala Ile Asn Ser Asn Gly Asp Ile Thr Tyr
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Cys Ala Arg Gly Thr Ala Trp Phe Thr Tyr Trp
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ser Gly Tyr Ser Phe Thr Gly Tyr Thr Met
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Ile Asn Pro Tyr Asn Gly Gly Thr Arg
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Cys Ala Arg Asp Gly Asp Asp Gly Trp Asp Ile Asp Val Trp
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ser Gly Tyr Ile Phe Ala Asn Tyr Gly Met
1               5                   10

<210> SEQ ID NO 93

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Trp Ile Asn Thr Tyr Thr Gly Glu Pro Thr
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Cys Ala Arg Arg Gly Thr Tyr Trp His Phe Asp Val Trp
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Gly Tyr Asn Phe Thr Asn Tyr Gly Met
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Trp Ile Asn Thr Tyr Thr Gly Glu Pro Thr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Ala Arg Arg Gly Ser Tyr Trp His Phe Asp Val Trp
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98
```

Ser Gly Tyr Thr Phe Thr Asn Tyr Gly Met
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Trp Ile Asn Thr Tyr Thr Gly Glu Pro Thr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Cys Ala Arg Arg Ser Thr Leu Val Phe Asp Tyr Trp
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Gly Tyr Thr Phe Thr Asp Tyr Tyr Ile
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Trp Ile Tyr Pro Gly Gly Gly Asn Thr Arg
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Cys Ala Arg Asn Gly Tyr Trp Tyr Phe Asp Val Trp
1               5                   10

<210> SEQ ID NO 104
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 104

Ser Gly Tyr Thr Phe Thr Asp Tyr Tyr Ile
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Trp Ile Tyr Pro Gly Gly Gly Asn Thr Arg
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Cys Ala Arg Asn Gly Tyr Trp Tyr Phe Asp Val Trp
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Gly Asn Thr Phe Thr Asn Phe Tyr Leu
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Cys Ile Tyr Pro Gly Asn Val Lys Thr Lys
1               5                   10

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Cys Ala Lys Glu Gly Asp Tyr Asp Gly Thr Ala Tyr Phe Asp Tyr Trp
1               5                   10                  15
```

```
<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ser Gly Tyr Thr Phe Thr Asn Tyr Gly Met
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Trp Ile Asn Thr Tyr Thr Gly Glu Pro Thr
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Ala Arg Arg Arg Asp Gly Asn Phe Asp Tyr Trp
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser Glu Phe Thr Phe Ser Asn Tyr Ala Met
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Ile Ser Ser Gly Gly Ser Tyr Thr Tyr
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115
```

Cys Val Arg His Gly Tyr Phe Asp Val Trp
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Gly Tyr Thr Phe Thr Ser Tyr Arg Met
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ile Asp Pro Tyr Asp Ser Gly Thr His
1               5                   10

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Cys Ala Phe Tyr Asp Gly Ala Tyr Trp
1               5

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Gly Phe Asn Ile Lys Asp Thr Tyr Met
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Ile Asp Pro Ala Asn Gly Asn Thr Lys
1               5                   10

<210> SEQ ID NO 121
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 121

Cys Ala Ser Tyr Asp Pro Asp Tyr Trp
1               5

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Gly Tyr Ser Phe Thr Asp Tyr Thr Met
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Leu Ile Asn Pro Tyr Asn Gly Gly Thr Arg
1               5                   10

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Ala Arg Asp Thr Thr Ala Thr Tyr Tyr Phe Asp Tyr Trp
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Gly Tyr Met Phe Thr Asn His Gly Met
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Trp Ile Asn Thr Tyr Thr Gly Glu Pro Thr
1               5                   10
```

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Cys Ala Arg Arg Val Ala Thr Tyr Phe Asp Val Trp
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ser Gly Tyr Met Phe Thr Asn Tyr Gly Met
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Trp Ile Asn Thr Tyr Thr Gly Glu Pro Thr
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Cys Thr Arg Arg Ser His Ile Thr Leu Asp Tyr Trp
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Gly Tyr Ile Phe Thr Asn Tyr Gly Met
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 132

Trp Ile Asn Thr Tyr Thr Gly Glu Pro Thr
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Ala Arg Arg Arg Thr Thr Ala Phe Asp Tyr Trp
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Gly Phe Asn Ile Lys Asp Tyr Tyr Ile
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Trp Ile Asp Pro Glu Asn Gly Arg Thr Glu
1               5                   10

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Asn Asn Gly Asn Tyr Val Arg His Tyr Tyr Phe Asp Tyr Trp
1               5                   10                  15

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Gly Tyr Thr Phe Ile Asn Tyr Gly Met
1               5                   10

<210> SEQ ID NO 138
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 138

Trp Ile Asn Thr Tyr Thr Gly Glu Pro Thr
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Cys Thr Arg Arg Arg Glu Ile Thr Phe Asp Tyr Trp
1               5                   10

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ser Gly Tyr Thr Phe Thr Asp Tyr Phe Ile
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Glu Ile Tyr Pro Gly Ser Ser Asn Thr Tyr
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Ala Arg Ser Gly Ile Ser Pro Phe Thr Tyr Trp
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ser Gly Tyr Ile Phe Thr Gly Tyr Asn Ile
1               5                   10
```

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Val Tyr Pro Gly Asn Gly Asp Thr Ser
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Ala Lys Tyr Asp Arg Phe Phe Ala Ser Trp
1               5                   10

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ser Gln Gly Ile Ser Asn His Leu
1               5

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Tyr Phe Thr Ser Ser
1               5

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Cys Gln Gln Tyr Ser Asn Leu Pro Tyr Thr Phe
1               5                   10

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 149

Ser Gln Gly Ile Arg Asn Tyr Leu
1               5

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Tyr Phe Thr Ser Ser
1               5

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Cys Gln Gln Tyr Ser Asn Leu Pro Tyr Thr Phe
1               5                   10

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ser Gln Gly Ile Ser Asn His Leu
1               5

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Tyr Phe Thr Ser Ser
1               5

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Cys Gln Gln Tyr Ser Asn Leu Pro Tyr Thr Phe
1               5                   10

<210> SEQ ID NO 155
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Gln Gly Ile Asn Asn Tyr Leu
1               5

<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Tyr Tyr Thr Ser Ser
1               5

<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Cys Gln Gln Tyr Ser Lys Ile Pro Tyr Thr Cys
1               5                   10

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Gln Gly Ile Ser Asn His Leu
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Tyr Phe Thr Ser Ser
1               5

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Gln Gln Tyr Ser Asn Leu Pro Tyr Thr Phe
```

```
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Gln Ser Val Asp His Asp Gly Asp Ser Tyr Met
1               5                   10

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Tyr Ala Ala Ser Asn
1               5

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Gln Gln Asn Tyr Glu Asp Pro Thr Phe
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Gln Ser Val Asp Tyr Asp Gly Asp Ser Tyr Met
1               5                   10

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Tyr Ala Ala Ser Asn
1               5

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 166

Cys Gln Gln Ser Asn Glu Asp Pro Thr Phe
1               5                   10

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Gln Asp Ile Ser Asn Tyr Leu
1               5

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Tyr Tyr Thr Ser Arg
1               5

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Cys Gln Gln Gly Asp Ala Leu Pro Trp Thr Phe
1               5                   10

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Gln Asp Ile Ser Thr Tyr Leu
1               5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Phe Tyr Thr Ser Arg
1               5

<210> SEQ ID NO 172

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys Gln Gln Gly Asn Ser Leu Pro Phe Thr Phe
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Thr Ser Ser Ile Ser Ser Ser Tyr Leu
1               5

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Tyr Gly Thr Ser Asn
1               5

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Cys Gln Gln Trp Ser Ser Arg Pro Pro Thr Phe
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asn Ser Ser Val Ser Ser Ser Tyr Leu
1               5

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177
```

```
<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Gln Gln Tyr Ser Gly Tyr Pro Leu Thr Phe
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Thr Ser Ser Ile Ser Ser Ser Tyr Leu
1               5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Tyr Gly Thr Ser Asn
1               5

<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Cys Gln Gln Tyr Ser Asp Tyr Pro Leu Thr Phe
1               5                   10

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Thr Ser Ser Ile Ser Ser Ser Tyr Leu
1               5

<210> SEQ ID NO 183
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 183

Tyr Gly Thr Ser Asn
1               5

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Gln Gln Arg Ser Tyr Phe Pro Phe Thr Phe
1               5                   10

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Glu Asn Ile Tyr Tyr Asn Leu
1               5

<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Tyr Asn Ala Asn Ser
1               5

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Cys Lys Gln Val Tyr Asp Val Pro Phe Thr Phe
1               5                   10

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ser Glu Asn Ile Tyr Gly Tyr Phe
1               5
```

```
<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Tyr Asn Ala Lys Thr
1               5

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Cys Gln His His Tyr Gly Thr Pro Phe Thr Phe
1               5                   10

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Gln Asp Ile Asn Asn Tyr Ile
1               5

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

His Tyr Thr Ser Thr
1               5

<210> SEQ ID NO 193
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Leu Gln Tyr Asp Asn Leu Trp Thr Phe
1               5                   10

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194
```

```
Ser Gln Asp Ile Asn Lys Tyr Ile
1               5

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

His Tyr Thr Ser Thr
1               5

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Leu Gln Tyr Asp Asn Leu Trp Thr Phe
1               5                   10

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Glu Asn Ile Tyr Ser Tyr Leu
1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Tyr Asn Ala Lys Thr
1               5

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Cys Gln His His Tyr Gly Tyr Pro Tyr Thr Phe
1               5                   10

<210> SEQ ID NO 200
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 200

Ser Gln Gly Ile Arg Asn Tyr Leu
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Tyr His Thr Ser Thr
1               5

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Cys Gln Gln Tyr Ser Asn Leu Pro Leu Thr Phe
1               5                   10

<210> SEQ ID NO 203
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Gln Asp Val Arg Thr Asp Val
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Tyr Ser Ala Ser Phe
1               5

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Cys Gln Gln His Tyr Thr Ser Pro Trp Thr Phe
1               5                   10
```

```
<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Gln Asp Val Ile Thr Ala Val
1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Tyr Ser Ala Ser Tyr
1               5

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Cys Gln Gln His Tyr Ser Thr Pro Trp Thr Phe
1               5                   10

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Gln Ser Ile Gly Thr Ser Ile
1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Lys Ser Ala Ser Glu
1               5

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 211

Cys Gln Gln Ser Asn Arg Trp Pro Leu Thr Phe
1               5                   10

<210> SEQ ID NO 212
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Ser Gln Ser Leu Leu Asn Gln Lys Asn Tyr Leu
1               5                   10

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Tyr Trp Ala Ser Thr
1               5

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Cys Gln Asn Asp Tyr Asp Tyr Pro Tyr Thr Phe
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Ser Ser Val Ser Ser Ser Tyr Leu
1               5

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Tyr Ser Thr Ser Asn
1               5

<210> SEQ ID NO 217
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 217

Cys His Gln Tyr His Arg Ser Pro Leu Thr Phe
1               5                   10

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Glu Asn Ile Tyr Tyr Asn Leu
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Tyr Asn Ala Asn Ser
1               5

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Cys Gln Gln Thr Phe Asp Val Pro Trp Thr Phe
1               5                   10

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser Gln Thr Ile Gly Thr Ser Ile
1               5

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Lys Asn Ala Ser Glu
1               5
```

<210> SEQ ID NO 223
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Cys Gln Gln Ser Asn Ser Trp Pro Leu Thr Tyr
1               5                   10

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Gln Ser Leu Leu Tyr Ser Ser Asp Gln Lys Asn Tyr Leu
1               5                   10

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Tyr Trp Ala Ser Thr
1               5

<210> SEQ ID NO 226
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Cys Gln Gln Tyr Tyr Asn Tyr Pro Leu Thr Phe
1               5                   10

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Asn Ser Ser Val Ser Tyr Met
1               5

<210> SEQ ID NO 228
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Tyr Asp Thr Ser Lys
1               5

<210> SEQ ID NO 229
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Cys Gln Gln Trp Ser Ser Asn Pro Phe Thr Phe
1               5                   10

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Glu Asn Ile Tyr Tyr Asn Leu
1               5

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Tyr Asn Ala Asn Ser
1               5

<210> SEQ ID NO 232
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Cys Lys Gln Ala Tyr Asp Val Pro Trp Thr Phe
1               5                   10

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Ser Ser Leu Ser Tyr Met
1               5

<210> SEQ ID NO 234
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Tyr Asp Thr Ser Asn
1               5

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Cys Gln Gln Trp Ser Ser Phe Pro Pro Thr Phe
1               5                   10

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Gln Arg Ile Gly Thr Ser Met
1               5

<210> SEQ ID NO 237
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Lys Ser Ala Ser Glu
1               5

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Cys Gln Gln Ser Asn Ser Trp Pro Leu Thr Phe
1               5                   10

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Gln Ser Ile Gly Thr Ser Ile
```

```
<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Lys Ser Ala Ser Glu
1               5

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Cys Gln Gln Ser Asn Ser Trp Pro Leu Thr Phe
1               5                   10

<210> SEQ ID NO 242
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ser Gln Asn Ile Gly Thr Ser Ile
1               5

<210> SEQ ID NO 243
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Lys Asp Ala Ser Glu
1               5

<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Cys Gln Gln Ser Asp Ser Trp Pro Leu Thr Phe
1               5                   10

<210> SEQ ID NO 245
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 245

Ile Ser Ser Val Ser Tyr Met
1               5

<210> SEQ ID NO 246
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Tyr Ala Thr Ser Asn
1               5

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Cys Gln Gln Trp Ser Ser Asn Pro Arg Thr Phe
1               5                   10

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ser Gln Thr Ile Ala Thr Ser Ile
1               5

<210> SEQ ID NO 249
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Lys Asn Ala Ser Glu
1               5

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Gln Gln Ser Asn Ser Trp Pro Leu Thr Phe
1               5                   10

<210> SEQ ID NO 251

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ser Gln Ser Leu Val His Ser Asn Gly Asn Thr Tyr Leu
1               5                   10

<210> SEQ ID NO 252
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Tyr Lys Val Ser Asn
1               5

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Cys Trp Gln Asn Thr His Phe Pro Gln Thr Phe
1               5                   10

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Asn Glu Ser Val Glu Tyr Ser Gly Thr Ser Leu Met
1               5                   10

<210> SEQ ID NO 255
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Ala Ala Ser Asn
1               5

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256
```

```
Cys Gln Gln Ser Arg Gln Val Pro Leu Thr Phe
 1               5                  10
```

<210> SEQ ID NO 257
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

```
Gln Val Thr Leu Lys Glu Ser Gly Pro Val Leu Val Lys Pro Thr Glu
 1               5                  10                  15

Thr Leu Thr Leu Thr Cys Thr Phe Ser Gly Phe Ser Leu Ser Thr Ser
                20                  25                  30

Gly Met Gly Val Gly Trp Ile Arg Gln Ala Pro Gly Lys Gly Leu Glu
            35                  40                  45

Trp Val Ala His Ile Trp Trp Asp Asp Val Tyr Tyr Asn Pro Ser
 50                  55                  60

Leu Lys Ser Arg Leu Thr Ile Thr Lys Asp Ala Ser Lys Asp Gln Val
 65                  70                  75                  80

Ser Leu Lys Leu Ser Ser Val Thr Ala Ala Asp Thr Ala Val Tyr Tyr
                85                  90                  95

Cys Val Arg Arg Ala Thr Gly Thr Gly Phe Asp Tyr Trp Gly Gln
            100                 105                 110

Gly Thr Leu Val Thr Val Ser Ser
            115                 120
```

<210> SEQ ID NO 258
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

```
Asn Ile Val Met Thr Gln Ser Pro Ser Ser Leu Ser Ala Ser Val Gly
 1               5                  10                  15

Asp Arg Val Thr Ile Thr Cys Gln Ala Ser Gln Asp Val Gly Thr Ala
                20                  25                  30

Val Ala Trp Tyr Gln Gln Lys Pro Asp Gln Ser Pro Lys Leu Leu Ile
            35                  40                  45

Tyr Trp Thr Ser Thr Arg His Thr Gly Val Pro Asp Arg Phe Thr Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys
            100                 105
```

<210> SEQ ID NO 259
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 259

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Val Ile Ser Glu Asn Gly Ser Asp Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

Gly Thr Leu Val Thr Val Ser Ser
        115                 120

<210> SEQ ID NO 260
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
            100                 105

<210> SEQ ID NO 261
<211> LENGTH: 438
<212> TYPE: PRT
<213> ORGANISM: Homo sapiens

<400> SEQUENCE: 261

Met Val Cys Ser Gln Ser Trp Gly Arg Ser Ser Lys Gln Trp Glu Asp
1               5                   10                  15

Pro Ser Gln Ala Ser Lys Val Cys Gln Arg Leu Asn Cys Gly Val Pro
            20                  25                  30

Leu Ser Leu Gly Pro Phe Leu Val Thr Tyr Thr Pro Gln Ser Ser Ile
        35                  40                  45

Ile Cys Tyr Gly Gln Leu Gly Ser Phe Ser Asn Cys Ser His Ser Arg
    50                  55                  60

Asn Asp Met Cys His Ser Leu Gly Leu Thr Cys Leu Glu Pro Gln Lys

```
              65                  70                  75                  80
Thr Thr Pro Pro Thr Thr Arg Pro Pro Thr Thr Pro Glu Pro
                    85                  90                  95

Thr Ala Pro Pro Arg Leu Gln Leu Val Ala Gln Ser Gly Gly Gln His
                100                 105                 110

Cys Ala Gly Val Val Glu Phe Tyr Ser Gly Ser Leu Gly Gly Thr Ile
                115                 120                 125

Ser Tyr Glu Ala Gln Asp Lys Thr Gln Asp Leu Glu Asn Phe Leu Cys
                130                 135                 140

Asn Asn Leu Gln Cys Gly Ser Phe Leu Lys His Leu Pro Glu Thr Glu
145                 150                 155                 160

Ala Gly Arg Ala Gln Asp Pro Gly Glu Pro Arg Glu His Gln Pro Leu
                165                 170                 175

Pro Ile Gln Trp Lys Ile Gln Asn Ser Ser Cys Thr Ser Leu Glu His
                180                 185                 190

Cys Phe Arg Lys Ile Lys Pro Gln Lys Ser Gly Arg Val Leu Ala Leu
                195                 200                 205

Leu Cys Ser Gly Phe Gln Pro Lys Val Gln Ser Arg Leu Val Gly Gly
210                 215                 220

Ser Ser Ile Cys Glu Gly Thr Val Glu Val Arg Gln Gly Ala Gln Trp
225                 230                 235                 240

Ala Ala Leu Cys Asp Ser Ser Ala Arg Ser Ser Leu Arg Trp Glu
                245                 250                 255

Glu Val Cys Arg Glu Gln Gln Cys Gly Ser Val Asn Ser Tyr Arg Val
                260                 265                 270

Leu Asp Ala Gly Asp Pro Thr Ser Arg Gly Leu Phe Cys Pro His Gln
                275                 280                 285

Lys Leu Ser Gln Cys His Glu Leu Trp Glu Arg Asn Ser Tyr Cys Lys
                290                 295                 300

Lys Val Phe Val Thr Cys Gln Asp Pro Asn Pro Ala Gly Leu Ala Ala
305                 310                 315                 320

Gly Thr Val Ala Ser Ile Ile Leu Ala Leu Val Leu Leu Val Val Leu
                325                 330                 335

Leu Val Val Cys Gly Pro Leu Ala Tyr Lys Lys Leu Val Lys Lys Phe
                340                 345                 350

Arg Gln Lys Lys Gln Arg Gln Trp Ile Gly Pro Thr Gly Met Asn Gln
                355                 360                 365

Asn Met Ser Phe His Arg Asn His Thr Ala Thr Val Arg Ser His Ala
                370                 375                 380

Glu Asn Pro Thr Ala Ser His Val Asp Asn Glu Tyr Ser Gln Pro Pro
385                 390                 395                 400

Arg Asn Ser His Leu Ser Ala Tyr Pro Ala Leu Glu Gly Ala Leu His
                405                 410                 415

Arg Ser Ser Met Gln Pro Asp Asn Ser Ser Asp Ser Asp Tyr Asp Leu
                420                 425                 430

His Gly Ala Gln Arg Leu
                435
```